US011731979B2

(12) United States Patent
Kupper et al.

(10) Patent No.: US 11,731,979 B2
(45) Date of Patent: Aug. 22, 2023

(54) OPIOID KETAL COMPOUNDS AND USES THEREOF

(71) Applicant: Rhodes Technologies, Coventry, RI (US)

(72) Inventors: Robert J. Kupper, Warwick, RI (US); Raymond C. Glowaky, Killingworth, CT (US)

(73) Assignee: Rhodes Technologies, Coventry, RI (US)

( * ) Notice: Subject to any disclaimer, the term of this patent is extended or adjusted under 35 U.S.C. 154(b) by 0 days.

(21) Appl. No.: 17/407,222

(22) Filed: Aug. 20, 2021

(65) Prior Publication Data

US 2022/0041612 A1    Feb. 10, 2022

Related U.S. Application Data

(60) Division of application No. 16/860,316, filed on Apr. 28, 2020, now Pat. No. 11,130,765, which is a
(Continued)

(51) Int. Cl.
*C07D 489/08* (2006.01)
*C07D 491/20* (2006.01)
(Continued)

(52) U.S. Cl.
CPC .......... *C07D 489/08* (2013.01); *A61K 9/0053* (2013.01); *A61K 31/485* (2013.01);
(Continued)

(58) Field of Classification Search
CPC ... C07D 489/02; C07D 489/08; A61K 31/485
See application file for complete search history.

(56) References Cited

U.S. PATENT DOCUMENTS

| 4,140,755 A | 2/1979 | Sheth et al. |
| 4,167,558 A | 9/1979 | Sheth et al. |

(Continued)

FOREIGN PATENT DOCUMENTS

| GB | 981046 A | 1/1965 |
| WO | WO 03/084520 A2 | 10/2003 |

(Continued)

OTHER PUBLICATIONS

Foss, J.F., "A Review of the Potential Role of Methylnaltrexone in Opioid Bowel Dysfunction," *American Journal of Surgery* 182(Suppl to Nov. 2001):19S-26S, Excerpta Medica, Inc., United States (2001).
(Continued)

*Primary Examiner* — Marcos L Sznaidman

(74) *Attorney, Agent, or Firm* — Sterne, Kessler, Goldstein & Fox, P.L.L.C.

(57) ABSTRACT

This invention relates to opioid ketal compounds of Formula (I), Formula (II), or Formula (III): or a pharmaceutically acceptable salts thereof, wherein $R_1$ is H or $CH_3$, $R_2$ is H or OH, n is 0, 1, 2 or 3, $R_3$ and $R_4$ are independently H or optionally substituted $C_1$-$C_4$ alkyl, or when n is 0, then $R_3$ and $R_4$ and the carbon atoms to which they are attached together form six, or seven membered ring, which is optionally mono or disubstituted by $C_1$-$C_4$ alkyl. The invention also relates to oxycodone ketal compounds of Formula (IV) or (V): or a pharmaceutically acceptable salts thereof. The invention also relates to the use of such compounds for the treatment, prevention, or amelioration of pain.

(Continued)

-continued

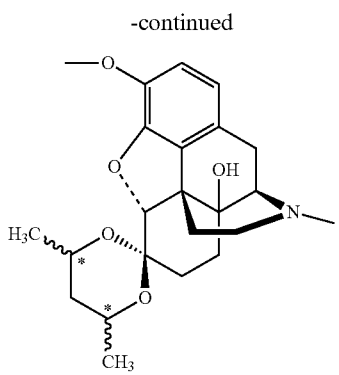

IV

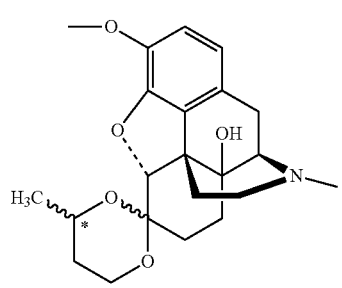

V

11 Claims, 9 Drawing Sheets

Related U.S. Application Data continuation of application No. 16/517,974, filed on Jul. 22, 2019, now Pat. No. 11,091,496, which is a continuation of application No. 14/893,224, filed as application No. PCT/IB2014/000876 on May 23, 2014, now abandoned.

(60) Provisional application No. 61/942,993, filed on Feb. 21, 2014, provisional application No. 61/836,433, filed on Jun. 18, 2013, provisional application No. 61/827,481, filed on May 24, 2013.

(51) Int. Cl.
| C07D 489/09 | (2006.01) |
| A61K 9/00 | (2006.01) |
| A61K 31/485 | (2006.01) |
| A61K 45/06 | (2006.01) |
| C07D 489/02 | (2006.01) |

(52) U.S. Cl.
CPC ............ A61K 45/06 (2013.01); C07D 489/02 (2013.01); C07D 489/09 (2013.01); C07D 491/20 (2013.01)

(56) References Cited

U.S. PATENT DOCUMENTS

| 5,169,638 | A | 12/1992 | Dennis et al. |
| 5,232,704 | A | 8/1993 | Franz et al. |
| 5,672,360 | A | 9/1997 | Sackler et al. |
| 5,968,551 | A | 10/1999 | Oshlack et al. |
| 6,090,411 | A | 7/2000 | Pillay et al. |
| 6,225,321 | B1 | 5/2001 | Hu et al. |
| 6,294,195 | B1 | 9/2001 | Oshlack et al. |
| 6,635,279 | B2 | 10/2003 | Kolter et al. |
| 7,157,100 | B2 | 1/2007 | Doshi et al. |
| 7,230,005 | B2 | 6/2007 | Shafer et al. |
| 7,270,831 | B2 | 9/2007 | Oshlack et al. |
| 7,514,100 | B2 | 4/2009 | Oshlack et al. |
| 7,838,028 | B2 | 11/2010 | Grenier et al. |
| 11,091,496 | B2 | 8/2021 | Kupper et al. |
| 11,130,865 | B2 | 9/2021 | Bremberg et al. |
| 2003/0124185 | A1 | 7/2003 | Oshlack et al. |
| 2006/0013876 | A1 | 1/2006 | Lohray et al. |
| 2008/0318905 | A1 | 12/2008 | Muhammad et al. |
| 2009/0192095 | A1 | 7/2009 | Franklin et al. |
| 2012/0035366 | A1 | 2/2012 | Wang et al. |
| 2016/0244459 | A1 | 8/2016 | Kupper et al. |
| 2016/0264589 | A1 | 9/2016 | Kupper et al. |
| 2020/0048269 | A1 | 2/2020 | Kupper et al. |
| 2020/0317684 | A1 | 10/2020 | Kupper et al. |

FOREIGN PATENT DOCUMENTS

| WO | WO 2004/082620 A2 | 9/2004 |
| WO | WO 2012/005795 A1 | 1/2012 |
| WO | WO 2013/036729 A1 | 3/2013 |

OTHER PUBLICATIONS

Goodson, J.M., "Dental Applications," in *Medical Applications of Controlled Release*, vol. II, Langer, R.S. and Wise, D.L., eds., pp. 115-138, CRC Press, Inc., United States (1984).
Hanson, G.R., "Analgesic, Antipyretic and Anti-inflammatory Drugs," in *Remington: The Science and Practice of Pharmacy*, vol. II, 19th Edition, Gennaro, A.R., ed., pp. 1196-1221, Williams & Wilkins, United States (1995).
Hunskaar, S., et al., "Formalin Test in Mice, a Useful Technique for Evaluating Mild Analgesics," *Journal of Neuroscience Methods* 14(1):69-76, Elsevier/North-Holland Biomedical Press, Netherlands (1985).
International Preliminary Report on Patentability for International Application No. PCT/IB2014/000876, The International Bureau of WIPO, Switzerland, dated Nov. 24, 2015, 9 pages.
International Search Report for International Application No. PCT/IB2014/000876, European Patent Office, Netherlands, dated Aug. 20, 2014, 4 pages.
Insel, P.A., "Analgesic-Antipyretic and Antiinflammatory Agents and Drugs Employed in the Treatment of Gout," in *Goodman & Gilman's the Pharmacological Basis of Therapeutics*, 9th Edition, Molinoff, P.B. and Ruddon, R.W., eds., pp. 617-657, McGraw Hill, United States (1996).
Langer, R., "New Methods of Drug Delivery," *Science* 249(4976):1527-1533, American Association for the Advancement of Science, United States (1990).
Lester, M.G., et al., "Vilsmeier Reactions with Cyclic Ketals of 14-hydroxydihydrocodeinone and Some New Cyclic Derivatives of 14-hydroxydihydrocodeinone," *Tetrahedron* 21(4):771-778, Pergamon Press, United Kingdom (1965).
McCurdy, C.R., et al., "Investigation of Phenolic Bioisosterism in Opiates: 3-sulfonamido Analogues of Naltrexone and Oxymorphone," *Organic Letters* 2(6):819-821, American Chemical Society, United States (2000).
Radebaugh, G.W., et al., *Remington: The Science and Practice of Pharmacy*, vol. II, 19th Edition, Gennaro, A.R., ed., pp. 1447-1676, Williams & Wilkins, United States (1995).
Sharma, D., et al., "Role of Endothelin and Inflammatory Cytokines in Pre-eclampsia—A Pilot North Indian Study," *American Journal of Reproductive Immunology* 65(4):428-432, John Wiley & Sons A/S, United States (2011).
Trauner, D., et al., "Synthesis of Enantiomerically Pure Morphine Alkaloids: The Hydrophenanthrene Route," *Journal of Organic Chemistry* 63(17):5908-5918, American Chemical Society, United States (1998).
Wise, D.L., "Controlled Release for Use in Treatment of Narcotic Addiction," in *Medical Applications of Controlled Release*, vol. II, Langer, R.S. and Wise, D.L., eds., pp. 107-114, CRC Press, Inc., United States (1984).

(56) References Cited

OTHER PUBLICATIONS

Drewes, A. M. et al., "Differences between opioids: pharmacological, clinical and economical perspectives," *British Journal of Clinical Pharmacology* 75(1):60-78, The British Pharmacological Society, United Kingdom (2012).

Barron, D.I. et al., "The analgesic and related properties of 6-deoxy-6,6-ethylenedioxy-7,8-dihydro-14-hydroxycodeinone hydrochloride," *J. Pharm. Pharmac.* 18:239-245, Wiley-Blackwell, United Kingdom (1966).

RD Chemicals Brochure, "2,4-Pentanediol, CAS No. 625-69-4," publ. Jun. 28, 2012, accessed at http://web.archive.org/web/20120628061022/http://rdchemicals.com/chemicals.php?mode=details&mol_id=2482, accessed on Jan. 11, 2017, 2 pages.

Cordes, E.H., et al., "Mechanism and Catalysis for Hydrolysis of Acetals, Ketals, and Ortho Esters," Chemical Reviews 74(5): 581-603, American Chemical Society, United States (1973).

Office Action dated Apr. 22, 2019, in U.S. Appl. No. 14/893,224, inventors Kupper et al., having a 371(c) date of Nov. 23, 2015, 25 pages.

Office Action dated Aug. 28, 2018, in U.S. Appl. No. 14/893,224, inventors Kupper et al., having a 371(c) date of Nov. 23, 2015, 25 pages.

Office Action dated Sep. 21, 2017, in U.S. Appl. No. 14/893,224, inventors Kupper et al., having a 371(c) date of Nov. 23, 2015, 25 pages.

Office Action dated Feb. 24, 2017, in U.S. Appl. No. 14/893,224, inventors Kupper et al., having a 371(c) date of Nov. 23, 2015, 25 pages.

Office Action dated Jan. 30, 2017, in U.S. Appl. No. 15/146,619, inventors Kupper et al., filed May 4, 2016, 19 pages.

Office Action dated Sep. 20, 2017, in U.S. Appl. No. 15/146,619, inventors Kupper et al., filed May 4, 2016, 25 pages.

Office Action dated Jun. 15, 2018, in U.S. Appl. No. 15/146,619, inventors Kupper et al., filed May 4, 2016, 22 pages.

Office Action dated Nov. 30, 2018, in U.S. Appl. No. 15/146,619, inventors Kupper et al., filed May 4, 2016, 20 pages.

Office Action dated Dec. 13, 2019, in U.S. Appl. No. 15/146,619, inventors Kupper et al., filed May 4, 2016, 18 pages.

TCI America Brochure 2, 4-pentadienol, retrieved from: http://www.tcichemicals.com/eshop/en/us/commodity/P0670/index.html, retrieved on Dec. 7, 2016, 3 pages.

TCI America Brochure 1, 3-butanediol, retrieved from: http://www.tcichemicals.com/eshop/en/us/commodity/B0679/, retrieved on Dec. 8, 2016, 3 pages.

ALFA Brochure 2,4-hexanediol, retrieved from: http://www.alfa-chemistry.com/cas_19780-90-6.htm, retrieved on Dec. 8, 2016, 4 pages.

ChemTik Brochure 3,5-heptanediol, retrieved from: http://www.chemtik.com/pro_result/326842, retrieved on Dec. 8, 2016, 1 page.

Office Action dated May 1, 2020, in U.S. Appl. No. 15/146,619, inventors Kupper et al., filed May 4, 2016, 20 pages.

Notice of Allowance dated Feb. 5, 2021, in U.S. Appl. No. 15/146,619, inventors Kupper et al., filed May 4, 2016, 9 pages.

Office Action dated Jul. 27, 2020, in U.S. Appl. No. 16/517,974, inventors Kupper et al., filed Jul. 22, 2019, 23 pages.

Notice of Allowance dated Apr. 15, 2021, in U.S. Appl. No. 16/517,974, inventors Kupper et al., filed Jul. 22, 2019, 9 pages.

Notice of Allowance dated May 26, 2021, in U.S. Appl. No. 16/860,316, inventors Kupper et al., filed Apr. 28, 2020, 7 pages.

Office Action dated Aug. 5, 2021, in U.S. Appl. No. 16/817,794, inventors Kupper et al., filed Mar. 13, 2020, 31 pages.

Final Office Action dated Feb. 3, 2022, in U.S. Appl. No. 16/817,794, inventors Kupper et al., filed Mar. 13, 2020, 21 pages.

Office Action dated Dec. 1, 2022, in U.S. Appl. No. 16/817,794, inventors Kupper et al., filed Mar. 13, 2020, 11 pages.

Ito, N., et al., "A medium-term rat liver bioassay for rapid in vivo detection of carcinogenic potential of chemicals," Cancer Sci 94(1):3-8, Wiley-Blackwell on behalf of the Japanese Cancer Association, United Kingdom (Jan. 2003).

R&D Chemicals, "2,4-Pentanediol," Brochure, CAS No. 625-69-4, accessed at [http://web.archive.org/web/20120628061022/http://www.rdchemicals.com/chemicals.php?mode=details&mol_id=2482] on Jan. 11, 2017, 2 pages (Jun. 2012).

Sigma-Aldrich, "Product Specification," Brochure, Product No. H11904, CAS No. 2935-44-6, 1 page (Jun. 2010).

OPIOID KETAL COMPOUNDS AND USES THEREOF

BACKGROUND OF THE INVENTION

Field of the Invention

This invention is in the field of medicinal chemistry. In particular, the invention relates to novel opioid ketal compounds.

Related Art

The primary location of pain control is in the central nervous system (CNS). The three primary classes of opioid receptors, µ (mu), κ (kappa), and δ (delta), are distributed throughout the CNS and the periphery (Foss, J. F., *The American Journal of Surgery* 182 (*Suppl. to November* 2001):19S-26S (2001)). The principal receptor involved in pain management is the p opioid receptor (Foss, J. F., ibid).

Opioids, also known as opioid agonists, are a group of compounds that bind to the above mentioned opioid receptors, and exhibit opium or morphine-like properties. The opioids are widely administered for a variety of medical indications but primarily they are employed as moderate to strong analgesics. Examples of opioid compounds include, but are not limited to, morphine, oxycodone, hydromorphone, oxymorphone, hydrocodone, levophanol, methadone, meperidine, fentanyl, codeine, propoxyphene, buprenorphine, butorphanol, pentazocine and nalbuphine.

The use of opioid compounds has been reported to have a number of potential side effects, including abuse and diversion.

There have been attempts to reduce the abuse potential of opioids. For example, various opioid receptor antagonists have been developed to block the action of opioid agonists when an overdose occurs. Also, in an attempt to formulate abuse-resistant tablets, various formulations have been developed containing an opioid receptor agonist combined with the opioid antagonist, wherein the antagonist becomes substantially bioavailable upon crushing or tampering with the tablets.

Other alternatives to reduce the abuse potential of opioids include the use of opioid prodrugs. Opioid prodrugs can exhibit different pharmacological properties than opioids, such as those relating to absorption, distribution, and elimination. For example, U.S. Pat. No. 6,225,321 describes nalbuphine polyester derivatives; U.S. Pat. No. 7,230,005 describes converting an opiate analgesic agent to its poorly absorbed ester prodrug or other prodrug derivatives; U.S. Patent Appl. Publication No. 2008/0318905 describes covalently attaching a prodrug moiety to the amine functional group of an abuse-prone parent drug; and U.S. Patent Appl. Publication No. 2009/0192095 describes opioid prodrugs comprising an opioid analgesic covalently bonded through a carbamate linkage to a peptide of 1-5 amino acids in length.

GB981046 and Lester et al., *Tetrahedron* 21:771-778 (1965), describe several opioid ketal compounds and the biological screening of an ethylene ketal analog of oxycodone.

There remains a need in the art to provide improved opioid prodrugs that provide effective analgesia while reducing the potential for abuse or adverse side effects.

SUMMARY OF THE INVENTION

One embodiment of the present invention is directed to the novel compounds represented by Formula I, Formula II, and Formula III, and the pharmaceutically acceptable salts thereof.

In another embodiment, the present invention is directed to novel compounds represented by Formula IV and Formula V, and the pharmaceutically acceptable salts thereof.

In another embodiment, the present invention is directed to a mixture, comprising at least two stereoisomers of a compound of Formula I, or a salt thereof. In another embodiment, the present invention is directed to a mixture, comprising at least two isomers of a compound of Formula III, or a salt thereof. In another embodiment, the present invention is directed to a mixture, comprising at least two isomers of a compound of Formula IV, or a salt thereof. In another embodiment, the present invention is directed to a mixture, comprising at least two isomers of a compound of Formula V, or a salt thereof.

In another embodiment, the present invention is directed to pharmaceutical compositions comprising a therapeutically effective amount of a compound of Formula I, Formula II, or Formula III, or a pharmaceutically acceptable salt thereof, and a pharmaceutically acceptable carrier. In another embodiment, the present invention is directed to pharmaceutical compositions comprising a therapeutically effective amount of a mixture of at least two isomers of a compound of Formula I or at least two isomers of a compound of Formula III, or the pharmaceutically acceptable salts thereof. In a particular embodiment, the pharmaceutical composition is an oral dosage form. In one embodiment, the pharmaceutical composition is a solid oral dosage form. In another embodiment, the pharmaceutical composition is a liquid oral dosage form. In one embodiment, the dosage form is designed for immediate release. In another embodiment, the dosage form is designed for controlled release.

In another embodiment, the present invention is directed to pharmaceutical compositions comprising a therapeutically effective amount of a compound of Formula IV or Formula V, or a pharmaceutically acceptable salt thereof, and a pharmaceutically acceptable carrier. In another embodiment, the present invention is directed to pharmaceutical compositions comprising a therapeutically effective amount of a mixture of at least two isomers of a compound of Formula IV or at least two isomers of a compound of Formula V, or the pharmaceutically acceptable salts thereof, and a pharmaceutically acceptable carrier. In a particular embodiment, the pharmaceutical composition is an oral dosage form. In one embodiment, the pharmaceutical composition is a solid oral dosage form. In another embodiment, the pharmaceutical composition is a liquid oral dosage form. In one embodiment, the dosage form is designed for immediate release. In another embodiment, the dosage form is designed for controlled release.

In another embodiment, the present invention is directed to methods of treating, ameliorating or preventing pain comprising administering a compound of Formula I, Formula II, or Formula III, or a pharmaceutically acceptable salt thereof, to a mammal in need of said treatment, amelioration or prevention. In another embodiment, the present invention is directed to methods of treating, ameliorating or preventing pain comprising administering a compound of Formula IV or Formula V, or a pharmaceutically acceptable salt thereof, to a mammal in need of said treatment, amelioration or prevention. In a particular embodiment, the administration is by the oral route. In one embodiment, the compound is in a solid oral dosage form. In another embodiment, the compound is in a liquid oral dosage form. In one embodiment, the dosage form is designed for immediate release. In another embodiment, the dosage form is designed for controlled release.

In another embodiment, the present invention is directed to methods of treating, ameliorating or preventing pain comprising administering a pharmaceutical composition of the invention to a mammal in need of said treatment, amelioration or prevention. In a particular embodiment, the administration is by the oral route. In one embodiment, the compound is in a solid oral dosage form. In another embodiment, the compound is in a liquid oral dosage form. In one embodiment, the dosage form is designed for immediate release. In another embodiment, the dosage form is designed for controlled release.

In another embodiment, the present invention is directed to a process for preparing a compound of Formula I, Formula II, or Formula III, or a salt thereof. In another embodiment, the present invention is directed to a process for preparing a compound of Formula IV or Formula V, or a salt thereof.

In another embodiment, the present invention is directed to a compound of Formula I, Formula II, or Formula III, or a pharmaceutically acceptable salt thereof, for use in the treatment, amelioration or prevention of pain. In another embodiment, the present invention is directed to a compound of Formula IV or Formula V, or a pharmaceutically acceptable salt thereof, for use in the treatment, amelioration or prevention of pain.

In another embodiment, the present invention is directed to the use of a compound of Formula I, Formula II, or Formula III, or a salt thereof, in the manufacture of a medicament for the treatment, amelioration or prevention of pain. In another embodiment, the present invention is directed to the use of a compound of Formula IV or Formula V, or a salt thereof, in the manufacture of a medicament for the treatment, amelioration or prevention of pain.

It is to be understood that both the foregoing general description and the following detailed description are exemplary and explanatory only and are not restrictive of the invention, as claimed.

BRIEF DESCRIPTION OF THE DRAWINGS

The following drawings are given by way of illustration only, and thus are not intended to limit the scope of the present invention.

DETAILED DESCRIPTION OF THE INVENTION

Definitions

Figure 1:
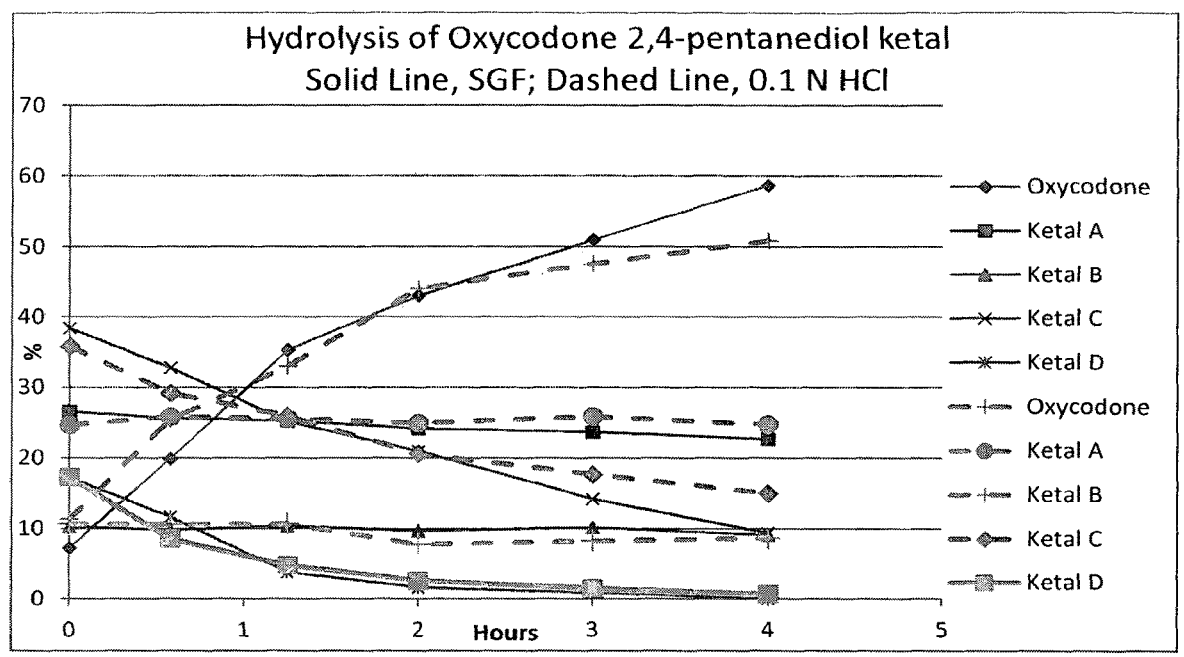
FIG. 1 is a graph of the hydrolysis of a mixture of four isomers of oxycodone 2,4-pentanediol ketal using Simulated Gastric Fluid (SGF) (0.2% NaCl and 0.32% pepsin in 0.084 N HCl) or 0.1 N HCl at 37° C. and the release of oxycodone. The samples were analyzed by LCMS. Hydrolysis using 0.1 N HCl simulates the acidic conditions within the human stomach. Hydrolysis using SGF provides a comparison with 0.1 N HCl to determine whether hydrolysis is affected by the presence of the pepsin enzyme.

As used herein, the term "isomer" is a general term for all isomers of individual molecules that differ only in the orientation of their atoms in space. It includes enantiomers and isomers of compounds with more than one chiral center that are not mirror images of one another (diastereomers).

The term "chiral center" refers to a carbon atom to which four different groups are attached.

The terms "R configuration" and "S configuration" refer to the right-handed and left-handed configurations, respectively, at a stereo center. The term "enantiomer" or "enantiomeric" refers to a molecule that is non-superimposeable on its mirror image and hence optically active wherein one enantiomer rotates the plane of polarized light in one direction and its mirror image enantiomer rotates the plane of polarized light in the opposite direction.

The term "racemic" refers to a mixture of equal parts of enantiomers and which, accordingly, is optically inactive.

The terms "resolution," "resolve," and the like, refer to the separation, concentration or depletion of one of the two enantiomeric forms of a molecule.

As used herein, the term "compound of Formula I" includes all stereoisomers, including enantiomers and diastereomers and mixtures of enantiomers and diastereomers of compounds of Formula I, including mixtures where one enantiomer or diastereomer is in excess of other isomers in the mixture.

As used herein, the term "compound of Formula III" includes all stereoisomers, including enantiomers and diastereomers and mixtures of enantiomers and diastereomers of compounds of Formula III, including mixtures where one enantiomer or diastereomer is in excess of other isomers in the mixture.

As used herein, the term "compound of Formula IV" includes isomers IVA, IVB, IVC, and IVD, all enantiomers and diastereomers and mixtures of enantiomers and diastereomers of compounds of Formula IV, including mixtures where one enantiomer or diastereomer is in excess of other isomers in the mixture.

As used herein, the term "compound of Formula V" includes isomers VA, VB, VC, and VD, all enantiomers and diastereomers and mixtures of enantiomers and diastereomers of compounds of Formula V, including mixtures where one enantiomer or diastereomer is in excess of other isomers in the mixture.

As used herein, the singular terms "a" and "the" are synonymous and used interchangeably with "one or more" and "at least one," unless the language and/or context clearly indicates otherwise. As used herein, the term "comprising" means including, made up of, and composed of. All numbers in this description indicating amounts, ratios of materials, physical properties of materials, and/or use are to be understood as modified by the word "about," except as otherwise explicitly indicated.

The invention disclosed herein is also meant to encompass all salts of the disclosed compounds. The invention disclosed herein is also meant to encompass all pharmaceutically acceptable salts of the disclosed compounds. Non-limiting examples of pharmaceutically acceptable salts include inorganic and organic salts, such as chloride, bromide, iodide, phosphate, sulphate, citrate, lactate, tartrate, maleate, succinate, fumarate, mandelate, acetate, dichloroacetate, trifluoroacetate, oxalate, formate, carbonate, sulfonate, methanesulfonate, ethanesulfonate, benzenesulfonate, naphthalenesulfonate or p-toluenesulfonate. Unless otherwise indicated, all references hereinafter to compounds of Formula I, compound of Formula II, and compounds of Formula III, are intended to include all pharmaceutically acceptable salts thereof. Unless otherwise indicated, all references hereinafter to compounds of Formula IV and compounds of Formula V, including one or more isomers IVA, IVB, IVC, IVD, VA, VB, VC and VD, are intended to include all pharmaceutically acceptable salts thereof.

As used herein, the term "delaying the onset" or "delayed onset" refers to the increased time to onset of therapeutic action post-administration provided by a compound of the present invention as compared to the corresponding amount of the parent opioid during the same length of time via the same route of administration.

As used herein, the terms "decrease the abuse potential," "decreased abuse potential," and the like refer to the reduced potential of a compound of the invention for improper non-medical and/or recreational administration as compared to the parent opioid, yet wherein the compound is still capable of delivering a therapeutically effective dosage of the opioid when administered as directed.

Use of phrases such as "decreased," "reduced," "diminished," or "lowered" in relation to abuse potential or overdose potential refer to at least about a 10% decrease in abuse potential or overdose potential as measured by one or more standard measures of such abuse potential or overdose as known in the art, with greater percentage changes being preferred for reduction in abuse potential and overdose potential. For instance, the decrease can be greater than 25%, 35%, 45%, 55%, 65%, 75%, 85%, 95%, 96%, 97%, 98%, or 99%.

As used herein, the term "$C_1$-$C_4$ alkyl" as used by itself or as part of another group refers to a straight- or branched-chain aliphatic hydrocarbon containing one to four, i.e. 1, 2, 3, or 4 carbon atoms or the number of carbon atoms designated (i.e., a $C_1$ alkyl such as methyl, a $C_2$ alkyl such as ethyl, a $C_3$ alkyl such as propyl or isopropyl, etc.). In one embodiment, the alkyl group is chosen from a straight chain $C_{1-4}$ alkyl group. In another embodiment, the alkyl group is chosen from a branched chain $C_{3-4}$ alkyl group. In another embodiment, the alkyl group is chosen from a straight or branched chain $C_{3-4}$ alkyl group. Non-limiting exemplary $C_{1-4}$ alkyl groups include methyl, ethyl, propyl, isopropyl, butyl, sec-butyl, tert-butyl, and Iso-butyl. A preferred $C_{1-4}$ alkyl group is methyl or ethyl.

As used herein, the term "optionally substituted $C_1$-$C_4$ alkyl" means that the alkyl as defined above is either unsubstituted or substituted with one, two, or three substituents independently chosen from halo (selected from F, Cl, Br or I), hydroxy, cyano, nitro, $C_1$-$C_4$-alkoxy, amino, $C_1$-$C_4$-alkylamino, di-($C_1$-$C_4$)-alkylamino, halo-$C_1$-$C_4$-alkoxy, carboxy, carboxy-$C_1$-$C_4$-alkyl, $C_1$-$C_4$-alkoxycarbonyl, and the like. In one embodiment, the optionally substituted alkyl is substituted with two substituents. In another embodiment, the optionally substituted alkyl is substituted with one substituent.

As used herein, the term "opioid" refers to a compound that binds to an opioid receptors, in particular to the μ (mu), κ (kappa), δ (delta) and ORL1 receptor. Preferably, the opioids of the present application are based on the morphinan or benzomorphan scaffold, i.e., derivatives of morphinan or benzomorphan scaffold. Examples of opioid compounds for use in the present application include, but are not limited to, morphine, oxycodone, hydromorphone, oxymorphone, hydrocodone, levorphanol, methadone, meperidine, fentanyl, codeine, propoxyphene, buprenorphine, butorphanol, pentazocine and nalbuphine. Preferably, the opioid compounds for use in the present application are selected from morphine, oxycodone, hydromorphone, oxymorphone, hydrocodone, levorphanol, codeine, buprenorphine, butorphanol, pentazocine and nalbuphine.

As used herein, the term "opioid therapy" refers to administration of an opioid to a subject for treatment or prophylaxis.

Compounds of Formula I, Formula II, Formula III, Formula IV, and Formula V

A compound of Formula I, Formula II, Formula III, Formula IV, or Formula V of the invention is a ketal derivative of an opioid. The opioid can be oxycodone, hydrocodone, oxymorphone, or hydromorphone. Compounds of Formula I, Formula II, Formula III, Formula IV, or Formula V react differently based on routes of administration to a mammal. Compounds of Formula I, Formula II, Formula III, Formula IV, and Formula V are designed to have low or no opioid activity when administered by an inappropriate route such as by parenteral administration (e.g., injection) or by transmucosal administration (e.g., intranasal, buccal, sublingual, or inhalation). In contrast, appropriate administration by the oral route of a compound of Formula I, Formula II, Formula III, Formula IV, or Formula V can result in effective opioid activity through the conversion of the opioid ketal derivative to the parent opioid by hydrolysis in the gastrointestinal (GI) tract. Therefore, compounds of Formula I, Formula II, Formula III, Formula IV, or Formula V, when administered orally, are useful for treating, ameliorating or preventing any condition for which opioid administration is known to be useful, including pain, and especially chronic pain, in a mammal in need thereof, while reducing the potential for intentional abuse or unintentional misuse via an inappropriate route of administration.

Particular compounds of Formula I, Formula III, Formula IV, and Formula V each have four possible isomers. Surprisingly, it has been found that different isomers of Formula I, Formula III, Formula IV and Formula V hydrolyze at different rates. By preparing isomers of Formula I, Formula III, Formula IV and Formula V, and using selected ones, or by combining two or more specific isomers in a mixture and adjusting and optimizing their relative ratios, a range of release rates and profiles of the parent opioid can be obtained. Accordingly, in one embodiment of the invention, specific mixtures of isomers of compounds of Formula I, Formula III, Formula IV, or Formula V can be used to achieve a desired release rate of the parent opioid in the mammal.

Compounds of Formula I have the following structural formula:

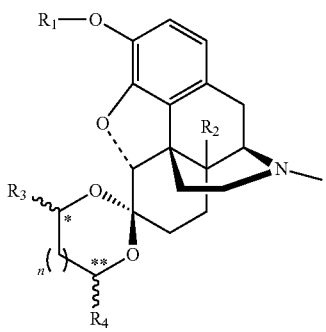

I and include the pharmaceutically acceptable salts thereof, wherein $R_1$ is H or $CH_3$,
$R_2$ is H or OH,
n is 0, 1, 2 or 3,
$R_3$ and $R_4$ are independently H or optionally substituted $C_1$-$C_4$ alkyl, or
when n is 0, then $R_3$ and $R_4$ and the carbon atoms to which they are attached together form a five, six, or seven membered ring, which is optionally mono- or di-substituted by independently selected $C_1$-$C_4$ alkyl,
and wherein the carbon atoms labeled * and ** are independently in the R or S configuration.

In one embodiment, the compound of Formula I is hydrocodone 2,4-pentanediol ketal or a pharmaceutically acceptable salt thereof, wherein $R_1$ is $CH_3$, $R_2$ is H, n is 1, and $R_3$ and $R_4$ are each $CH_3$. In one embodiment, the hydrocodone 2,4-pentanediol ketal is a specific stereoisomer in which the carbon atom labeled * and the carbon atom labeled ** are each independently in the R or S configuration. In one embodiment, the invention is hydrocodone 2,4-pentanediol ketal or a pharmaceutically acceptable salt thereof, in which the carbon atom labeled * and the carbon atom labeled ** are both in the R configuration. In one embodiment, the invention is hydrocodone 2,4-pentanediol ketal or a pharmaceutically acceptable salt thereof, in which the carbon atom labeled * and the carbon atom labeled ** are both in the S configuration. In another embodiment, the invention is hydrocodone 2,4-pentanediol ketal or a pharmaceutically acceptable salt thereof, in which the carbon atom labeled * is in the R configuration and the carbon atom labeled ** is in the S configuration. In another embodiment, the invention is hydrocodone 2,4-pentanediol ketal or a pharmaceutically acceptable salt thereof, in which the carbon atom labeled * is in the S configuration and carbon atom labeled ** is in the R configuration.

In one embodiment, the invention is a mixture, comprising two or more stereoisomers of hydrocodone 2,4-pentanediol ketal, or pharmaceutically acceptable salts thereof. In one embodiment, the mixture comprises two or more stereoisomers of hydrocodone 2,4-pentanediol ketal, or pharmaceutically acceptable salts thereof, wherein the stereoisomers are compounds in which the carbon atom labeled * and the carbon atom labeled ** are each independently in the R or S configuration. In another embodiment, the invention is a mixture of stereoisomers of hydrocodone 2,4-pentanediol ketal or pharmaceutically acceptable salts thereof, comprising an excess of compound wherein the carbon atom labeled * and the carbon atom labeled ** are both in the R configuration. In another embodiment, the invention is a mixture of stereoisomers of hydrocodone 2,4-pentanediol ketal or pharmaceutically acceptable salts thereof, comprising an excess of a compound wherein the carbon atom labeled * and the carbon atom labeled ** are both in the S configuration.

In one embodiment, the compound of Formula I is oxycodone 2,5-hexanediol ketal or a pharmaceutically acceptable salt thereof, wherein $R_1$ is $CH_3$, $R_2$ is OH, n is 2, and $R_3$ and $R_4$ are each $CH_3$. In one embodiment, the oxycodone 2,5-hexanediol ketal is a specific stereoisomer in which the carbon atom labeled * and the carbon atom labeled ** are each independently in the R or S configuration. In one embodiment, the invention is oxycodone 2,5-hexanediol ketal or a pharmaceutically acceptable salt thereof, in which the carbon atom labeled * and the carbon atom labeled ** are both in the R configuration. In one embodiment, the invention is oxycodone 2,5-hexanediol ketal or a pharmaceutically acceptable salt thereof, in which the carbon atom labeled * and the carbon atom labeled ** are both in the S configuration. In another embodiment, the invention is oxycodone 2,5-hexanediol ketal or a pharmaceutically acceptable salt thereof, in which the carbon atom labeled * is in the R configuration and the carbon atom labeled ** is in the S configuration. In another embodiment, the invention is oxycodone 2,5-hexanediol ketal or a pharmaceutically acceptable salt thereof, in which the carbon atom labeled * is in the S configuration and the carbon atom labeled ** is in the R configuration.

In one embodiment, the invention is a mixture, comprising two or more stereoisomers of oxycodone 2,5-hexanediol ketal, or pharmaceutically acceptable salts thereof. In one embodiment, the mixture comprises two or more stereoisomers of oxycodone 2,5-hexanediol ketal or pharmaceutically acceptable salts thereof, wherein the stereoisomers are compounds in which the carbon atom labeled * and the carbon atom labeled ** are each independently in the R or S configuration. In another embodiment, the invention is a mixture of stereoisomers of oxycodone 2,5-hexanediol ketal or pharmaceutically acceptable salts thereof, comprising an excess of a compound wherein the carbon atom labeled * and the carbon atom labeled ** are both in the R configuration. In another embodiment, the invention is a mixture of stereoisomers of oxycodone 2,5-hexanediol ketal or pharmaceutically acceptable salts thereof, comprising an excess of a compound wherein the carbon atom labeled * and the carbon atom labeled ** are both in the S configuration.

In one embodiment, the compound of Formula I is hydrocodone 2,5-hexanediol ketal or a pharmaceutically acceptable salt thereof, wherein $R_1$ is $CH_3$, $R_2$ is H, n is 2, and $R_3$ and $R_4$ are each $CH_3$. In one embodiment, the hydrocodone 2,5-hexanediol ketal is a specific stereoisomer in which the carbon atom labeled * and the carbon atom labeled ** are each independently in the R or S configuration. In one embodiment, the invention is hydrocodone 2,5-hexanediol ketal or a pharmaceutically acceptable salt thereof, in which the carbon atom labeled * and the carbon atom labeled ** are both in the R configuration. In one embodiment, the invention is hydrocodone 2,5-hexanediol ketal or a pharmaceutically acceptable salt thereof, in which the carbon atom labeled * and the carbon atom labeled ** are both in the S configuration. In another embodiment, the invention is hydrocodone 2,5-hexanediol ketal or a pharmaceutically acceptable salt thereof, in which the carbon atom labeled * is in the R configuration and the carbon atom labeled ** is in the S configuration. In another embodiment, the invention is hydrocodone 2,5-hexanediol ketal or a pharmaceutically acceptable salt thereof, in which the carbon atom labeled * is in the S configuration and carbon atom labeled ** is in the R configuration.

In one embodiment, the invention is a mixture, comprising two or more stereoisomers of hydrocodone 2,5-hexanediol ketal, or a salt thereof. In one embodiment, the mixture comprises two or more stereoisomers of hydrocodone 2,5-hexanediol ketal or pharmaceutically acceptable salts thereof, wherein the stereoisomers are compounds in which the carbon atom labeled * and the carbon atom labeled ** are each independently in the R or S configuration. In another embodiment, the invention is a mixture of stereoisomers of hydrocodone 2,5-hexanediol ketal or pharmaceutically acceptable salts thereof, comprising an excess of a compound wherein the carbon atom labeled * and the carbon atom labeled ** are both in the R configuration. In another embodiment, the invention is a mixture of stereoisomers of hydrocodone 2,5-hexanediol ketal or pharmaceutically acceptable salts thereof, comprising an excess of a compound wherein the carbon atom labeled * and the carbon atom labeled ** are both in the S configuration.

In one embodiment, the compound of Formula I is hydromorphone 2,4-pentanediol ketal or a pharmaceutically acceptable salt thereof, wherein $R_1$ is H, $R_2$ is H, n is 1, and $R_3$ and $R_4$ are each $CH_3$. In one embodiment, the hydromorphone 2,4-pentanediol ketal is a specific stereoisomer in which the carbon atom labeled * and the carbon atom labeled ** are each independently in the R or S configuration. In one embodiment, the invention is hydromorphone 2,4-pentanediol ketal or a pharmaceutically acceptable salt thereof, in which the carbon atom labeled * and the carbon atom labeled ** are both in the R configuration. In one embodiment, the invention is hydromorphone 2,4-pentanediol ketal or a pharmaceutically acceptable salt thereof, in which the carbon atom labeled * and the carbon atom labeled ** are both in the S configuration. In another embodiment, the invention is hydromorphone 2,4-pentanediol ketal or a pharmaceutically acceptable salt thereof, in which the carbon atom labeled * is in the R configuration and the carbon atom labeled ** is in the S configuration. In another embodiment, the invention is hydromorphone 2,4-pentanediol ketal or a pharmaceutically acceptable salt thereof, in which the carbon atom labeled * is in the S configuration and carbon atom labeled ** is in the R configuration.

In one embodiment, the invention is a mixture, comprising two or more stereoisomers of hydromorphone 2,4-pentanediol ketal, or pharmaceutically acceptable salts thereof. In one embodiment, the mixture comprises two or more stereoisomers of hydromorphone 2,4-pentanediol ketal or pharmaceutically acceptable salts thereof, wherein the stereoisomers are compounds in which the carbon atom labeled * and the carbon atom labeled ** are each independently in the R or S configuration. In another embodiment, the invention is a mixture of stereoisomers of hydromorphone 2,4-pentanediol ketal or pharmaceutically acceptable salts thereof, comprising an excess of a compound wherein the carbon atom labeled * and the carbon atom labeled ** are both in the R configuration. In another embodiment, the invention is a mixture of stereoisomers of hydromorphone 2,4-pentanediol ketal or pharmaceutically acceptable salts thereof, comprising an excess of a compound wherein the carbon atom labeled * and the carbon atom labeled ** are both in the S configuration.

In one embodiment, the compound of Formula I is oxycodone 1,2-cyclohexanediol ketal, or a pharmaceutically acceptable salt thereof, wherein $R_1$ is $CH_3$, $R_2$ is H, n is 0, and $R_3$ and $R_4$ together with the carbon atoms to which they are attached form a six membered carbon ring. In one embodiment, the oxycodone 1,2-cyclohexanediol ketal or pharmaceutically acceptable salts thereof, is a mixture of stereoisomers in which the carbon atom labeled * and the carbon atom labeled ** are in the cis configuration relative to each other.

In one embodiment, the invention is a mixture, comprising two or more stereoisomers of oxycodone 1,2-cyclohexanediol ketal, or pharmaceutically acceptable salts thereof. In one embodiment, the mixture comprises an excess of cis isomers of oxycodone 1,2-cyclohexanediol ketal or a pharmaceutically acceptable salt thereof.

In one embodiment, the compound of Formula I is oxycodone 3,5-octanediol ketal or a pharmaceutically acceptable salt thereof, wherein $R_1$ is $CH_3$, $R_2$ is OH, n is 1, and $R_3$ and $R_4$ are independently —$CH_2CH_3$ and $CH_2CH_2CH_3$. In one embodiment, the invention is a mixture, comprising two or more stereoisomers of oxycodone 3,5-octanediol ketal, or pharmaceutically acceptable salts thereof. In one embodiment, the mixture comprises two or more stereoisomers of oxycodone 3,5-octanediol ketal or pharmaceutically acceptable salts thereof, wherein the stereoisomers are compounds in which the carbon atom labeled * and the carbon atom labeled ** are each independently in the R or S configuration. In another embodiment, the invention is a mixture of stereoisomers of oxycodone 3,5-octanediol ketal or pharmaceutically acceptable salts thereof, comprising an excess of a compound wherein the carbon atom labeled * and the carbon atom labeled ** are both in the R configuration. In another embodiment, the invention is a mixture of stereoisomers of oxycodone 3,5-octanediol ketal or pharmaceutically acceptable salts thereof, comprising an excess of a compound wherein the carbon atom labeled * and the carbon atom labeled ** are both in the S configuration.

Other exemplary compounds of Formula I are:
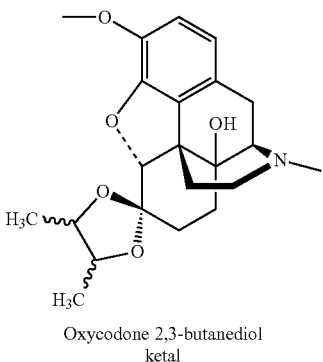
Oxycodone 2,3-butanediol ketal
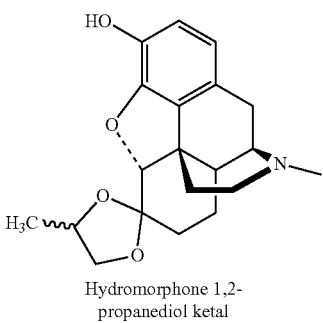
Hydromorphone 1,2-propanediol ketal
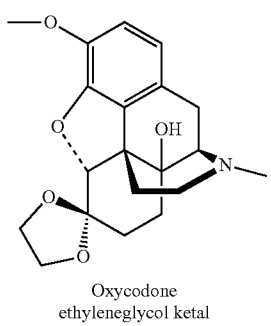
Oxycodone ethyleneglycol ketal
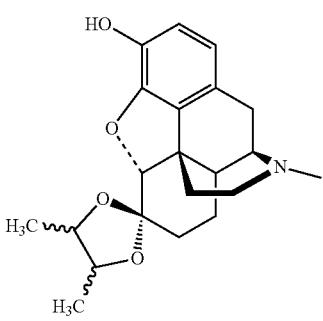
Hydromorphone 2,3-butanediol ketal
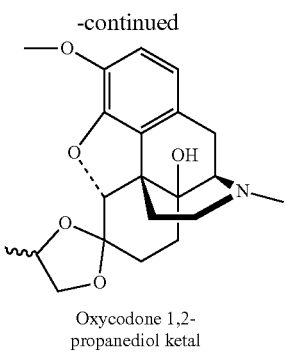
Oxycodone 1,2-propanediol ketal
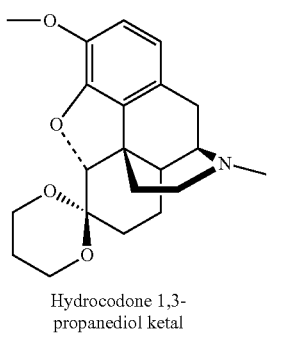
Hydrocodone 1,3-propanediol ketal
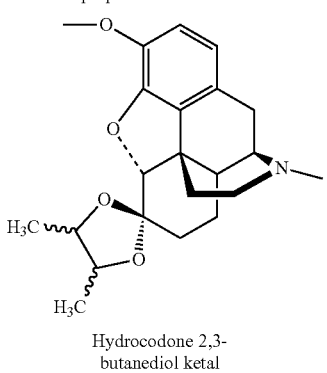
Hydrocodone 2,3-butanediol ketal
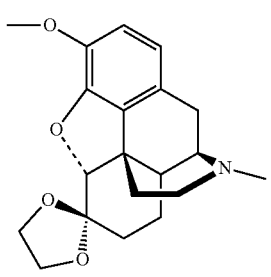
Hydrocodone ethyleneglycol ketal
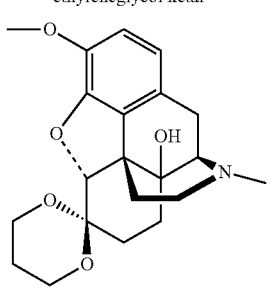
Oxycodone 1,3-propanediol ketal

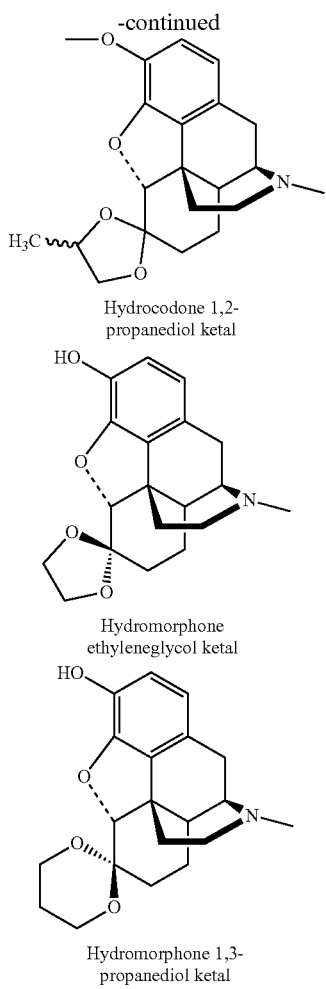

Hydrocodone 1,2-propanediol ketal

Hydromorphone ethyleneglycol ketal

Hydromorphone 1,3-propanediol ketal

In one embodiment, the compound of Formula I is an oxymorphone ketal, or a pharmaceutically acceptable salt thereof, wherein $R_1$ is $CH_3$ and $R_2$ is OH. In some embodiments, the compound of Formula I is oxymorphone ethyleneglycol ketal; oxymorphone 1,3-propanediol ketal; oxymorphone 1,2-propanediol ketal; oxymorphone 2,3-butanediol ketal; oxymorphone 2,4-pentanediol ketal; oxymorphone 2,5-hexanediol ketal; oxymorphone 1,2-cyclohexanediol ketal; or a pharmaceutically acceptable salt thereof. In another embodiment, the invention is a mixture, comprising two or more stereoisomers of oxymorphone 1,2-propanediol ketal; oxymorphone 2,3-butanediol ketal; oxymorphone 2,4-pentanediol ketal; oxymorphone 2,5-hexanediol ketal; or a pharmaceutically acceptable salt thereof.

In a particular embodiment, the invention is a compound of Formula I or a pharmaceutically acceptable salt thereof, with the proviso that the compound is not hydrocodone ethyleneglycol ketal; hydromorphone ethyleneglycol ketal; oxycodone ethyleneglycol ketal; hydrocodone 1,3-propanediol ketal; oxycodone 1,3-propanediol ketal; hydromorphone 1,3-propanediol ketal; or a pharmaceutically acceptable salt thereof. In another embodiment, the invention is a mixture comprising two or more stereoisomers of a compound of Formula I or pharmaceutically acceptable salts thereof, with the proviso that the mixture is not a mixture of stereoisomers of hydrocodone 2,3-butanediol ketal; oxycodone 2,3-butanediol ketal; hydrocodone 2,3-butanediol ketal; or pharmaceutically acceptable salts thereof.

Compounds of the present invention are also compounds of Formula II or Formula III.

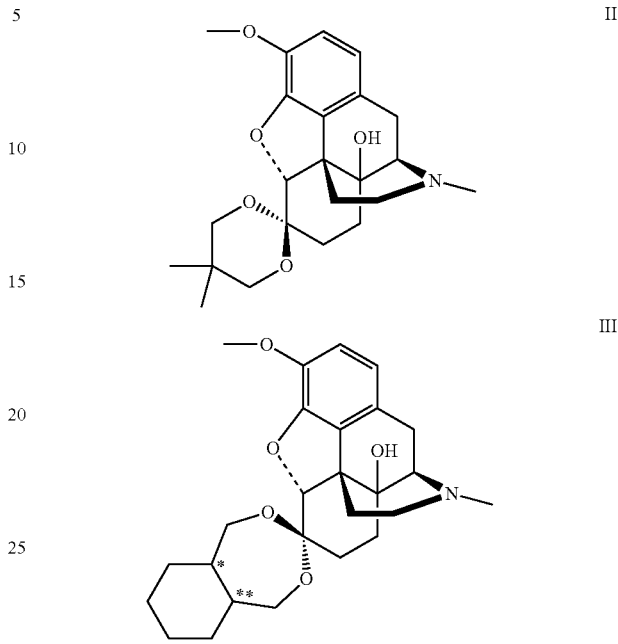

and the pharmaceutically acceptable salts thereof.

In one embodiment, the compound of Formula III, or pharmaceutically acceptable salt thereof, is a specific stereoisomer in which the carbon atom labeled * and the carbon atom labeled ** are in the cis configuration relative to each other. In one embodiment, the compound of Formula III or pharmaceutically acceptable salt thereof, is a specific stereoisomer in which the carbon atom labeled * and the carbon atom labeled ** are in the trans configuration relative to each other.

In one embodiment, the invention is a mixture, comprising two or more stereoisomers of a compound of Formula III, or pharmaceutically acceptable salts thereof. In one embodiment, the mixture comprises an excess of the cis isomer of the compound of Formula III or a pharmaceutically acceptable salt thereof. In another embodiment, the mixture comprises an excess of the trans isomer of the compound of Formula III or a pharmaceutically acceptable salt thereof.

In another embodiment, the invention includes compounds of Formula IV (oxycodone 2,4-pentanediol ketal) and Formula V (oxycodone 1,3-butanediol ketal):

IV

V

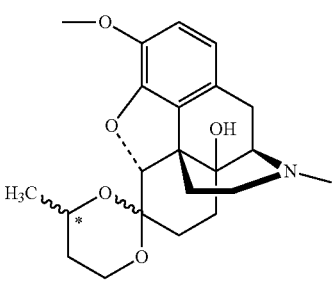

and the pharmaceutically acceptable salts thereof.

In one embodiment, the invention is an isomer of Formula IVA, IVB, IVC or IVD:

IVA

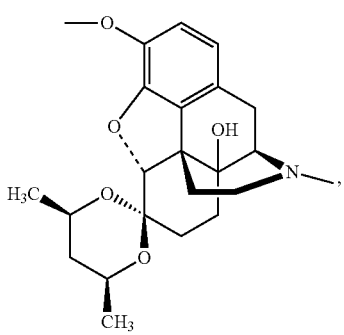

IVB

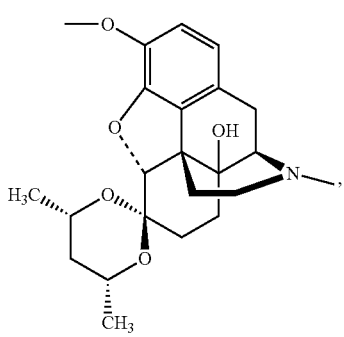

IVC

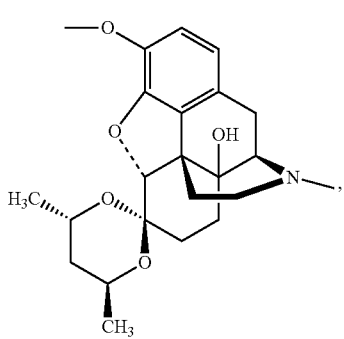

IVD

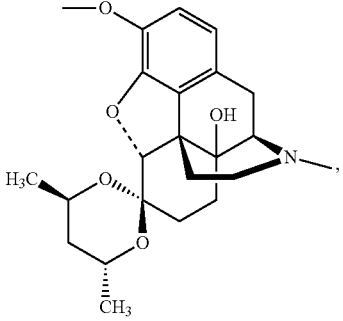

or a pharmaceutically acceptable salt thereof.

In one embodiment, the invention is a compound of Formula IV (oxycodone 2,4-pentanediol ketal) or a pharmaceutically acceptable salt thereof.

In one embodiment, the compound is isomer IVA (oxycodone 2R,4S-pentanediol ketal) or a pharmaceutically acceptable salt thereof.

In another embodiment, the compound is isomer IVB (oxycodone 2S,4R-pentanediol ketal) or a pharmaceutically acceptable salt thereof.

In another embodiment, the compound is isomer IVC (oxycodone 2S,4S-pentanediol ketal) or a pharmaceutically acceptable salt thereof.

In another embodiment, the compound is isomer IVD (oxycodone 2R,4R-pentanediol ketal) or a pharmaceutically acceptable salt thereof.

In a particular embodiment, the invention is a mixture of isomers of Formula IV or pharmaceutically acceptable salts thereof, comprising an excess of a compound wherein the carbon atoms labeled * are both in the R configuration (oxycodone 2R,4R-pentanediol ketal). In another embodiment, the invention is a mixture of isomers of Formula IV or pharmaceutically acceptable salts thereof, comprising an excess of a compound wherein the carbon atoms labeled * are both in the S configuration (oxycodone 2S,4S-pentanediol ketal).

In one embodiment, the invention is a mixture comprising at least two isomers of a compound of Formula IV selected from the group consisting of IVA, IVB, IVC and IVD and the pharmaceutically acceptable salts thereof.

In one embodiment, the mixture comprises isomers IVA and IVB or the pharmaceutically acceptable salts thereof.

In another embodiment, the mixture comprises isomers IVA and IVC or the pharmaceutically acceptable salts thereof.

In another embodiment, the mixture comprises isomers IVA and IVD or the pharmaceutically acceptable salts thereof.

In another embodiment, the mixture comprises isomers IVB and IVC or the pharmaceutically acceptable salts thereof.

In another embodiment, the mixture comprises isomers IVB and IVD or the pharmaceutically acceptable salts thereof.

In another embodiment, the mixture comprises isomers IVC and IVD or the pharmaceutically acceptable salts thereof.

In another embodiment, the mixture comprises isomers IVC and IVD or the pharmaceutically acceptable salts thereof, wherein the isomer IVC or its salt is present in an amount greater than isomer IVD or its salt.

In yet another embodiment, the mixture comprises isomers IVC and IVD or the pharmaceutically acceptable salts thereof, wherein the isomer IVD or its salt is present in an amount greater than isomer IVC or its salt.

In one embodiment, the mixture comprises isomers IVA, IVB, IVC, and IVD or the pharmaceutically acceptable salts thereof.

In another embodiment, the mixture comprises isomers IVA, IVB, IVC, and IVD or the pharmaceutically acceptable salts thereof, wherein the isomers IVC and IVD, or the salts thereof, together are present in an amount greater than isomers IVA and IVB together or the salts thereof.

In another embodiment, the invention is a compound of Formula V (oxycodone 1,3-butanediol ketal).

In another embodiment, compounds of the present invention are isomers of Formula VA, VB, VC or VD:

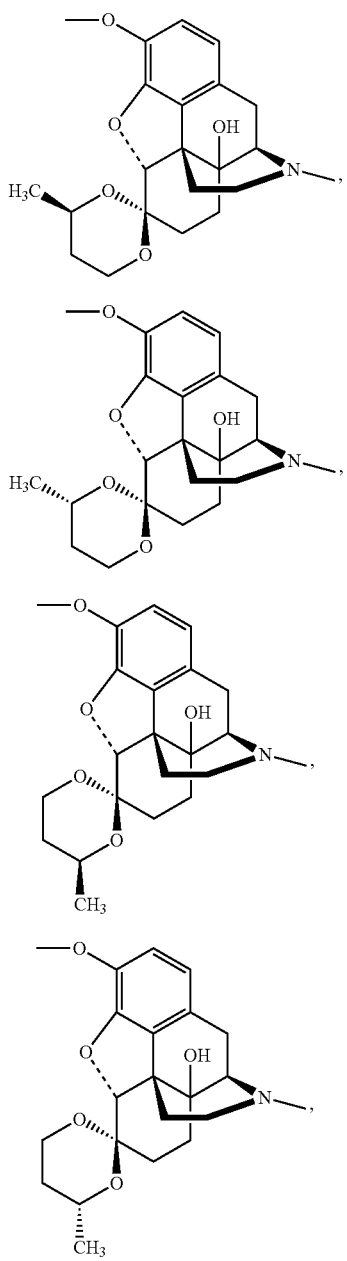

and the pharmaceutically acceptable salts thereof.

In one embodiment, the compound is isomer VA or a pharmaceutically acceptable salt thereof.

In another embodiment, the compound is isomer VB or a pharmaceutically acceptable salt thereof.

In another embodiment, the compound is isomer VC or a pharmaceutically acceptable salt thereof.

In another embodiment, the compound is isomer VD or a pharmaceutically acceptable salt thereof.

In one embodiment, the invention is a mixture, comprising at least two isomers of a compound of Formula V selected from the group consisting of VA, VB, VC and VD, or their pharmaceutically acceptable salts.

In one embodiment, the mixture comprises isomers VA and VB, or their pharmaceutically acceptable salts.

In another embodiment, the mixture comprises isomers VA and VC, or their pharmaceutically acceptable salts.

In another embodiment, the mixture comprises isomers VA and VD, or their pharmaceutically acceptable salts.

In another embodiment, the mixture comprises isomers VB and VC, or their pharmaceutically acceptable salts.

In another embodiment, the mixture comprises isomers VB and VD, or their pharmaceutically acceptable salts.

In another embodiment, the mixture comprises isomers VC and VD, or their pharmaceutically acceptable salts.

In one embodiment, the mixture comprises isomers VA, VB, VC and VD, or their pharmaceutically acceptable salts.

Methods of Preparation

Compounds of Formula I, Formula II, and Formula III can be prepared using methods known to those skilled in the art in view of the present disclosure. For example, compounds of Formula I can be prepared as shown in Scheme 1 by reacting an opioid with a diol, optionally in the presence of an acid catalyst and optionally in the presence of a solvent:

Scheme 1

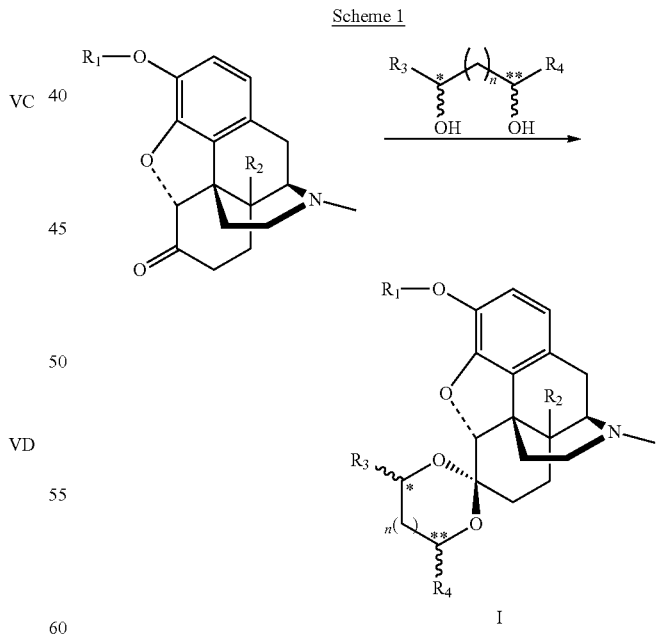

In one embodiment, hydrocodone is reacted with 2,4-pentanediol to prepare a mixture of stereoisomers of hydrocodone 2,4-pentanediol ketal. In another embodiment, hydrocodone is reacted with 2R,4R-pentanediol to prepare the hydrocodone 2,4-pentanediol ketal in which the carbon atom labeled * and the carbon atom labeled ** are both in the R configuration. In another embodiment, hydrocodone is reacted with 2S,4S-pentanediol to provide the hydrocodone 2,4-pentanediol ketal in which the carbon atom labeled * and the carbon atom labeled ** are both in the S configuration. In yet another embodiment, a mixture of isomers is prepared by reacting hydrocodone with meso 2,4-pentanediol to produce a mixture of stereoisomers of hydrocodone 2,4-pentanediol ketal, in which one stereoisomer is a compound wherein the carbon atom labeled * is in the R configuration and the carbon atom labeled ** is in the S configuration, and the other stereoisomer is a compound wherein the carbon atom labeled * is in the S configuration and the carbon atom labeled ** is in the R configuration.

In one embodiment, oxycodone is reacted with 2,5-hexanediol to prepare a mixture of stereoisomers of oxycodone 2,5-hexanediol ketal. In another embodiment, oxycodone is reacted with 2R,5R-hexanediol to prepare the oxycodone 2,5-hexanediol ketal in which the carbon atom labeled * and the carbon atom labeled ** are both in the R configuration. In another embodiment, oxycodone is reacted with 2S,5S-hexanediol to provide the oxycodone 2,5-hexanediol ketal in which the carbon atom labeled * and the carbon atom labeled ** are both in the S configuration. In yet another embodiment, a mixture of isomers is prepared by reacting oxycodone with meso 2,5-hexanediol to produce a mixture of stereoisomers of oxycodone 2,5-hexanediol ketal, in which one stereoisomer is a compound wherein the carbon atom labeled * is in the R configuration and the carbon atom labeled ** is in the S configuration, and the other stereoisomer is a compound wherein the carbon atom labeled * is in the S configuration and the carbon atom labeled ** is in the R configuration.

In one embodiment, hydrocodone is reacted with 2,5-hexanediol to prepare a mixture of stereoisomers of hydrocodone 2,5-hexanediol ketal. In another embodiment, hydrocodone is reacted with 2R,5R-hexanediol to prepare the hydrocodone 2,5-hexanediol ketal in which the carbon atom labeled * and the carbon atom labeled ** are both in the R configuration. In another embodiment, hydrocodone is reacted with 2S,5S-hexanediol to provide the hydrocodone 2,5-hexanediol ketal in which the carbon atom labeled * and the carbon atom labeled ** are both in the S configuration. In yet another embodiment, a mixture of isomers is prepared by reacting hydrocodone with meso 2,5-hexanediol to produce a mixture of stereoisomers of hydrocodone 2,5-hexanediol ketal in which one stereoisomer is a compound wherein the carbon atom labeled * is in the R configuration and the carbon atom labeled ** is in the S configuration, and the other stereoisomer is a compound wherein the carbon atom labeled * is in the S configuration and the carbon atom labeled ** is in the R configuration.

In one embodiment, hydromorphone is reacted with 2,4-pentanediol to prepare a mixture of stereoisomers of hydromorphone 2,4-pentanediol ketal. In another embodiment, hydromorphone is reacted with 2R,4R-pentanediol to prepare the hydromorphone 2,4-pentanediol ketal in which the carbon atom labeled * and the carbon atom labeled ** are both in the R configuration. In another embodiment, hydromorphone is reacted with 2S,4S-pentanediol to provide the hydromorphone 2,4-pentanediol ketal in which the carbon atom labeled * and the carbon atom labeled ** are both in the S configuration. In yet another embodiment, a mixture of isomers is prepared by reacting hydromorphone with meso 2,4-pentanediol to produce a mixture of stereoisomers of hydromorphone 2,4-pentanediol ketal. in which one stereoisomer is a compound wherein the carbon atom labeled * is in the R configuration and the carbon atom labeled ** is in the S configuration, and the other stereoisomer is a compound wherein the carbon atom labeled * is in the S configuration and the carbon atom labeled ** is in the R configuration.

In one embodiment, oxycodone is reacted with 3,5-octanediol to prepare a mixture of stereoisomers of oxycodone 3,5-octanediol ketal.

In one embodiment, oxycodone is reacted with 1,2-cyclohexanediol to prepare a mixture of stereoisomers of oxycodone 1,2-cyclohexanediol ketal. In another embodiment, oxycodone is reacted with cis-1,2-cyclohexanediol to prepare the oxycodone cis-1,2-cyclohexanediol ketal. In another embodiment, oxycodone is reacted with trans-1,2-cyclohexanediol to provide the oxycodone trans-1,2-cyclohexanediol ketal.

In another embodiment, an opioid such as oxycodone, hydrocodone, or hydromorphone is reacted with ethylene glycol or 1,2-propanediol to prepare the ethyleneglycol ketal or a mixture of stereoisomers of the propanediol ketal, respectively.

A further embodiment of the present invention is a process for preparing a compound of Formula II, as shown in Scheme 2, comprising reacting oxycodone with 2,2-dimethyl-1,3-propanediol, optionally in the presence of an acid catalyst and optionally in the presence of a solvent to produce a compound of Formula II.

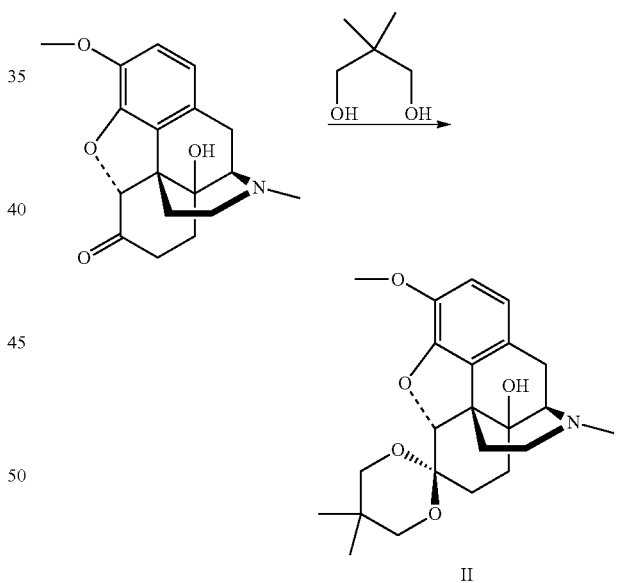

A further embodiment of the present invention is a process for preparing a compound of Formula III, as shown in Scheme 3, comprising reacting oxycodone with 1,2-cyclohexanedimethanol to prepare a mixture of stereoisomers of oxycodone 1,2-cyclohexanedimethanol ketal. In another embodiment, oxycodone is reacted with cis-1,2-cyclohexanedimethanol to prepare the oxycodone cis-1,2-cyclohexanedimethanol ketal. In another embodiment, oxycodone is reacted with trans-1,2-cyclohexanedimethanol to prepare the oxycodone trans-1,2-cyclohexanedimethanol ketal.

Scheme 3

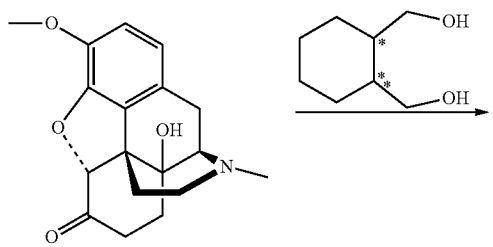

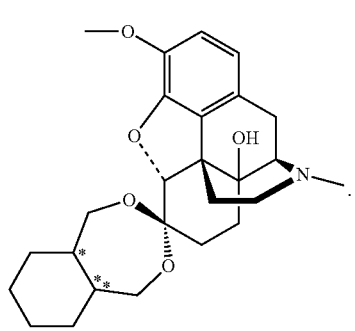

In one embodiment, a mixture of at least two isomers of Formula I or a mixture of at least two isomers of Formula III are resolved using techniques known in the art in view of this disclosure. Such techniques include, but are not limited to chromatographic methods such as silica gel chromatography, reversed phase chromatography, ion-exchange chromatography, hydrophobic interaction chromatography, size exclusion chromatography, affinity chromatography, and combinations thereof, as well as filtration methods and precipitation methods. In a particular embodiment, isomers of Formula I are resolved using preparative HPLC.

In another embodiment, compounds of Formula IV and Formula V can be prepared using methods known to those skilled in the art in view of the present disclosure. For example, compounds of Formula IV can be prepared by reacting oxycodone with 2,4-pentanediol, optionally in the presence of an acid catalyst and optionally in the presence of a solvent to produce a compound of Formula IV, as shown in Scheme 4:

Scheme 4

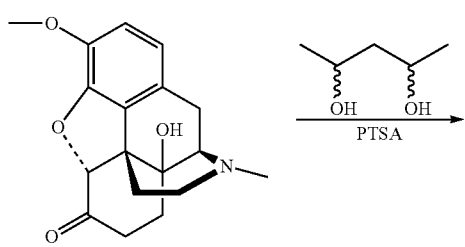

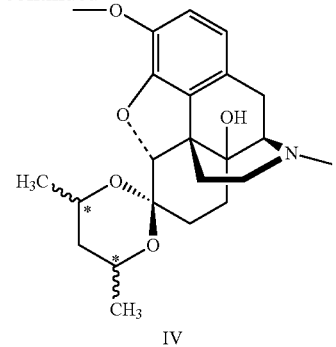

IV

In one embodiment, the reaction of oxycodone with 2,4-pentanediol results in a mixture of isomers IVA, IVB, IVC, and IVD.

In one embodiment, isomer IVD can be prepared by reacting 2R,4R-pentanediol with oxycodone, optionally in the presence of an acid catalyst and optionally in the presence of a solvent to produce isomer IVD. In another embodiment, isomer IVC can be prepared by reacting oxycodone with 2S,4S-pentanediol, optionally in the presence of an acid catalyst and optionally in the presence of a solvent to produce isomer IVC. In yet another embodiment, a mixture of isomers IVA and IVB can be prepared by reacting oxycodone with meso 2,4-pentanediol, optionally in the presence of an acid catalyst and optionally in the presence of a solvent to produce a mixture of isomers IVA and IVB. In yet another embodiment, isomer IVA, IVB, IVC, or IVD can be prepared by resolving a mixture of enantiomers or diastereomers using techniques commonly known in the art in view of this disclosure.

A further embodiment of the present invention is a process for preparing a compound of Formula V comprising reacting oxycodone with 1,3-butanediol, optionally in the presence of an acid catalyst and optionally in the presence of a solvent to produce a compound of Formula V (oxycodone 1,3-butanediol ketal) as shown in Scheme 5.

Scheme 5

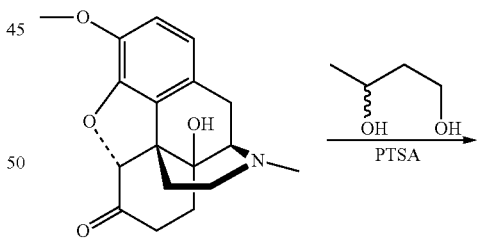

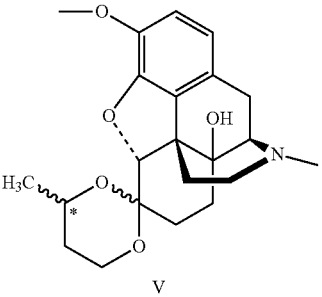

V

In one embodiment, isomers VA and VD can be prepared by reacting (R)-1,3-butanediol with oxycodone, optionally in the presence of an acid catalyst and optionally in the presence of a solvent to produce isomers VA and VD. In one embodiment, isomers VB and VC can be prepared by reacting (S)-1,3-butanediol with oxycodone, optionally in the presence of an acid catalyst and optionally in the presence of a solvent to produce isomers VB and VC. In yet another embodiment, isomer VA, VB, VC or VD can be prepared by resolving a mixture of enantiomers or diastereomers using techniques commonly known in the art in view of this disclosure.

In one embodiment, a mixture of at least two isomers of Formula IV or a mixture of at least two isomers of Formula V are resolved using techniques known in the art in view of this disclosure. Such techniques include, but are not limited to chromatographic methods such as silica gel chromatography, reversed phase chromatography, ion-exchange chromatography, hydrophobic interaction chromatography, size exclusion chromatography, affinity chromatography, and combinations thereof, as well as filtration methods and precipitation methods. In a particular embodiment, isomers of Formula IV or isomers of Formula V are resolved using preparative HPLC.

In some non-limiting embodiments, the diols used to prepare compounds of Formula I, Formula II, Formula III, Formula IV, or Formula V is obtained commercially. In some non-limiting embodiments, the diols used to prepare compounds of Formula I, Formula II, Formula III, Formula IV, or Formula V are prepared using methods commonly known to persons of ordinary skill in the art.

In some non-limiting embodiments, the compounds of Formula I, Formula II, Formula III, Formula IV, or Formula V are converted to their salts using techniques commonly known to a person of ordinary skill in the art. In other embodiments, the salt is a pharmaceutically acceptable salt.

In some non-limiting embodiments, the reaction to prepare compounds of Formula I, Formula II, Formula III, Formula IV, or Formula V occurs in a non-polar solvent. In some non-limiting embodiments, the solvent is pentane, cyclopentane, hexane, cyclohexane, benzene, toluene, xylene, 1,4-dioxane, chloroform, diethylether, dichloromethane, tetrahydrofuran, dimethyl sulfoxide, carbon tetrachloride, pyridine, dimethylfuran, or a mixture thereof. In some embodiments, the solvent is toluene.

In some non-limiting embodiments, the acid catalyst used in the reaction to prepare compounds of Formula I, Formula II, Formula III, Formula IV, or Formula V is a sulfonic acid. In some embodiments, the acid catalyst is methanesulfonic acid, ethanesulfonic acid, benzenesulfonic acid, naphthalenesulfonic acid, p-toluenesulfonic acid ("PTSA"), ethanedisulfonic acid, propanedisulfonic acid, naphthalene-1,5-disulfonic acid, or a mixture thereof. In some embodiments, the acid catalyst is PTSA.

In some non-limiting embodiments, the reaction to prepare compounds of Formula I, Formula II, Formula III, Formula IV, or Formula V occurs with the removal of water using azeotropic distillation. In some embodiments, the water is removed using molecular sieves or aluminum oxide.

In some non-limiting embodiments, the ratio of the acid catalyst to the opioid in the reaction on a molar basis is about 0.5:1, about 0.6:1, about 0.7:1, about 0.8:1, about 0.9:1, about 1:1, about 1.1:1, about 1.2:1, about 1.3:1, about 1.4:1, about 1.5:1, about 1.6:1, about 1.7:1, about 1.8:1, about 1.9:1, about 2:1, about 2.5:1, about 3:1, about 4:1, or about 5:1. In some embodiments, the ratio of the acid catalyst to the oxycodone in the reaction ranges from about 1:1 to about 1.5:1. In some embodiments, the ratio of the acid catalyst to the oxycodone in the reaction is about 1.2:1.

In other embodiments, the ratio of the opioid to the diol in the reaction on a molar basis is about 1:1, about 1:1.05, about 1:1.1, about 1:1.2, about 1:1.3, about 1:1.5, about 1:2, about 1:2.5, about 1:3, about 1:4, about 1:5, about 1:10, about 1:20, about 1:30, about 1:40, about 1:50, or about 1:100.

In other embodiments, the reaction to prepare compounds of the invention is carried out under conditions of refluxing toluene. In one embodiment, the reaction is carried out under refluxing xylene. In another embodiment, the reaction is carried out at about 70° C., about 80° C., about 90° C., about 100° C., about 110° C., about 120° C., or about 130° C.

In another embodiment, the reaction is carried out for a time period of from about 3 hours to about 24 hours. In a particular embodiment, the reaction is carried out for about 3.5 hours.

Administration of Compounds of the Invention

Compounds of Formula I, Formula II, Formula III, Formula IV, and Formula V can act as prodrugs and thereby exhibit one or more advantages over the parent opioid drug. For example, compounds of Formula I. Formula II, Formula III, Formula IV, and Formula V can be used to prevent accidental overdose by exhibiting a delayed onset of pharmacological activity when inadvertently orally administered at higher than the prescribed dose. In some embodiments, compounds of Formula I, Formula II, Formula III, Formula IV, and Formula V can hinder abuse by substantially maintaining their chemical form as prodrugs when administered by non-oral routes (e.g., parenteral) likely to be employed by abusers. Thus, compounds of Formula I, Formula II, Formula III, Formula IV, and Formula V can hinder abuse by reducing availability of the active opioid molecule when administered via parenteral routes, particularly the intravenous, intranasal, and/or inhalation routes that are often employed in illicit use.

In some embodiments, compounds of Formula I, Formula II, Formula III, Formula IV, and Formula V have no affinity, or have reduced affinity, for the µ opioid receptor as compared to that of the parent opioid. Compounds of Formula I, Formula II, Formula III, Formula IV, and Formula V can be converted from the prodrug form to the parent opioid under the acid conditions of the stomach. Gradual conversion of a compound of Formula I, Formula II, Formula III, Formula IV, or Formula V to the parent opioid when administered orally to a mammal should result in gradual but delayed systemic exposure to the parent opioid, as compared to direct oral administration of the parent opioid.

An opioid prodrug that provides a gradual conversion to the parent opioid can be less attractive to substance abusers or non-medical recreational users of opioids who seek drugs to provide rapid euphoria. As conversion from a compound of Formula I, Formula II, Formula III, Formula IV, or Formula V to the parent opioid will be slower, the onset of euphoria will likewise be slower, thereby resulting in compounds of the invention appearing less attractive to those who would attempt such non-medical usage of the drug.

In many cases, opioid abuse by the oral route involves immediate release drugs, or drugs in which controlled release materials used to delay the liberation and absorption of the opioid from the dosage form have been tampered with. Immediate release opioids generally provide pharmacologically relevant plasma concentrations, onset of therapeutic effects and, in the case of recreational drug users, onset of euphoria, within about 15 to 180 minutes, 15 to 120 minutes, or 15 to 90 minutes after oral administration.

The gradual conversion of compounds of the invention to the parent opioid in the GI tract may serve to delay, and therefore reduce, any euphoric effects otherwise produced by opioids by delaying the time to reach pharmacologically relevant plasma concentrations of oxycodone, e.g., by providing a lower $C_{max}$ and/or a later $T_{max}$ than oral, immediate release forms of opioids. Consequently, in some embodiments, dosage forms of the present invention will have a lower potential for abuse and misuse.

Compounds of Formula I, Formula II, Formula III, Formula IV, and Formula V can exhibit extended release characteristics. For example, a compound of the invention can provide a slow conversion to the parent opioid when administered orally. FIG. 1 presents the release profile of oxycodone from a mixture of isomers of oxycodone 2,4 pentanediol ketals by hydrolysis with 0.1 N HCl at 37° C., which simulates the acidic conditions in the human stomach. FIG. 1 also presents the release profile of oxycodone from a mixture of isomers of oxycodone 2,4 pentanediol ketals by hydrolysis in Simulated Gastric Fluid (SGF) (0.2% NaCl and 0.32% pepsin in 0.084 N HCl) at 37° C. As shown, two of the ketal isomers, Ketal C and Ketal D, undergo nearly complete hydrolysis in four hours in both 0.1 N HCl and SGF. FIG. 1 shows that different isomers exhibit different hydrolysis rates, enabling specific controlled release profiles of the parent oxycodone to be created by specifically adjusting the isomer ratios.

Figure 2:
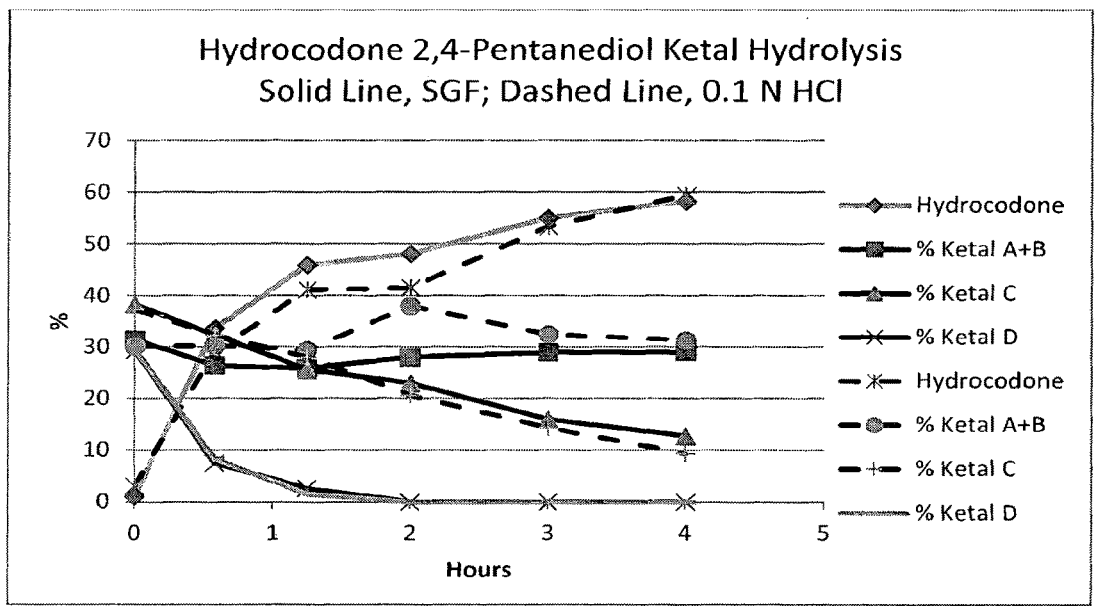
FIG. 2 is a graph of the hydrolysis of a mixture of four isomers of hydrocodone 2,4-pentanediol ketal using SGF or 0.1 N HCl at 37° C. and the release of hydrocodone.

FIG. 2 shows the hydrolysis of isomers of hydrocodone 2,4-pentanediol ketals in 0.1 N HCl at 37° C. or SGF, respectively. As shown, different isomers exhibit different hydrolysis rates, enabling specific controlled release profiles of the parent hydrocodone to be created by specifically adjusting isomer ratios.

Figure 3:
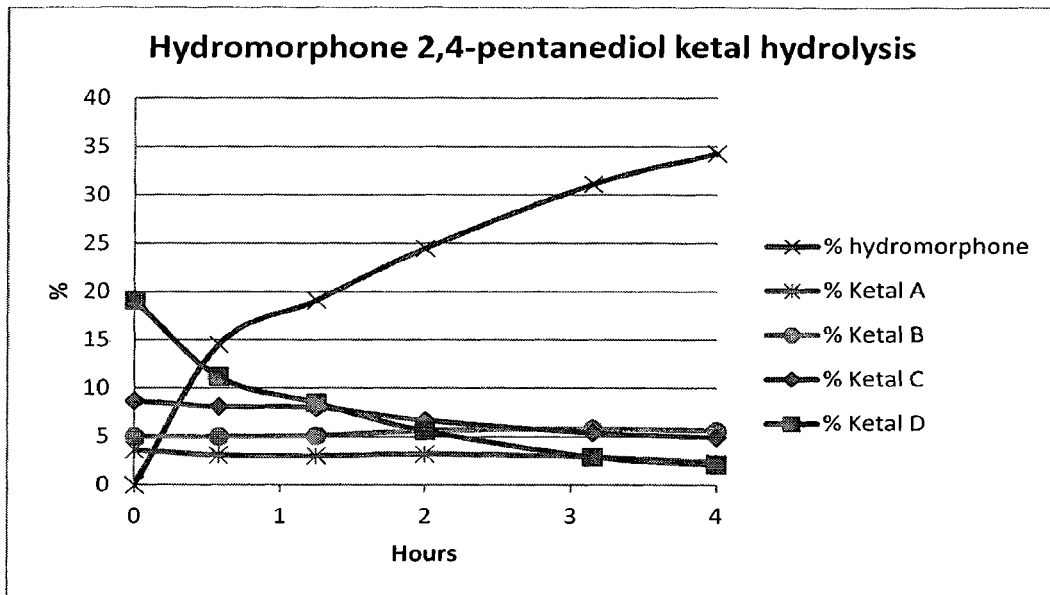
FIG. 3 is a graph of the hydrolysis of a mixture of four isomers of hydromorphone 2,4 pentanediol ketal using 0.1 N HCl at 37° C., and the release of hydromorphone.

FIG. 3 presents the release profile of hydromorphone from a mixture of four isomers of hydromorphone 2,4 pentanediol ketals by hydrolysis with 0.1 N HCl at 37° C. As shown, one of the ketal isomers, Ketal D, undergoes nearly complete hydrolysis in four hours in 0.1 N HCl. Thus, FIG. 3 shows that different isomers exhibit different hydrolysis rates, enabling specific controlled release profiles of hydromorphone to be created by specifically adjusting isomer ratios.

Figure 4:
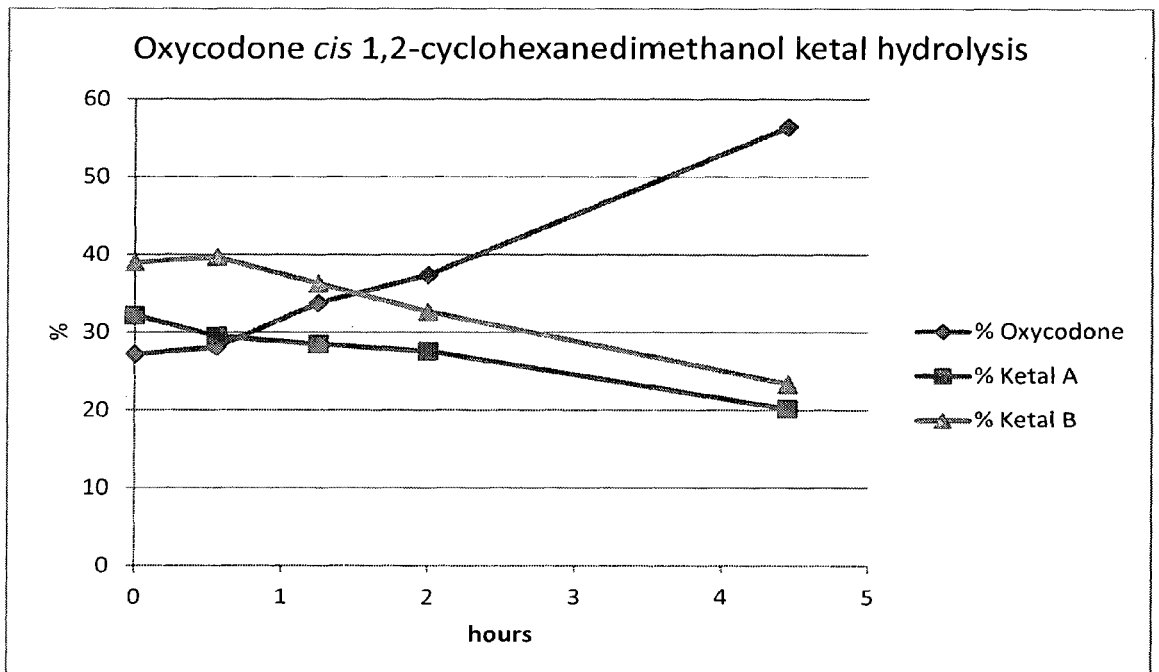
FIG. 4 is a graph of the hydrolysis of a mixture of isomers of oxycodone cis 1,2-cyclohexancdimethanol ketals in 0.1 N HCl at 37° C., and the release of oxycodone.

FIG. 4 presents the release profile of oxycodone from a mixture of isomers of oxycodone cis 1,2-cyclohexanedimethanol ketals in 0.1 N HCl at 37° C. As shown, the proportion of oxycodone in the mixture increased from about 30% to about 55% within five hours.

Figure 5:
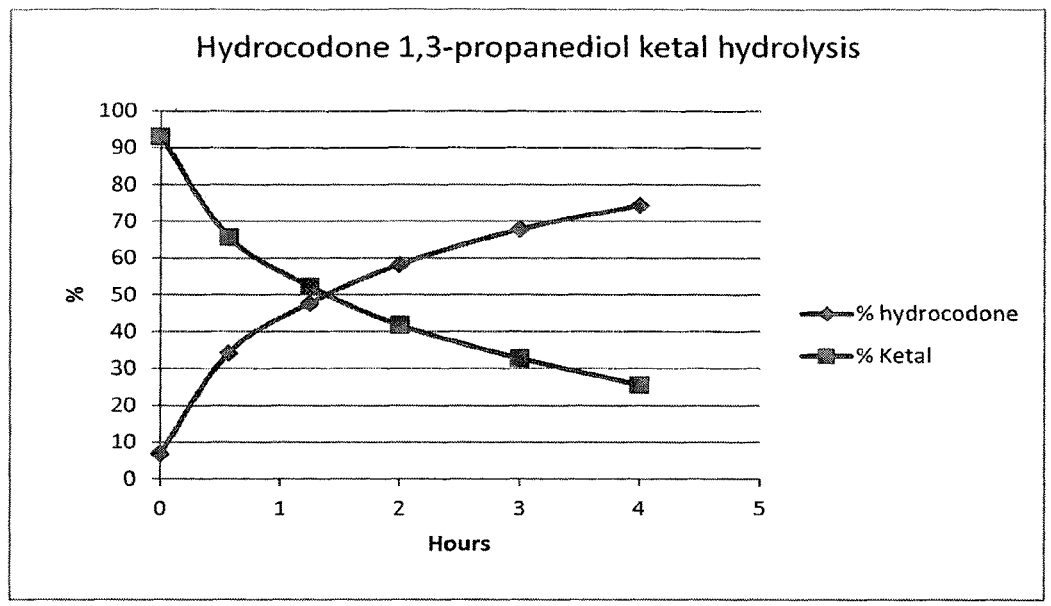
FIG. 5 is a graph of the hydrolysis of hydrocodone 1,3-propanediol ketal in 0.1 N HCl at 37° C. and the release of hydrocodone.
Figure 6:
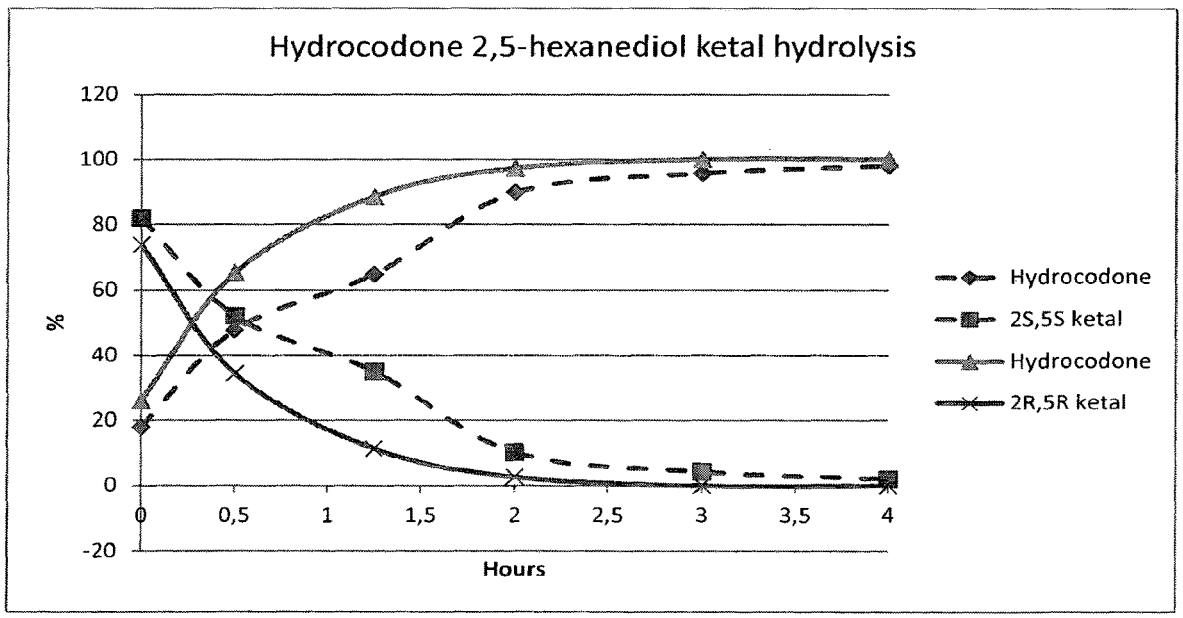
FIG. 6 is a graph of the hydrolysis of hydrocodone 2R,5R-hexanediol ketal and hydrocodone 2S,5S-hexanediol ketal in 0.1 N HCl at 37° C. and the release of hydrocodone.

FIG. 5 and FIG. 6 present the release profile of hydrocodone from hydrocodone 1,3-propanediol ketal and hydrocodone 2,5-hexanediol ketal, respectively. In both cases, the ketal compound undergoes nearly complete hydrolysis to hydrocodone in about 4 hours, permitting controlled release of hydrocodone in a subject by adjusting isomer ratios.

Figure 9:
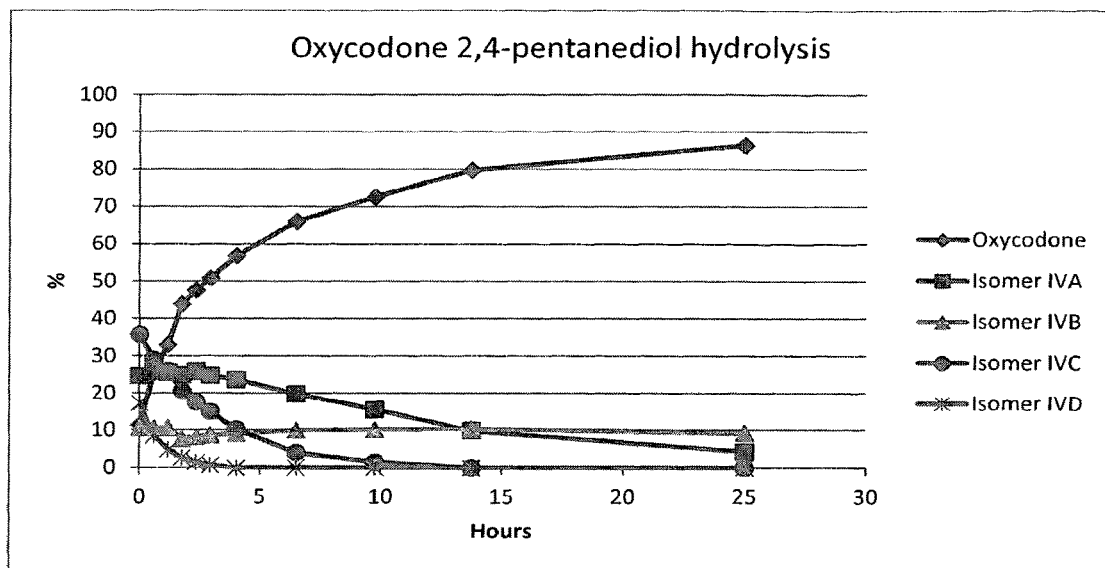
FIG. 9 is a graph of the hydrolysis of a mixture of four isomers of compound of Formula IV (IVA-IVD) using 0.1 N HCl at 37° C. and the release of oxycodone.
Figure 10:
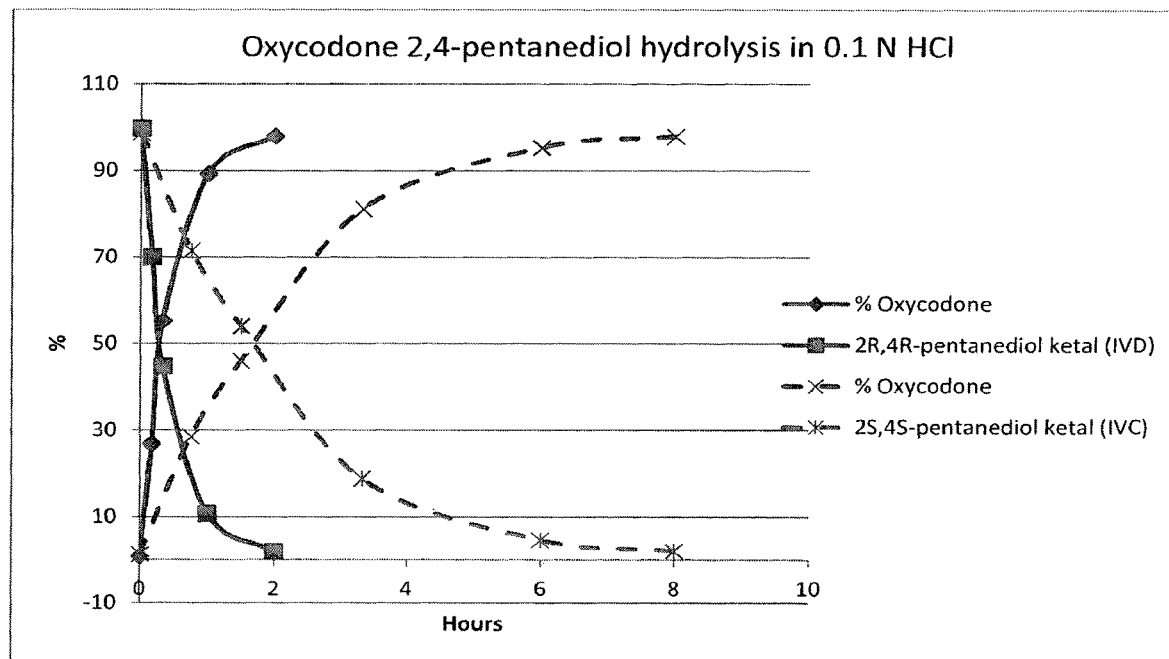
FIG. 10 is a graph of the hydrolysis of isomers IVC and IVD using 0.1 N HCl at 37° C. and the release of oxycodone.

FIG. 9 presents the release profile of oxycodone from a mixture of isomers of Formula IV (isomers IVA-IVD) by hydrolysis with 0.1 N HCl at 37° C. As shown, about 50% of the oxycodone is released in about 2.9 hours, with almost 90% oxycodone release occurring no later than about 25 hours. FIG. 10 shows the hydrolysis of isomers IVC and IVD using 0.1N HCl at 37° C. Isomer IVC appears to be almost completely hydrolyzed within 8 hours. Isomer IVD appears to be almost completely hydrolyzed within 2 hours.

Figure 11:
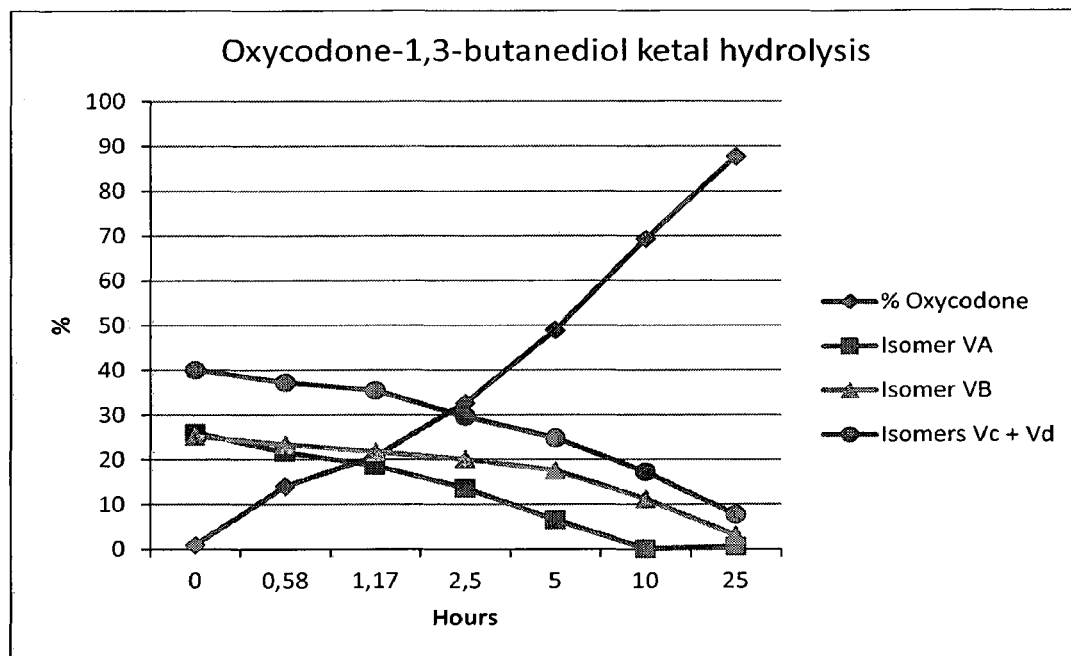
FIG. 11 is a graph of the hydrolysis of a mixture of four isomers of the compound of Formula V using 0.1 N HCl at 37° C., and the release of oxycodone. The stereochemistry of each of the isomers of Formula V remains to be assigned.

FIG. 11 presents the release profile of oxycodone from a mixture of four isomers of Formula V by hydrolysis with 0.1 N HCl at 37° C. As shown, about 50% of the oxycodone is released at about 5 hours, with about 90% release occurring no later than about 25 hours.

An extended release formulation prevents rapid onset of pharmacological effects, and is formulated in such a manner as to make the contained medication available over an extended period of time. In some embodiments, a compound of Formula I, Formula II, Formula III, Formula IV, or Formula V can achieve an extended release profile simply based on the fact that it requires conversion to the parent opioid. Thus, in one embodiment, compounds of the invention can be formulated without use of controlled release excipients, yet still result in an extended release of opioid upon oral administration.

Compounds of the invention can be pharmaceutically formulated to further enhance an extended release profile, for example, by formulating the compound(s) in a dosage form comprising a sustained release matrix or a sustained release coating, or some variation thereof. Controlled release formulation technology is well-known in the art, and can be used in conjunction with the present invention to obtain particularly desirable release profiles. In some embodiments, both the parent opioid and the compound(s) of the invention can be combined into a single oral dosage form, where the opioid provides an immediate release profile and the compound(s) of the invention effectively provides an extended release profile of oxycodone. Such combination formulations may or may not further comprise a sustained release matrix or a sustained release coating, or some variation thereof.

In one embodiment, two or more stereoisomers of one or more compounds of the invention are mixed in varying proportions to control the in vivo and/or in vitro release profile of the parent opioid. It has been shown that the different stereoisomers hydrolyze at different rates, thereby releasing the parent opioid in a controlled manner. Thus, a number of possibilities exist for controlling release of the parent opioid by employing combinations and amounts of two or more stereoisomers, wherein each stereoisomer hydrolyzes at a different rate in vitro and/or in vivo. For example, oxycodone 2R,4R-pentanediol ketal, a stereoisomer that hydrolyzes relatively quickly can be provided in a mixture with oxycodone 2S,4S-pentanediol ketal, a stereoisomer that hydrolyzes relatively slowly. These two stereoisomers can then be provided in different concentrations and in different proportions to one another to achieve a desired release pattern of the parent opioid. In another non-limiting example, hydrocodone 2R,5R-hexanediol ketal, a stereoisomer that hydrolyzes relatively quickly can be provided in a mixture with hydrocodone 2S,4S-hexanediol ketal, a stereoisomer that hydrolyzes relatively slowly.

In one embodiment, the present invention provides a method of decreasing the abuse potential of an opioid in a mammal in need of opioid therapy, the method comprising orally administering to the mammal an effective amount of a compound of Formula I, Formula II, Formula III, Formula IV, or Formula V, which exhibits a decreased parenteral (i.e., non-oral) bioavailability compared to the parent opioid. In another embodiment, the present invention provides a method of decreasing the abuse potential of an opioid in a mammal in need of opioid therapy, the method comprising orally administering to the mammal an effective amount of a mixture of two or more stereoisomers of a compound of Formula I or a salt thereof. In some embodiments, the method comprises orally administering to the mammal a mixture of two stereoisomers of a compound of Formula I at a ratio of about 5:95, about 10:90, about 15:85, about 20:80, about 25:75, about 30:70, about 35:65, about 40:60, about 45:55, or about 50:50. In another embodiment, the present invention provides a method of decreasing the abuse potential of an opioid in a mammal in need of opioid therapy, the method comprising orally administering to the mammal an effective amount of a compound of Formula II or a salt thereof. In another embodiment, the present invention provides a method of decreasing the abuse potential of an opioid in a mammal in need of opioid therapy, the method comprising orally administering to the mammal an effective amount of a mixture of at least two or more stereoisomers of a compound of Formula III or a salt thereof.

In one embodiment, the present invention provides a method of decreasing the abuse potential of hydrocodone in a mammal in need of hydrocodone therapy, the method comprising orally administering to the mammal an effective amount of a mixture comprising two or more stereoisomers of hydrocodone 2,4-pentanediol ketal, or pharmaceutically acceptable salts thereof, wherein in the compound of Formula I, $R_1$ is $CH_3$, $R_2$ is H, n is 1, and $R_3$ and $R_4$ are each $CH_3$. In one embodiment, the method comprises administering a mixture of stereoisomers of hydrocodone 2,4-pentanediol ketal, or pharmaceutically acceptable salts thereof, wherein in some stereoisomers, the carbon atom labeled * and the carbon atom labeled ** are in the RR configuration and in other stereoisomers the carbon atoms labeled * and the carbon atom labeled ** are in the SS configuration. In another embodiment, the method comprises administering a mixture of stereoisomers of hydrocodone 2,4-pentanediol ketal, or pharmaceutically acceptable salts thereof, wherein the carbon atom labeled * is in the R configuration and the carbon atom labeled ** is in the S configuration. In another embodiment, the method comprises administering a mixture of stereoisomers of hydrocodone 2,4-pentanediol ketal, or pharmaceutically acceptable salts thereof, in which the carbon atom labeled * is in the S configuration and the carbon atom labeled ** is in the R configuration. In some embodiments, the method comprises orally administering to the mammal a mixture of two stereoisomers of hydrocodone 2,4-pentanediol ketal at a ratio of about 5:95, about 10:90, about 15:85, about 20:80, about 25:75, about 30:70, about 35:65, about 40:60, about 45:55, or about 50:50.

In one embodiment, the present invention provides a method of decreasing the abuse potential of oxycodone in a mammal in need of oxycodone therapy, the method comprising orally administering to the mammal an effective amount of a mixture comprising two or more stereoisomers of oxycodone 2,5-hexanediol ketal, or pharmaceutically acceptable salts thereof, wherein in the compound of Formula I, $R_1$ is $CH_3$, $R_2$ is OH, n is 2, and $R_3$ and $R_4$ are each $CH_3$. In one embodiment, the method comprises administering a mixture of stereoisomers of oxycodone 2,5-hexanediol ketal, or pharmaceutically acceptable salts thereof, wherein in some stereoisomers the carbon atom labeled * and the carbon atom labeled ** are in the RR configuration and in other stereoisomers the carbon atom labeled * and the carbon atom labeled ** are in the SS configuration. In another embodiment, the method comprises administering a mixture of stereoisomers of oxycodone 2,5-hexanediol ketal, or pharmaceutically acceptable salts thereof, wherein the carbon atom labeled * is in the R configuration and the carbon atom labeled ** is in the S configuration. In another embodiment, the method comprises administering a mixture of stereoisomers of oxycodone 2,5-hexanediol ketal, or pharmaceutically acceptable salts thereof, wherein the carbon atom labeled * is in the S configuration and the carbon atom labeled ** is in the R configuration. In some embodiments, the method comprises orally administering to the mammal a mixture of two stereoisomers of oxycodone 2,5-hexanediol ketal at a ratio of about 5:95, about 10:90, about 15:85, about 20:80, about 25:75, about 30:70, about 35:65, about 40:60, about 45:55, or about 50:50.

In one embodiment, the present invention provides a method of decreasing the abuse potential of hydrocodone in a mammal in need of hydrocodone therapy, the method comprising orally administering to the mammal an effective amount of a mixture comprising two or more stereoisomers of hydrocodone 2,5-hexanediol ketal, or pharmaceutically acceptable salts thereof, wherein $R_1$ is $CH_3$, $R_2$ is H, n is 2, and $R_3$ and $R_4$ are each $CH_3$. In one embodiment, the method comprises administering a mixture of stereoisomers of hydrocodone 2,5-hexanediol ketal, or pharmaceutically acceptable salts thereof, wherein in some stereoisomers the carbon atom labeled * and the carbon atom labeled ** are in the RR configuration and in other stereoisomers the carbon atoms labeled * and the carbon atom labeled ** are in the SS configuration. In another embodiment, the method comprises administering a mixture of stereoisomers of hydrocodone 2,5-hexanediol ketal, or pharmaceutically acceptable salts thereof, wherein the carbon atom labeled * is in the R configuration and the carbon atom labeled ** is in the S configuration. In another embodiment, the method comprises administering a mixture of stereoisomers of hydrocodone 2,5-hexanediol ketal, or pharmaceutically acceptable salts thereof, wherein the carbon atom labeled * is in the S configuration and the carbon atom labeled ** is in the R configuration. In some embodiments, the method comprises orally administering to the mammal a mixture of two stereoisomers of hydrocodone 2,5-hexanediol ketal at a ratio of about 5:95, about 10:90, about 15:85, about 20:80, about 25:75, about 30:70, about 35:65, about 40:60, about 45:55, or about 50:50.

In one embodiment, the present invention provides a method of decreasing the abuse potential of hydromorphone in a mammal in need of hydromorphone therapy, the method comprising orally administering to the mammal an effective amount of a mixture comprising two or more stereoisomers of hydromorphone 2,4-pentanediol ketal, or pharmaceutically acceptable salts thereof, wherein $R_1$ is H, $R_2$ is H, n is 1, and $R_3$ and $R_4$ are each $CH_3$. In one embodiment, the method comprises administering a mixture of stereoisomers of hydromorphone 2,4-pentanediol ketal, or pharmaceutically acceptable salts thereof, wherein in some stereoisomers the carbon atom labeled * and the carbon atom labeled ** are in the RR configuration and in other stereoisomers the carbon atoms labeled * and ** are in the SS configuration. In another embodiment, the method comprises administering a mixture of stereoisomers of hydromorphone 2,4-pentanediol ketal, or pharmaceutically acceptable salts thereof, wherein the carbon atom labeled * is in the R configuration and the carbon atom labeled ** is in the S configuration. In another embodiment, the method comprises administering a mixture of stereoisomers of hydromorphone 2,4-pentanediol ketal, or pharmaceutically acceptable salts thereof, wherein the carbon atom labeled * is in the S configuration and the carbon atom labeled ** is in the R configuration. In some embodiments, the method comprises orally administering to the mammal a mixture of two stereoisomers of hydromorphone 2,4-pentanediol ketal at a ratio of about 5:95, about 10:90, about 15:85, about 20:80, about 25:75, about 30:70, about 35:65, about 40:60, about 45:55, or about 50:50.

In one embodiment, the present invention provides a method of decreasing the abuse potential of oxycodone in a mammal in need of oxycodone therapy, the method comprising orally administering to the mammal an effective amount of a mixture comprising two or more stereoisomers of oxycodone 1,2-cyclohexanediol ketal, or pharmaceutically acceptable salts thereof. In one embodiment, the method comprises administering a mixture of stereoisomers of oxycodone 1,2-cyclohexanediol ketal, or salts thereof, wherein the carbon atom labeled * and the carbon atom labeled ** are in the cis configuration relative to each other. In another embodiment, the method comprises administering a mixture of stereoisomers of oxycodone 1,2-cyclohexanediol ketal, or salts thereof, wherein the carbon atom labeled * and the carbon atom labeled ** are in the trans configuration relative to each other. In some embodiments, the method comprises orally administering to the mammal a mixture of two stereoisomers of oxycodone 1,2-cyclohexanediol ketal at a ratio of about 5:95, about 10:90, about 15:85, about 20:80, about 25:75, about 30:70, about 35:65, about 40:60, about 45:55, or about 50:50.

In one embodiment, the present invention provides a method of decreasing the abuse potential of oxycodone in a mammal in need of oxycodone therapy, the method comprising orally administering to the mammal an effective amount of a mixture comprising two or more stereoisomers of a compound Formula III, or pharmaceutically acceptable salts thereof. In one embodiment, the method comprises administering a mixture of stereoisomers of a compound of Formula III, or salts thereof, wherein the carbon atoms labeled * are in the cis configuration to each other. In another embodiment, the method comprises administering a mixture of stereoisomers of a compound of Formula III, or salts thereof, wherein the carbon atoms labeled * are in the trans configuration to each other. In some embodiments, the method comprises orally administering to the mammal a mixture of two isomers of a compound of Formula III at a ratio of about 5:95, about 10:90, about 15:85, about 20:80, about 25:75, about 30:70, about 35:65, about 40:60, about 45:55, or about 50:50.

In one embodiment, the present invention provides a method of decreasing the abuse potential of hydrocodone in a mammal in need of hydrocodone therapy, the method comprising orally administering to the mammal an effective amount of hydrocodone 1,3-propanediol ketal, or pharmaceutically acceptable salts thereof.

In one embodiment, the present invention provides a method of decreasing the abuse potential of oxycodone in a mammal in need of oxycodone therapy, the method comprising orally administering to the mammal an effective amount of a compound of Formula IV or Formula V, which exhibits a decreased parenteral (i.e., non-oral) bioavailability compared to oxycodone. In another embodiment, the present invention provides a method of decreasing the abuse potential of oxycodone in a mammal in need of oxycodone therapy, the method comprising orally administering to the mammal an effective amount of a mixture of at least two isomers selected from the group consisting of isomers IVA, IVB, IVC, and IVD. In another embodiment, the present invention provides a method of decreasing the abuse potential of oxycodone in a mammal in need of oxycodone therapy, the method comprising orally administering to the mammal an effective amount of a mixture of at least two isomers selected from the group consisting of isomers VA, VB, VC, and VD.

In one embodiment, the present invention provides a method of decreasing the abuse potential of oxycodone in a mammal in need of oxycodone therapy, the method comprising orally administering to the mammal an effective amount of a mixture comprising isomers IVC and IVD. In another embodiment, the method of decreasing the abuse potential of oxycodone comprises orally administering to the mammal an effective amount of a mixture comprising isomers IVC and IVD, wherein the isomer IVC is present in a molar amount greater than isomer IVD. In yet another embodiment, the method of decreasing the abuse potential of oxycodone comprises administering a mixture comprising isomers IVC and IVD, wherein the isomer IVD is present in a molar amount greater than isomer IVC.

In one embodiment, the method of decreasing the abuse potential of oxycodone comprises orally administering to the mammal an effective amount of a mixture comprising isomers IVA, IVB, IVC, and IVD. In certain embodiments, the isomers IVC and IVD together are present in an aggregate molar amount greater than isomers IVA and IVB together.

In one embodiment, the method of decreasing the abuse potential of an opioid comprises orally administering to the mammal an effective amount of a mixture, comprising at least two compounds selected from the group consisting of stereoisomers of Formula I, Formula II, Formula III, and salts thereof, wherein at least about 10%, at least about 20%, at least about 30%, at least about 40%, or at least about 50% of the aggregate molar amount of isomers is hydrolyzed to the parent opioid at 37° C. in 0.1 N HCl within about 2 hours. In a particular embodiment, the method comprises administering at least two stereoisomers of: hydrocodone 2,4-pentanediol ketal; oxycodone 2,5-hexanediol ketal; hydrocodone 2,5-hexanediol ketal; hydromorphone 2,4-pentanediol ketal; oxycodone 1,2-cyclohexanediol ketal; a compound of Formula III, or salts thereof.

In one embodiment, the invention is a method of decreasing the abuse potential of an opioid comprising orally administering to the mammal an effective amount of a compound of Formula I or a pharmaceutically acceptable salt thereof, with the proviso that the compound is not hydrocodone ethyleneglycol ketal, hydromorphone ethyleneglycol ketal, oxycodone ethyleneglycol ketal, hydrocodone 1,3-propanediol ketal, oxycodone 1,3-propanediol ketal, hydromorphone 1,3-propanediol ketal, or a pharmaceutically acceptable salt thereof. In one embodiment, the method of decreasing the abuse potential of an opioid comprises orally administering to the mammal an effective amount of a mixture comprising at least two compounds selected from the group consisting of stereoisomers of Formula I and the pharmaceutically acceptable salts thereof, with the proviso that the mixture is not a mixture of stereoisomers of hydrocodone 2,3-butanediol ketal, oxycodone 2,3-butanediol ketal, hydrocodone 2,3-butanediol ketal, or any pharmaceutically acceptable salts thereof.

In one embodiment, the invention is a method of decreasing the abuse potential of oxycodone comprising orally administering to the mammal an effective amount of a mixture comprising at least two compounds selected from the group consisting of isomers IVA, IVB, IVC, IVD, VA, VB, VC, and VD and the pharmaceutically acceptable salts thereof, wherein at least about 10%, at least about 20%, at least about 30%, at least about 40%, or at least about 50% of the aggregate molar amount of the isomers are hydrolyzed to oxycodone at 37° C. in 0.1 N HCl within about 2 hours.

In one embodiment, the invention is a method of achieving opioid therapy in a mammal, comprising orally administering to the mammal a therapeutically effective amount of a compound of Formula I, Formula II, or Formula III, or a pharmaceutically acceptable salt thereof, wherein at least about 10%, at least about 20%, at least about 30%, at least about 40%, or at least about 50% of the aggregate molar amount of the compound of Formula I, Formula II, or Formula III, or salt thereof, is hydrolyzed to the parent opioid within about 2 hours at 37° C. in 0.1 N HCl. In a particular embodiment, the method comprises orally administering to the mammal a therapeutically effective amount of a compound of Formula I, Formula II, or Formula III, or pharmaceutically acceptable salt thereof, wherein at least about 10%, at least about 20%, at least about 30%, at least about 40%, at least about 50%, at least about 60%, at least about 70/a, at least about 80%, at least about 90%, or about 100% of the compound of Formula I, Formula II, or Formula III, or pharmaceutically acceptable salt thereof, is hydrolyzed to the parent opioid within about 4 hours at 37° C. in 0.1 N HCl.

In one embodiment, the invention is a method of achieving opioid therapy in a mammal, comprising orally administering an excess of a stereoisomer of hydrocodone 2,4-pentanediol ketal, oxycodone 2,5-hexanediol ketal, hydrocodone 2,5-hexanediol ketal, hydromorphone 2,4-pentanediol ketal, oxycodone 1,2-cyclohexanediol ketal, compound of Formula III, or pharmaceutically acceptable salt thereof, wherein about 80%, about 90%, about 95%, or about 100% of the stereoisomer is hydrolyzed to the parent opioid within about 8 hours at 37° C. in 0.1 N HCl. In particular embodiments, the method comprises orally administering the RR or SS isomer of hydrocodone 2,4-pentanediol ketal; the RR or SS isomer of hydromorphone 2,4-pentanediol ketal; the RR or SS isomer of oxycodone 2,5-hexanediol ketal; the RR or SS isomer of hydrocodone 2,5-hexanediol ketal; hydrocodone 1,3-propanediol ketal; or a pharmaceutically acceptable salt thereof. In each case, the carbon atom labeled * and the carbon atom labeled ** in the compound of Formula I are both in the R configurations or both in the S configurations.

In one embodiment, the invention is a method of achieving opioid therapy in a mammal in need of said therapy, comprising orally administering to the mammal a therapeutically effective amount of a compound of Formula I, or pharmaceutically acceptable salt thereof, with the proviso that the compound is not hydrocodone ethyleneglycol ketal; hydromorphone ethyleneglycol ketal; oxycodone ethyleneglycol ketal; hydrocodone 1,3-propanediol ketal; oxycodone 1,3-propanediol ketal; hydromorphone 1,3-propanediol ketal; or a salt thereof. In one embodiment, the invention is a method of achieving opioid therapy in a mammal in need of said therapy, comprising orally administering to the mammal a therapeutically effective amount of a mixture of stereoisomers of a compound of Formula I, or pharmaceutically acceptable salts thereof, with the proviso that the mixture is not a mixture of stereoisomers of hydrocodone 2,3-butanediol ketal; oxycodone 2,3-butanediol ketal; hydrocodone 2,3-butanediol ketal; or salts thereof.

In another embodiment, the invention is a method of achieving opioid therapy in a mammal in need of said therapy, comprising orally administering to the mammal a therapeutically effective amount of a mixture of isomers of Formula I, Formula II, and Formula III, or pharmaceutically acceptable salts thereof, wherein at least about 10%, at least about 20%, at least about 30%, at least about 40%, or at least about 50% of the mixture is hydrolyzed to the parent opioids within about 2 hours at 37° C. in 0.1 N HCl. In a particular embodiment, the method comprises orally administering to the mammal a therapeutically effective amount of a mixture of isomers of Formula I, Formula II, and Formula III, or pharmaceutically acceptable salts thereof, wherein at least about 10%, at least about 20%, at least about 30%, at least about 40%, at least about 50%, at least about 60%, at least about 70%, at least about 90%, or about 100% of a molar equivalent of the mixture of isomers of the compound of Formula I, Formula II, or Formula III is hydrolyzed to the parent opioid within about 4 hours at 37° C. in 0.1 N HCl.

In one embodiment, the invention is a method of achieving oxycodone therapy in a mammal in need of said therapy, comprising orally administering to the mammal a therapeutically effective amount of a compound of Formula IV or Formula V, or pharmaceutically acceptable salt thereof, wherein at least about 10%, at least about 20%, at least about 30%, at least about 40%, or at least about 50% of the compound of Formula IV or Formula V or salt is hydrolyzed to oxycodone within about 2 hours at 37° C. in 0.1 N HCl. In a particular embodiment, the method comprises orally administering to the mammal a therapeutically effective amount of a compound of Formula IV or Formula V, or pharmaceutically acceptable salt thereof, wherein at least about 10%, at least about 20%, at least about 30%, at least about 40%, at least about 50%, at least about 60%, at least about 70%, at least about 90°%, or about 100% of the compound of Formula IV or Formula V or salt is hydrolyzed to oxycodone within about 4 hours at 37° C. in 0.1 N HCl. In one embodiment, the method comprises orally administering isomer IVC, or pharmaceutically acceptable salt thereof, wherein about 80%, about 90%, about 95%, or about 100% of isomer IVC or salt is hydrolyzed to oxycodone within about 8 hours at 37° C. in 0.1 N HCl. In another embodiment, the method comprises orally administering isomer IVD, or pharmaceutically acceptable salt thereof, wherein about 80%, about 90%, about 95%, or about 100% of the compound of Formula IVD or salt is hydrolyzed to oxycodone within about 2 hours at 37° C. in 0.1 N HCl.

In another embodiment, the invention is a method of achieving oxycodone therapy in a mammal in need of said therapy, comprising orally administering to the mammal a therapeutically effective amount of a mixture of isomers of Formula IV and Formula V, or pharmaceutically acceptable salts thereof, wherein at least about 10%, at least about 20%, at least about 30%, at least about 40%, or at least about 50% of the mixture is hydrolyzed to oxycodone within about 2 hours at 37° C. in 0.1 N HCl. In a particular embodiment, the method comprises orally administering to the mammal a therapeutically effective amount of a mixture of isomers of Formula IV and Formula V, or pharmaceutically acceptable salts thereof, wherein at least about 10%, at least about 20%, at least about 30%, at least about 40%, at least about 50%, at least about 60%, at least about 70%, at least about 90%, or about 100% of the compound of Formula IV or Formula V or salt is hydrolyzed to oxycodone within about 4 hours at 37° C. in 0.1 N HCl.

In some embodiments, the compound of Formula I, Formula II, Formula III, Formula IV, or Formula V provides bioavailability of the parent opioid by any parenteral route (for example, intravenous, intranasal, or inhalation) of less than about 70%, less than about 50%, less than about 30%, less than about 20%, less than about 15%, less than about 10%, less than about 5%, less than about 4%, less than about 3%, less than about 2%, or less than about 1% of the bioavailability of the parent opioid administered by the same route.

Figure 12:
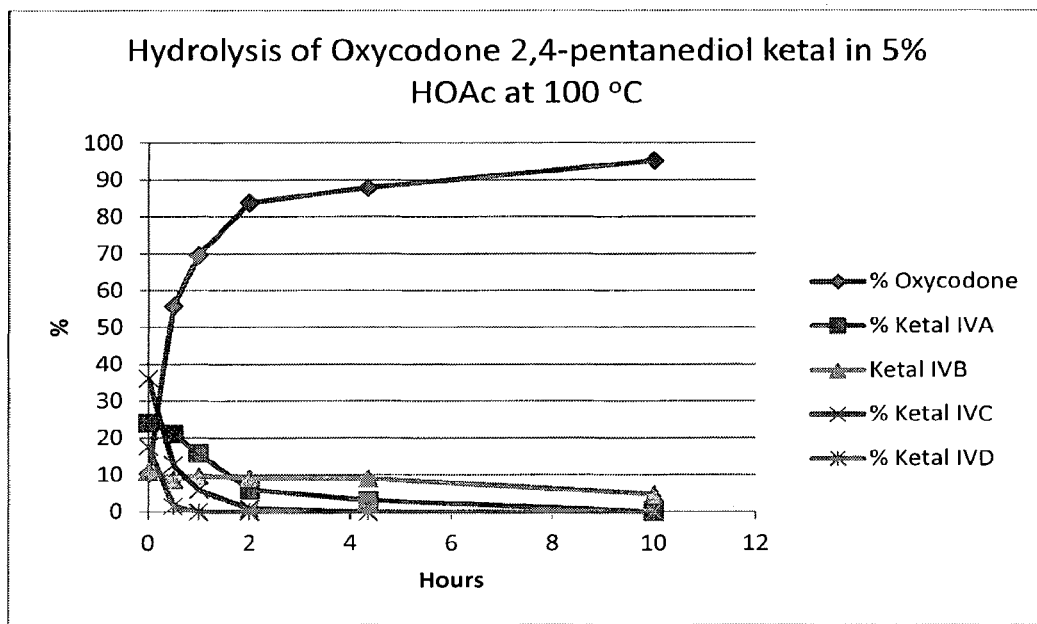
FIG. 12 is a graph of the hydrolysis of a mixture of four isomers of the compound of Formula IV (IVA-IVD) in 5% acetic acid when heated to 100° C., which is intended to simulate "kitchen chemistry" conditions that may be used by a potential abuser, and the release of oxycodone.
Figure 13:
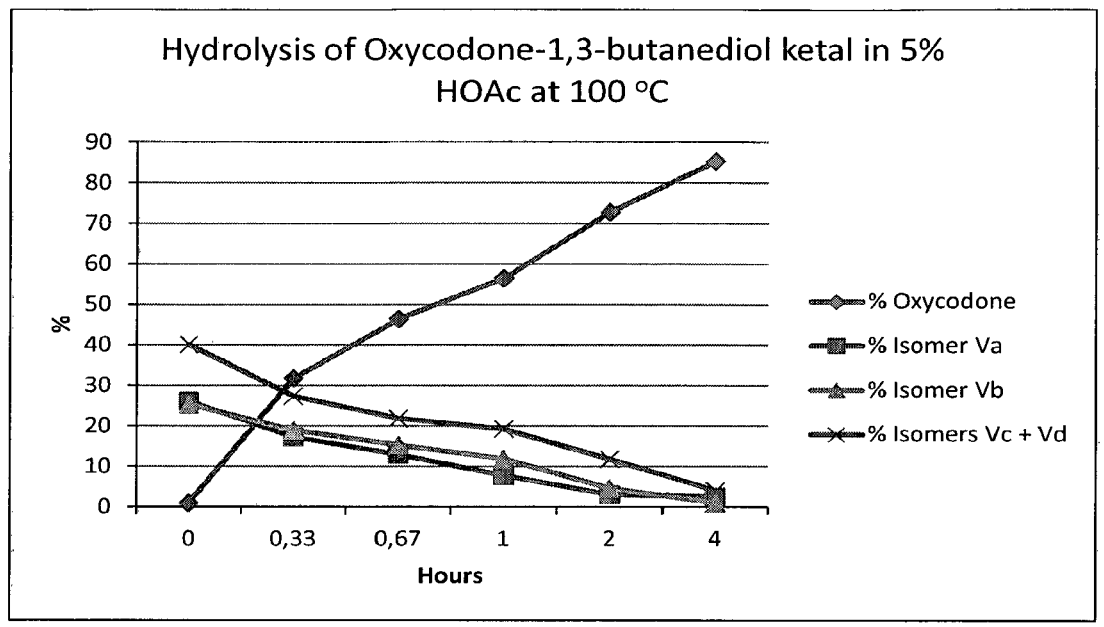
FIG. 13 is a graph of the hydrolysis of a mixture of four isomers of the compound of Formula V in 5% acetic acid at 100° C., and the release of oxycodone.

Compounds of the present invention exhibit a relatively high degree of stability, that is, resistance to hydrolysis, when subject to "kitchen chemistry" which might be used by a potential abuser. FIG. 12 presents the degree of hydrolysis of a mixture of the isomers of Formula IV (IVA-IVD) in the presence of 5% acetic acid at 100° C., which simulates boiling vinegar. As shown, a mixture of the isomers of Formula IV (IVA-IVD) requires about 2 hours in 5% acetic acid at 100° C. to exhibit about 80% hydrolysis to oxycodone and about 10 hours to almost completely hydrolyze to oxycodone. As shown in FIG. 13, a mixture of the isomers of Formula V requires about 1 hour to undergo about 60% hydrolysis and at least about 4 hours to almost completely hydrolyze to oxycodone when subjected to the same conditions.

Pharmaceutical Compositions

The present invention is further directed to pharmaceutical compositions comprising a therapeutically effective amount of at least one compound of Formula I, Formula II, Formula III, Formula IV, or Formula V, or a pharmaceutically acceptable salt thereof, and a pharmaceutically acceptable carrier. Pharmaceutical compositions of the present invention can, if desired, also contain one or more other compatible pharmaceutically active agents.

Pharmaceutical compositions within the scope of this invention include all compositions wherein a compound of Formula I, Formula II, Formula III, Formula IV, or Formula V, or a pharmaceutically acceptable salt thereof, is present in an amount that is effective (via conversion to the parent opioid) to achieve its intended purpose. While individual needs will vary, determination of optimal ranges of effective amounts of each component is within the skill in the art in view of the present disclosure. In some embodiments, a compound of Formula I, Formula II, Formula III, Formula IV, or Formula V, or a pharmaceutically acceptable salt thereof, or a mixture thereof, can be administered to a mammal. In some embodiments, the mammal is a human, and preferably a patient being treated for a condition that can be treated with an opioid, such as pain. As will be evident from this disclosure, compounds of Formula I, Formula II, Formula III, Formula IV, Formula V, pharmaceutically acceptable salts thereof, and mixtures thereof, are preferably administered orally. In some embodiments, a compound of Formula I, Formula II, Formula III, Formula IV, or Formula V is administered at a dose of from 0.1 to 5 mg/kg, or a molar equivalent amount of the pharmaceutically acceptable salt thereof, of the body weight of the mammal being treated.

In some embodiments, the unit oral dosage comprises between 5 mg and 640 mg, between 5 mg and 320 mg, between 5 mg and 200 mg, between 5 mg and 160 mg, between 5 mg and 100 mg, between 5 mg and 50 mg, between 5 mg and 25 mg, between 5 mg and 20 mg, and between 5 mg and 10 mg of a compound of Formula I, Formula II, Formula III, Formula IV, or Formula V, or a pharmaceutically acceptable salt thereof, or mixtures thereof. In some embodiments, the unit oral dose is 5 mg, 10 mg, 20 mg, 25 mg, 50 mg, 60 mg, 80 mg, 100 mg, 120 mg, 160 mg, 320 mg, or 640 mg of a compound of Formula I, Formula II, Formula III, Formula IV, or Formula V, or a molar equivalent of a pharmaceutically acceptable salt thereof.

In some embodiments, the oral dosage form is a unit oral dosage form that is administered every 4 hours, every 6 hours, every 8 hours, every 12 hours, or every 24 hours.

In some embodiments, a compound of Formula I, Formula II, Formula III, Formula IV, Formula V, or a pharmaceutically acceptable salt thereof, or a mixture thereof, can be administered as part of a pharmaceutical composition. In some embodiments, the pharmaceutical compositions of the invention contain one or more suitable pharmaceutically acceptable carriers selected from known excipients and auxiliaries to facilitate processing of the compounds into pharmaceutical dosage forms and/or to facilitate or otherwise control dissolution of the dosage form. In a particular embodiment, pharmaceutical compositions of the invention are in dosage forms that can be administered orally. In some embodiments, the pharmaceutical compositions are in the form of solid oral dosage forms, such as powders, granules, tablets, pellets, multiparticulates, dragees, or capsules. In other embodiments, the pharmaceutical compositions are in the form of liquid oral dosage forms, such as oral solutions, oral suspensions, or oral emulsions.

In some embodiments, the oral dosage form contains from 0.01 to 99 weight percent, 0.01 to 90 weight percent, 0.01 to 85 weight percent, 0.01 to 80 weight percent, or 0.01 to 75 weight percent of a compound of Formula I, Formula II, Formula III, Formula IV, Formula V, or a pharmaceutically acceptable salt thereof, or a mixture thereof, together with one or more excipients.

Orally administered pharmaceutical compositions of the invention can contain one or more excipients. Suitable excipients include fillers such as saccharides, for example lactose or sucrose, mannitol, sodium saccharin or sorbitol, magnesium carbonate, cellulose preparations and/or calcium phosphates, for example tricalcium phosphate or calcium hydrogen phosphate, as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents can be added such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, for example, silica, talc, stearic acid or salts thereof, such as magnesium stearate or calcium stearate, and/or polyethylene glycol; sweetening agents such as fructose, aspartame or saccharin; flavoring agents such as peppermint, oil of wintergreen, or cherry; coloring agents; and preserving agents, to provide a pharmaceutically palatable preparation. In addition, dye stuffs or pigments can be added to the tablets or dragee coatings, for example, for identification or in order to characterize combinations of active compound doses. Other examples of suitable pharmaceutical excipients are described in *Remington's Pharmaceutical Sciences* pp. 1447-1676 (Alfonso R. Gennaro ed., 19th ed. 1995), incorporated herein by reference. In one embodiment, the excipients are of pharmaceutical grade.

In some embodiments, pharmaceutical compositions of the present invention are manufactured in a manner which will be known in view of the present disclosure, such as, for example, by means of conventional mixing, granulating, dragee-making, dissolving, or lyophilizing processes.

Pharmaceutical compositions of the invention can be administered by any means to achieve their intended purpose. Preferably, administration is by the oral route. The dose administered and the frequency of dosing will be dependent upon the age, health, gender, medical condition and weight of the recipient, any concurrent treatment if any, frequency of treatment, and the nature of the effect desired, among other factors.

A compound of Formula I, Formula II, Formula III, Formula IV, Formula V, or a pharmaceutically acceptable salt thereof, or a mixture thereof, can be delivered in an immediate release system, a controlled-release system or a sustained-release system. For a more detailed description of the controlled- or sustained-release systems, see e.g. U.S. Pat. Nos. 5,672,360, 5,968,551, 6,294,195, 7,270,831, and 7,514,100. The controlled- or sustained-release systems can also be prepared by methods known in the art (see, e.g., Goodson, in Medical Applications of Controlled Release, vol. 2, pp. 115-138 (1984)). Other controlled- or sustained-release systems discussed in the review by Langer, *Science* 249:1527-1533 (1990) can be used as well.

A compound of Formula I, Formula II, Formula III, Formula IV, Formula V, or a pharmaceutically acceptable salt thereof, or a mixture thereof, can be prepared as a gastric-retentive drug delivery system, which is retained in the stomach or upper part of the gastrointestinal tract for controlled delivery. For a more detailed description of gastric-retentive drug delivery systems, see e.g. U.S. Pat. Nos. 5,232,704; 7,157,100; 7,838,028: and U.S. Patent Appl. Publication No. 2006/0013876. Gastric-retentive drug delivery systems can also be prepared by methods known in the art (see, e.g., Sharma, N., et al., *International Journal of Research in Pharmaceutical and Biomedical Sciences* 2:428-441 (2011)).

The production of tablets and granules as disclosed in U.S. Pat. Nos. 4,167,558 and 6,090,411 can also be used. The preparation of bilayered tablets as disclosed in U.S. Pat. No. 4,140,755 can also be used.

Powders comprising the active agent, a hydrocolloid, a pH dependent polymer, and a binder, with all of these being placed in a capsule, are disclosed in U.S. Pat. No. 5,169,638. The forms disclosed in said document are suitable for delivering compounds of the present invention.

U.S. Pat. No. 6,635,279 discloses a mixture of polyvinyl acetate and polyvinylpyrrolidone, as well as excipients. These forms can be prepared by simple processes and show exceptional mechanical strengths. The forms disclosed in said document are suitable for delivering a compound or compounds of the present invention.

In some embodiments, a compound or compounds of the present invention are co-administered with one or more other therapeutic agents.

In some embodiments, a compound or compounds of the present invention can be co-administered with one or more non-opioid analgesics. Suitable non-opioid analgesics include, but are not limited to a non-steroidal anti-inflammatory agent selected from aspirin, ibuprofen, diclofenac, naproxen, benoxaprofen, flurbiprofen, fenoprofen, flubufen, ketoprofen, indoprofen, piroprofen, carprofen, oxaprozin, pramoprofen, muroprofen, trioxaprofen, suprofen, aminoprofen, tiaprofenic acid, fluprofen, bucloxic acid, indomethacin, sulindac, tolmetin, zomepirac, tiopinac, zidometacin, acemetacin, fentiazac, clidanac, oxpinac, mefenamic acid, meclofenamic acid, flufenamic acid, niflumic acid tolfenamic acid, diflurisal, flufenisal, piroxicam, sudoxicam, isoxicam, pharmaceutically acceptable salts thereof, and mixtures thereof. Other suitable non-opioid analgesics include, but are not limited to, salicylic acid derivatives, including without limitation, sodium salicylate, choline magnesium trisalicylate, salsalate, diflunisal, salicylsalicylic acid, sulfasalazine, and olsalazin; para-aminophennol derivatives including without limitation, acetaminophen; indole and indene acetic acids, including without limitation, indomethacin, sulindac, and etodolac; heteroaryl acetic acids, including without limitation, tolmetin, diclofenac, and ketorolac; anthranilic acids (fenamates), including mefenamic acid and meclofenamic acid; enolic acids, including without limitation, oxicams (piroxicam and tenoxicam), and pyraznlidinediones (phenylbutazone and oxyphenthartazone); and alkanones, including without limitation, nabumetone. For a more detailed description of the non-opioid analgesics that can be co-administered with a compound of Formula I, Formula II, or Formula III, or a salt thereof, according to the present invention, see Paul A. Insel, Analgesic-Antipyretic and Antiinflammatory Agents and Drugs Employed in The Treatment of Gout in Goodman & Gilman's The Pharmacological Basis of Therapeutics, 617-657 (Perry B. Molinhoff and Raymond W. Ruddon, eds., 9th ed. 1996), and Glen R. Hanson, Analgesic, Antipyrctic and Anti-Inflammatory Drugs in Remington: The Science and Practice of Pharmacy, vol. II, 1196-1221 (A. R. Gennaro, ed. 19th ed. 1995).

In some embodiments, a compound or compounds of the present invention can be co-administered with one or more opioid agonists. Suitable opioid agonists include, but are not limited to, alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, oxymorphone, papaveretum, pentazocine, phenadoxone, phenomorphan, phenazocine, phenoperidine, piminodine, piritramide, proheptazine, promedol, properidine, propiram, propoxyphene, sufentanil, tilidine, tramadol, pharmaceutically acceptable salts thereof, and mixtures thereof.

In some embodiments, a compound or compounds of the present invention can be co-administered with one or more antimigraine agents. Suitable antimigraine agents include, but are not limited to, alpiropride, dihydroergotamine, dolasetron, ergocornine, ergocorninine, ergocryptine, ergot, ergotamine, flumedroxone acetate, fonazine, lisuride, lomerizine, methysergide oxetorone, pizotyline, and mixtures thereof.

In some embodiments, a compound or compounds of the present invention can be co-administered with one or more antiemetic agents. Suitable antiemetic agents include, but are not limited to, metoclopromide, domperidone, prochlorperazine, promethazine, chlorpromazine, trimethobenzamide, ondansetron, granisetron, hydroxyzine acethylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxyperndyl, pipamazine, scopolamine, sulpiride, tetrahydrocannabinols, thiethylperazine, thioproperazine, tropisetron, and mixtures thereof.

In some embodiments, a compound or compounds of the present invention can be co-administered with one or more p-adrenergic blockers. Suitable p-adrenergic blockers include, but are not limited to, acebutolol, alprenolol, amosulabol, arotinolol, atenolol, befunolol, betaxolol, bevantolol, bisoprolol, bopindolol, bucumolol, bufetolol, bufuralol, bunitrolol, bupranolol, butidrine hydrochloride, butofilolol, carazolol, carteolol, carvedilol, celiprolol, cetamolol, cloranolol, dilcvalol, epanolol, esmolol, indenolol, labetalol, levobunolol, mepindolol, metipranolol, metoprolol, moprolol, nadolol, nadoxolol, nebivalol, nifenalol, nipradilol, oxprenolol, penbutolol, pindolol, practolol, pronethalol, propranolol, sotalol, sulfinalol, talinolol, tertatolol, tilisolol, timolol, toliprolol, xibenolol, and mixtures thereof.

In some embodiments, a compound or compounds of the present invention can be co-administered with one or more anticonvulsants. Suitable anticonvulsants include, but are not limited to, acetylpheneturide, albutoin, aloxidone, aminoglutethimide, 4-amino-3-hydroxybutyric acid, atrolactamide, beclamide, buramate, calcium bromide, carbamazepine, cinromide, clomethiazole, clonazepam, decimemide, diethadione, dimethadione, doxenitroin, eterobarb, ethadione, ethosuximide, ethotoin, felbamate, fluoresone, gabapentin, 5-hydroxytryptophan, lamotrigine, magnesium bromide, magnesium sulfate, mephenytoin, mephobarbital, metharbital, methetoin, methsuximide, 5-methyl-5-(3-phenanthryl)-hydantoin, 3-methyl-5-phenylhydantoin, narcobarbital, nimetazepam, nitrazepam, oxcarbazepine, paramethadione, phenacemide, phenetharbital, pheneturide, phenobarbital, phensuximide, phenylmethylbarbituric acid, phenytoin, phethenylate sodium, potassium bromide, pregabaline, primidone, progabide, sodium bromide, solanum, strontium bromide, suclofenide, sulthiame, tetrantoin, tiagabine, topiramate, trimethadione, valproic acid, valpromide, vigabatrin, zonisamide, and mixtures thereof.

In some embodiments, a compound or compounds of the present invention can be co-administered with one or more antidepressants. Suitable antidepressants include, but are not limited to, binedaline, caroxazone, citalopram, dimethazan, fencamine, indalpine, indeloxazine hydrocholoride, nefopam, nomifensine, oxitriptan, oxypertine, paroxetine, sertraline, thiazesim, trazodone, benmoxine, iproclozide, iproniazid, isocarboxazid, nialamide, octamoxin, phenelzine, cotinine, rolicyprine, rolipram, maprotiline, metralindole, mianserin, mirtazepine, adinazolam, amitriptyline, amitriptylinoxide, amoxapine, butriptyline, clomipramine, demexiptiline, desipramine, dibenzepin, dimetacrine, dothiepin, doxepin, fluacizine, imipramine, imipramine N-oxide, iprindole, lofepramine, melitracen, metapramine, nortriptyline, noxiptilin, opipramol, pizotyline, propizepine, protriptyline, quinupramine, tianeptine, trimipramine, adrafinil, benactyzine, bupropion, butacetin, dioxadrol, duloxetine, etoperidone, febarbamate, femoxetine, fenpentadiol, fluoxetine, fluvoxamine, hematoporphyrin, hypericin, levophacetoperane, medifoxamine, milnacipran, minaprine, moclobemide, nefazodone, oxaflozane, piberaline, prolintane, pyrisuccideanol, ritanserin, roxindole, rubidium chloride, sulpiride, tandospirone, thozalinone, tofenacin, toloxatone, tranylcypromine, L-tryptophan, venlafaxine, viloxazine, zimeldine, and mixtures thereof.

In some embodiments, a compound or compounds of the present invention can be co-administered with one or more $Ca^{2+}$-channel blockers. Suitable $Ca^{2+}$-channel blockers include, but are not limited to, bepridil, clentiazem, diltiazem, fendiline, gallopamil, mibefradil, prenylamine, semotiadil, terodiline, verapamil, amlodipine, aranidipine, barnidipine, benidipine, cilnidipine, efonidipine, elgodipine, felodipine, isradipine, lacidipine, lercanidipine, manidipine, nicardipine, nifedipine, nilvadipine, nimodipine, nisoldipine, nitrendipine, cinnarizine, flunarizine, lidoflazine, lormerizine, bencyclane, etafenone, fantofarone, perhexiline, and mixtures thereof.

In some embodiments, a compound or compounds of the present invention are co-formulated or co-administered with an opioid antagonist, such as naltrexone, naloxone, nalmefene, nalorphine, nalbuphine, naloxoneazinen, methylnaltrexone, ketylcyclazocine, norbinaltorphimine, naltrindole, 6-β-naloxol, 6-β-naltrexol, alvimopan, cyprodime, diprenorphine, gemazocine, 5'-guanidinonaltrindole, JDTic ((3R)-7-Hydroxy-N-[(2S)-1-[(3R,4R)-4-(3-hydroxyphenyl)-3,4-dimethylpiperidin-1-yl]-3-methylbutan-2-yl]-1,2,3,4-tetrahydroisoquinoline-3-carboxamide), levallorphan, naldemedine, nalmexone, nalorphine dinicotinate, naloxazone, naloxegol, naloxol, naoloxonazine, naltiben, oxilorphan, quadazocine, samidorphan, and mixtures thereof according to International Patent Appl. Publication No. WO 03/084520.

Since compounds of of the present invention can act as opioid prodrugs, they can be used for the same purpose as their parent opioids. In some embodiments, the compounds of the invention are useful for treating, ameliorating or preventing pain including acute pain, chronic pain, neuropathic pain, inflammatory pain, and surgical pain. Acute pain includes, but is not limited to, peri-operative pain, post-operative pain, post-traumatic pain, acute disease-related pain, and pain related to diagnostic procedures, orthopedic manipulations, and myocardial infarction. Acute pain in the peri-operative setting includes pain resulting from a pre-existing disease, a surgical procedure, e.g., associated drains, chest or nasogastric tubes, or complications, or a combination of disease-related and procedure-related sources. Chronic pain includes, but is not limited to, inflammatory pain, post-operative pain, cancer pain, osteoarthritis pain associated with metastatic cancer, trigeminal neuralgia, acute herpetic and post-herpetic neuralgia, diabetic neuropathy, causalgia, brachial plexus avulsion, occipital neuralgia, reflex sympathetic dystrophy, fibromyalgia, gout, phantom limb pain, burn pain, and other forms of neuralgia, neuropathic, and idiopathic pain syndromes.

Chronic pain or neuropathic pain is a heterogencous disease state with an unclear etiology. In chronic pain, the pain can be mediated by multiple mechanisms. This type of pain generally arises from injury to the peripheral or central nervous tissue. In some embodiments, pain is associated with spinal cord injury, multiple sclerosis, post-herpetic neuralgia, trigeminal neuralgia, phantom pain, causalgia, reflex sympathetic dystrophy, and lower back pain. Chronic pain is different from acute pain in that patients suffer the abnormal pain sensations that can be described as spontaneous pain, continuous superficial burning, and/or deep aching pain. The pain can be evoked by heat-, cold-, and mechano-hyperalgesia or by heat-, cold-, or mechano-allodynia.

Neuropathic pain can be caused by injury or infection of peripheral sensory nerves. It includes, but is not limited to, pain from peripheral nerve trauma, herpes virus infection, diabetes mellitus, causalgia, plexus avulsion, neuroma, limb amputation, and vasculitis. Neuropathic pain is also caused by nerve damage from chronic alcoholism, human immunodeficiency virus infection, hypothyroidism, uremia, or vitamin deficiencies. Neuropathic pain includes but is not limited to pain caused by nerve injury such as, for example, the pain from which diabetics suffer.

In some embodiments, compounds of the invention are useful as cough suppressants, and in treating or ameliorating dyspnea, diarrhea, and dysentery.

In each of the aforementioned instances, the methods of the present invention require administering to a mammal in need of such treatment an effective amount of a compound of Formula I, Formula II, Formula III, Formula IV, Formula V, or a pharmaceutically acceptable salt thereof, or a mixture thereof.

In some embodiments, compounds of the invention are tested for their µ opioid receptor binding activity and their functional profile at the µ opioid receptor by the following in vitro binding assays.

µ Opioid Receptor Binding Assay:

Radioligand dose-displacement assays use 0.2 nM [$^3$H]-diprenorphine (Perkin Elmer, Boston, Mass.; 50.0 Ci/mmol) with 20 µg membrane protein (recombinant µ opioid receptor expressed in CHO-K1 cells (Perkin Elmer, Boston, Mass.) in a final volume of 500 µL binding buffer (10 nM $MgCl_2$, 1 mM EDTA, 5% DMSO, 50 mM Trizma base, pH 7.4). Unlabeled naloxone (Sigma-Aldrich, St. Louis, Mo.) serves as the assay positive control (concentration range $3\times10^{-7}$ to $1\times10^{-13}$ M). All reactions are performed in 96-deep well polypropylene plates for 2 hours at room temperature. Binding reactions are terminated by rapid filtration onto 96-well Unifilter GF/C filter plates (Packard, Meriden, Conn.) presoaked in 0.5% polyethylenimine (Sigma-Aldrich, St. Louis, Mo.). Harvesting is performed using a 96-well tissue harvester (Brandel, Gaithersburg, Md.) followed by three filtration washes with 500 µL icecold binding buffer. Filter plates are subsequently dried at 50° C. for 2-3 hours. 50 µL/well scintillation cocktail (BetaScint (Perkin Elmer, Boston, Mass.)) is added and plates are counted in a Packard Top-Count for 1 minute per well.

Opioid Receptor [$^{35}$S]GTP-γ-S Binding Functional Assay:

Functional [$^{35}$S]GTP-γ-S binding assays are conducted by sequentially mixing the following reagents in the order shown to yield the indicated final concentrations: 0.026 µg/µL µ membrane protein, 10 µg/mL saponin, 3 µM guanosine 5'-diphosphate (GDP) (Sigma Chemical Co., St. Louis, Mo.), and 0.20 nM [γ-$^{35}$S]guanosine 5'-(γ-thio)-triphosphate ([$^{35}$S]GTP-γ-S) (DuPont/New England Nuclear Co., Wilmington, Del.) to binding buffer (100 mM NaCl, 10 mM $MgCl_2$, 20 mM HEPES, pH 7.4) on ice. The prepared membrane solution (190 µL/well) is transferred to 96-shallow well polypropylene plates containing 10 µL of 20× concentrated stock solutions of compound or appropriate control prepared in dimethylsulfoxide (DMSO). Unlabeled [D-Ala$^2$, N-MePhe$^4$, Gly$^5$-ol]enkephalin (DAMGO) (Sigma-Aldrich, St. Louis, Mo.) serves as the assay positive control for the p functional assay. Plates are incubated for 30 minutes at room temperature with shaking. Reactions are terminated by rapid filtration onto 96-well Unifilter GF/B filter plates (Packard, Meriden, Conn.) using a 96-well tissue harvester (Brandel, Gaithersburg, Md.) and followed by three filtration washes with 200 µL ice-cold binding buffer (10 nM $NaH_2PO_4$, 10 mM $Na_2HPO_4$, pH 7.4). Filter plates are subsequently dried at 50° C. for 2-3 hours. 50 µL/well scintillation cocktail (BetaScint (Perkin Elmer, Boston, Mass.) is added and plates are counted in a Packard Top-Count for 1 min/well.

Data analysis: Data from both the binding and functional assays are analyzed using the curve fitting functions in GraphPad PRISM™, v. 3.0. Data are expressed as mean±S.E.M. The results from the binding assays are represented as inhibition constants, $K_i$ values (the concentration of a compound that produces half maximal inhibition). The results from the functional assays are represented as $EC_{50}$ values (the effective concentration of a compound that causes 50% of the maximum response).

In vivo Pharmacology: Compounds of of the invention can be tested for in vivo distribution to brains after oral administration using, for example, the following test. Sprague Dawley rats are dosed 10 mg/kg orally with the test compound. The dosing solution is in 25% 2-hydroxypropyl beta-cyclodextrin (HPBCD) and the dosing volume is 5 mL/kg. One hour after administration, the highest possible volume of blood is drawn through cardiac puncture. Plasma is separated from the whole blood by centrifugation and submitted for analysis. Following bleeding, the whole brains are harvested, briefly rinsed in cold normal saline, and then snap-frozen in liquid nitrogen. Both plasma and brain samples are stored at −70° C. prior to analysis.

For analyzing the plasma samples, calibration curves are prepared by spiking known amounts of analytes into commercially available control rat plasma. 200 µL aliquots of standards and study samples are added with 800 µL aqueous solution of internal standard (oxycodone) and extracted on the Cis solid-phase cartridges (96-well format, 3M) according to the following procedure. The cartridges are activated by applying 500 µL methanol followed by 500 µL of water. Then the samples are applied and cartridges are washed with 500 µL of water and then eluted with 2×500 µL of 1% formic acid in methanol followed by 2×500 µL of 2% ammonia in methanol. Upon evaporation and reconstitution, the samples are analyzed by LC/MS/MS. For analyzing the brain samples, study samples and control brains are homogenized with water in a ratio of 1:10 weight per volume. Calibration curves are prepared by spiking known amounts of the analytes into control brain homogenates. 500 µL aliquots of standards and study samples are added with 500 µL aqueous solution of internal standard (oxycodone) and extracted on the $C_{18}$ solid-phase cartridges (96-well format, 3M) according to the procedure described earlier for plasma samples. Upon evaporation and reconstitution, the samples are analyzed by LC/MS/MS.

Analytes and internal standards are chromatographed on Zorbax Extended Cis column (4.6×150 mm, 3.5 microns particle size) under water-acetonitrile gradient conditions (specific gradient for each analyte) using procedures known in the art. The effluents are analyzed by MS/MS. The analytes are registered as "daughter" ions of the analytes' molecular ions on the second quadropole of the instrument. The MS/MS conditions are optimized for each individual analyte to achieve maximum selectivity and sensitivity.

The concentrations of the unknown samples are calculated based on the parameters of the corresponding calibration curves. The brain concentrations expressed in "ng per g of tissue" are obtained by multiplying the corresponding homogenate concentrations by a factor of 10 (dilution factor during the homogenation step). The brain-to-blood ratio are calculated as the ratio of the corresponding brain (ng/g) and plasma (ng/mL) concentrations for each individual animal and the means and standard deviations are calculated for the groups of three.

Compounds of the invention can be tested for their anti-nociceptive activity in the formalin model as described in Hunskaar, S., O. B. Fasmer, and K. Hole, *J. Neurosci. Methods* 14: 69-76 (1985). Male Swiss Webster NIH mice (20-30 g; Harlan, San Diego, Calif.) are used in all experiments. Food is withdrawn on the day of the experiment. Mice are placed in Plexiglass jars for at least 1 hour to accommodate to the environment. Following the accommodation period, mice are weighed and given either the compound of interest administered orally in a vehicle, or the appropriate volume of vehicle (10% Tween-80). Thirty minutes after the oral dosing, mice are injected with formalin (20 µL of 5% formaldehyde solution in saline) into the dorsal surface of the right hind paw. Mice are transferred to the Plexiglass jars and monitored for the amount of time spent licking or biting the injected paw. Periods of licking and biting are recorded in 5 minute intervals for 1 hour after the formalin injection. All experiments are done in a blinded manner during the light cycle. The early phase of the formalin response is measured as licking/biting between 0 and 5 minutes, and the late phase is measured from 15 to 50 minutes. Differences between vehicle and drug treated groups are analyzed by one-way analysis of variance (ANOVA). A p value ≤0.05 is considered significant. Compounds having activity in blocking the acute and second phase of formalin-induced paw-licking activity are considered to be efficacious for acute and chronic pain.

Compounds of the invention can be tested for their potential to treat chronic pain (anti-allodynic and anti-hyperalgesic activities) using the Chung model of peripheral neuropathy. Male Sprague-Dawley rats weighing between 200 and 225 g are anesthetized with halothane (1 to 3% in a mixture of 70% air and 30% oxygen) and their body temperature controlled during anesthesia through use of a homeothermic blanket. A 2-cm dorsal midline incision is then made at the L5 and L6 level and the para-vertebral muscle groups retracted bilaterally. L5 and L6 spinal nerves are then exposed, isolated, and tightly ligated with 6-0 silk suture. A sham operation is performed exposing the contralateral L5 and L6 spinal nerves as a negative control.

Tactile Allodynia: Rats are transferred to an elevated testing cage with a wire mesh floor and allowed to acclimate for five to ten minutes. A series of Semmes-Weinstein monofilaments are applied to the plantar surface of the hindpaw to determine the animal's withdrawal threshold. The first filament used possesses a buckling weight of 9.1 gms (0.96 log value) and is applied up to five times to see if it elicits a withdrawal response. If the animal has a withdrawal response, then the next lightest filament in the series will be applied up to five times to determine if it can elicit a response. This procedure is repeated with subsequent lesser filaments until there is no response and the lightest filament that elicited a response is recorded. If the animal does not have a withdrawal response from the initial 9.1 gins filament, then subsequent filaments of increased weight are applied until a filament elicits a response and this filament is then recorded. For each animal, three measurements are made at every time point to produce an average withdrawal threshold determination. Tests are performed prior to and at 1, 2, 4, and 24 hours post drug administration. Tactile allodynia and mechanical hyperalgesia tests are conducted concurrently.

Mechanical Hyperalgesia: Rats are transferred to an elevated testing cage with a wire mesh floor and allowed to acclimate for five to ten minutes. A slightly blunted needle is touched to the plantar surface of the hindpaw causing a dimpling of the skin without penetrating the skin. Administration of the needle to control paws typically produces a quick flinching reaction too short to be timed with a stopwatch, and arbitrarily given a withdrawal time of 0.5 second. The operated side paw of neuropathic animals exhibits an exaggerated withdrawal response to the blunted needle. A maximum withdrawal time of ten seconds is used as a cutoff time. Withdrawal times for both paws of the animals are measured three times at each time point with a five-minute recovery period between applications. The three measurements are used to generate an average withdrawal time for each time point. Tactile allodynia and mechanical hyperalgesia tests are conducted concurrently.

The following examples are illustrative, but not limiting, of the methods and compositions of the present invention. Other suitable modifications and adaptations of the variety of conditions and parameters normally encountered in clinical therapy and which are obvious to those skilled in the art are within the spirit and scope of the invention.

PREPARATION EXAMPLES

Example 1

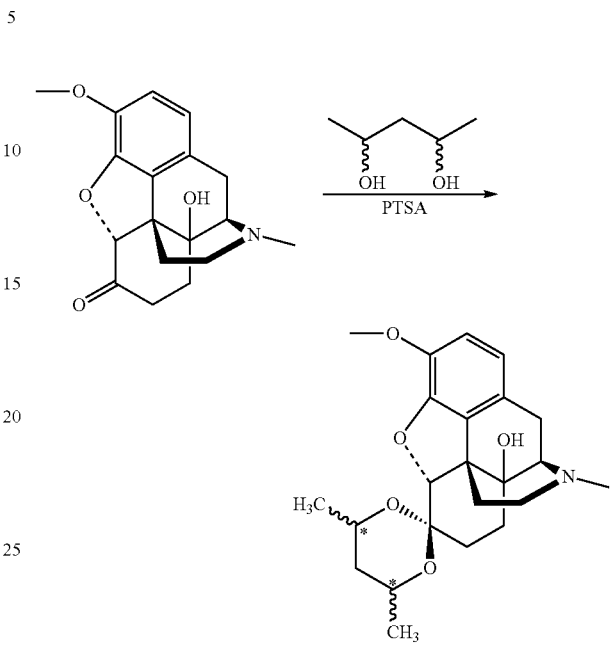

Figure 7:
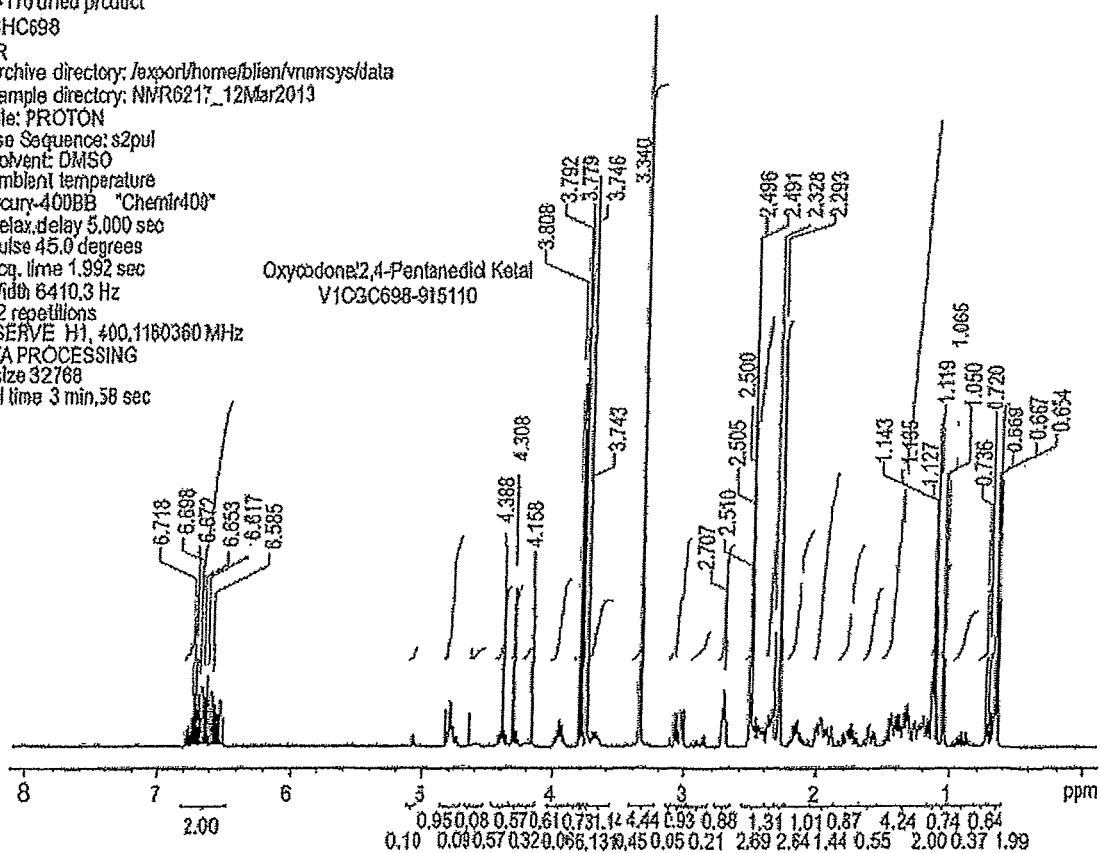
FIG. 7 is the $^1$H NMR (d6-DMSO) spectrum of the compound of Formula IV (oxycodone 2,4-pentanediol ketal).

Preparation of a compound of Formula IV (oxycodone 2,4-pentanediol ketal): Oxycodone free base (2.91 g), p-toluenesulfonic acid monohydrate (2.17 g) and 2,4-pentanediol (5.40 g, mixture of isomers) were stirred in toluene (250 mL) and heated under reflux with a Dean Stark water trap attached. After 3½ hours, the mixture was cooled, treated with triethylamine (5 mL), and washed with water (2×50 mL). The toluene solution was concentrated under reduced pressure to a clear resin that solidified on standing to afford a white solid (Formula I) (3.87 g). FIG. 7 provides the $^1$H NMR (d6-DMSO) spectrum of the compound of Formula IV (oxycodone 2,4-pentanediol ketal).

Using the procedure detailed herein, isomers IVC and IVD were prepared by reacting oxycodone with 2S,4S-pentanediol and 2R,4R-pentanediol, respectively. In addition, using the procedure detailed herein, a mixture of isomers IVA and IVB was prepared by reacting oxycodone with meso-2,4-pentanediol.

Example 2

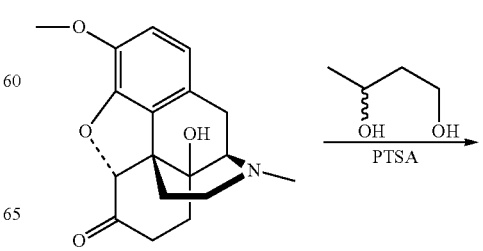

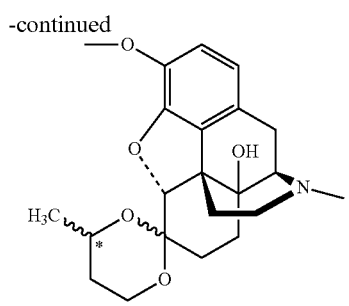

Figure 8:
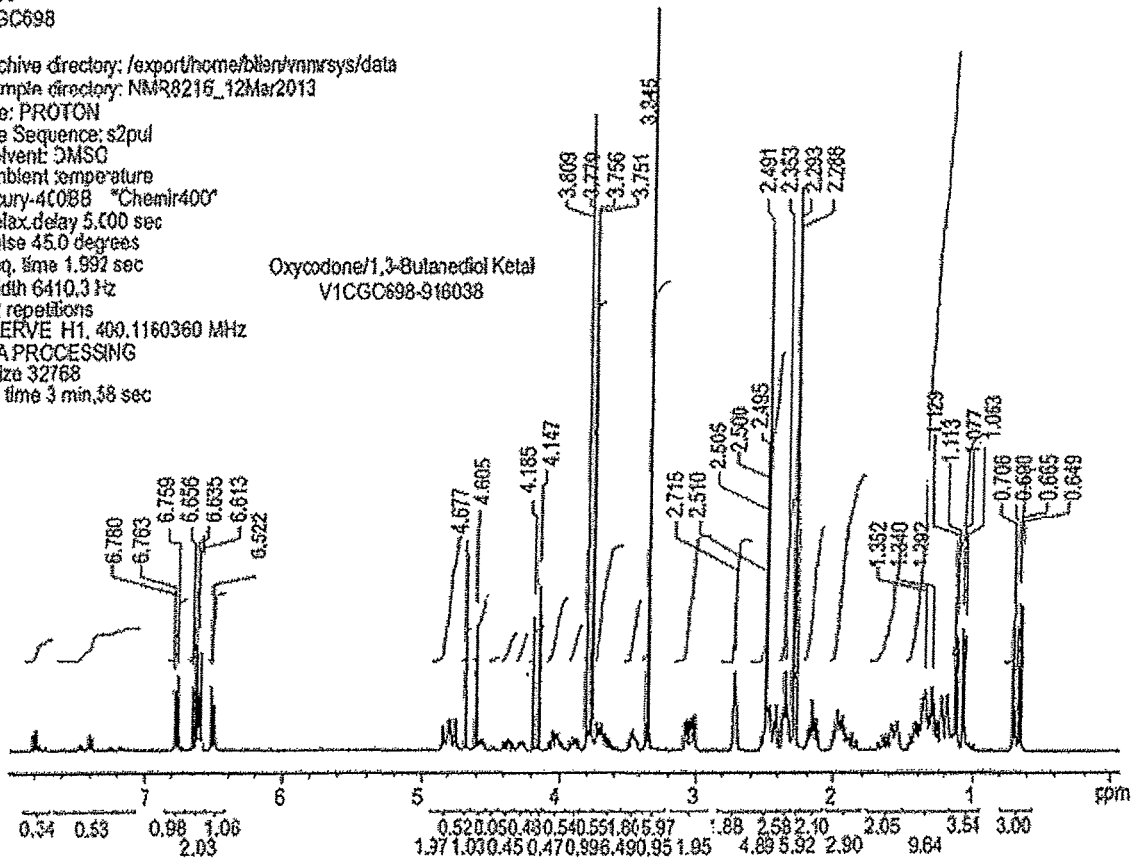
FIG. 8 is the $^1$H NMR (d6-DMSO) spectrum of the compound of Formula V (oxycodone 1,3-butanediol ketal).

Preparation of compound of Formula V (oxycodone 1,3-butanediol ketal): Oxycodone free base (1.58 g), p-toluenesulfonic acid (1.19 g) and 1,3-butanediol (5.73 g, mixture of isomers) were stirred in toluene (125 mL) and heated under reflux with a Dean Stark water trap attached. After 5 hours the mixture was cooled and washed with saturated sodium bicarbonate solution (2×50 mL), then with water (50 ml). The solution was dried over magnesium sulfate, filtered, and concentrated under reduced pressure to a colorless resin that solidified on standing to afford a white solid (2.12 g). FIG. 8 provides the $^1$H NMR (d6-DMSO) spectrum of the compound of Formula V (oxycodone 1,3-butanediol ketal).

Using the general scheme shown above, the following compounds were prepared and characterized. Characterization was carried out using an LC/MS system. The LC/MS utilized a Phenomenex Luna C18 column and a gradient elution with the first solvent of 90% 2.8 mM ammonium formate in water, 10% methanol, and the second solvent of methanol, at a flow rate of 0.3 mL/min. The molecular weight peaks for each of the compounds prepared are shown below:

| Product | Characterization Data | Retention time(s) (min) |
| --- | --- | --- |
| hydrocodone 2,4-pentanediol ketal | 386.2 (MH+), 387.2 (MH+) | 17.22, 17.65, 17.99 |
| oxycodone 2,5-hexanediol ketal | 416.20 (MH+), 417.20 (MH+) | 19.61, 19.98, 21.30, 22.14, 23.36, 24.49 |
| hydrocodone 2,5-hexanediol ketal | 400.2 (MH+), 401.3 (MH+) | 19.61, 22.57, 23.51 |
| hydromorphone 2,4-pentanediol ketal | 372.2 (MH+), 373.2 (MH+) | 18.24, 18.77, 19.23 |
| oxycodone with 1,3-butanediol (Formula V) | 388.2 (MH+), 389.2 (MH+) | 18.11, 19.24 |
| oxycodone 1,2-cyclohexanedimethanol ketal | 442.2 (MH+), 443.2 (MH+) | 25.14, 25.66 |
| Hydrocodone 1,3-propanediol ketal | 358.2 (MH+), 359.2 (MH+) | 17.73 |

Using the general scheme shown above, gram amounts of the following compounds were prepared. Additional purification of the compounds was carried out by recrystallization in ethanol or silica gel chromatography. Characterization was carried out using an LO/MS system and $^1$H NMR spectroscopy. The compounds, quantities prepared, and purity levels are shown below:

| Compound | Quantity (g) | % Purity (LCMS) |
| --- | --- | --- |
| Oxycodone 2,4-pentanediol ketal (mixed isomers) | 5.17 g | 99.77 |
| Oxycodone 2R,4R-pentanediol ketal | 0.80 g | 99.71 |
| Oxycodone 2S,4S-pentanediol ketal | 6.82 | 99.82 |
| Hydrocodone 2,4-pentanediol ketal (mixed isomers) | 2.14 | 99.50 |
| Hydrocodone 2R,4R-pentanediol ketal | 6.20 | 98.31 |
| Hydrocodone 2S,4S-pentanediol ketal | 6.58 | 99.36 |
| Hydromorphone 2,4-pentanediol ketal | 1.00 | 99.25 |

Hydrolysis Studies with Simulated Gastric Fluid and 0.1 N HCl

Example 3

A mixture of isomers of oxycodone 2,4-pentanediol ketal along with unreacted oxycodone at a concentration of 2 mg/ml was subjected to hydrolysis in USP Simulated Gastric Fluid (SGF) (0.2% NaCl and 0.32% pepsin in 0.084 N HCl) at 37° C., with analysis of the hydrolyzed oxycodone conducted by LC/MS. Results from the hydrolysis are shown in Table 1a and illustrated in FIG. 1.

As a comparison, a mixture of isomers of oxycodone 2,4-pentanediol ketal along with unreacted oxycodone was dissolved in 0.1 N HCl at a concentration of 2 mg/ml and heated to 37° C. The course of the hydrolysis was monitored by LC/MS. Results from the hydrolysis are shown in Table 1b and illustrated in FIG. 1.

TABLE 1a

| | Simulated Gastric Fluid | | | | |
| --- | --- | --- | --- | --- | --- |
| Hours | Oxycodone | Ketal A | Ketal B | Ketal C | Ketal D |
| 0 | 7.3 | 26.6 | 10.3 | 38.4 | 17.3 |
| 0.58 | 19.9 | 25.7 | 9.8 | 32.8 | 11.7 |
| 1.25 | 35.3 | 25.3 | 10.4 | 25.2 | 3.8 |
| 2 | 43 | 24.2 | 9.7 | 21 | 1.6 |
| 3 | 51 | 23.7 | 10.2 | 14.2 | 0.85 |
| 4 | 58.7 | 22.7 | 9.1 | 9.4 | 0 |

TABLE 1b

| | 0.1N HCl | | | | |
| --- | --- | --- | --- | --- | --- |
| Hours | Oxycodone | Ketal A | Ketal B | Ketal C | Ketal D |
| 0 | 11.4 | 24.7 | 10.7 | 35.8 | 17.3 |
| 0.583 | 25.5 | 25.9 | 10.6 | 29.2 | 8.6 |
| 1.167 | 33 | 25.6 | 10.7 | 26 | 4.8 |
| 1.75 | 44 | 25 | 7.8 | 20.6 | 2.6 |
| 2.33 | 47.6 | 25.9 | 8.3 | 17.7 | 1.5 |
| 2.92 | 50.9 | 24.8 | 8.7 | 15 | 0.7 |
| 4 | 56.8 | 23.7 | 9.2 | 10.3 | 0 |

The results show that the hydrolysis rates of the isomers are similar in 0.1 N HCl and SGF, indicating that the pepsin enzyme present in the SGF has little effect on the hydrolysis rate.

Example 4

Hydrocodone 2,4-pentanediol ketal at a concentration of 1 mg/ml was subjected to hydrolysis in USP Simulated Gastric Fluid (SGF) (0.2% NaCl and 0.32% pepsin in 0.084 N HCl) at 37° C., with analysis of the hydrolyzed hydrocodone conducted by LC/MS. Results from this hydrolysis are shown in Table 2a and illustrated in FIG. 2.

As a comparison, a mixture of four stereoisomers of hydrocodone 2,4-pentanediol ketal along with unreacted hydrocodone was dissolved in 0.1 N HCl at a concentration of 1 mg/ml and heated to 37° C. The course of the hydrolysis was monitored by LC/MS. Results from this hydrolysis are shown in Table 2b and illustrated in FIG. 2. Two of the stereoisomers designated as Ketal A+B were not resolved under the LC/MS conditions employed.

TABLE 2a

| | SGF | | | |
|---|---|---|---|---|
| Hours | Hydrocodone | % Ketal A + B | % Ketal C | % Ketal D |
| 0 | 1 | 31.4 | 38.3 | 29.3 |
| 0.58 | 33.7 | 26.4 | 32.3 | 7.5 |
| 1.25 | 45.9 | 25.8 | 25.6 | 2.6 |
| 2 | 48.1 | 28 | 23 | 0 |
| 3 | 55.1 | 28.9 | 15.9 | 0 |
| 4 | 58.3 | 29 | 12.7 | 0 |

TABLE 2b

| | 0.1N HCl | | | |
|---|---|---|---|---|
| Hours | Hydrocodone | % Ketal A + B | % Ketal C | % Ketal D |
| 0 | 3 | 30.1 | 37.3 | 29.6 |
| 0.58 | 29.2 | 30.2 | 32.3 | 8.3 |
| 1.25 | 41.1 | 29.4 | 28 | 1.5 |
| 2 | 41.5 | 38 | 20.6 | 0 |
| 3 | 53.4 | 32.5 | 14.3 | 0 |
| 4 | 59.4 | 31.3 | 9.3 | 0 |

The results show that the hydrolysis rates of the isomers are similar in 0.1 N HCl and SGF, indicating that the pepsin enzyme present in the SGF has little effect on the hydrolysis rate.

Example 5

A mixture of isomers of hydromorphone 2,4-pentanediol ketal along with unreacted hydromorphone at a concentration of 1 mg/ml was subjected to hydrolysis in 0.1 N HCl at 37° C., with analysis of the hydrolyzed hydromorphone conducted by LC/MS. Results from the hydrolysis are shown in Table 3 and illustrated in FIG. 3. The % increase in hydromorphone represents the hydromorphone released from the hydrolysis of the ketals.

TABLE 3

| Hours | % Hydromorphone | % Increase in hydromorphone | % Ketal A | % Ketal B | % Ketal C | % Ketal D |
|---|---|---|---|---|---|---|
| 0 | 63.3 | 0 | 3.6 | 5 | 8.7 | 19.1 |
| 0.58 | 72.5 | 9.2 | 3.1 | 5 | 8.1 | 11.2 |
| 1.25 | 75.4 | 12.1 | 3 | 5.1 | 8 | 8.5 |
| 2 | 78.8 | 15.5 | 3.2 | 5.6 | 6.7 | 5.6 |
| 3.15 | 83 | 19.7 | 2.9 | 5.8 | 5.4 | 2.9 |
| 4 | 85 | 21.7 | 2.3 | 5.6 | 4.9 | 2.1 |

As shown in Table 3 and FIG. 3, Ketal D showed near complete hydrolysis in 4 hours at 0.1 N HCl at 37° C. In comparison, ketals A, B, and C hydrolyzed more slowly and did not hydrolyze completely within 4 hours in 0.1 N HCl at 37° C.

Example 6

A mixture of oxycodone cis 1,2-cyclohexanedimethanol ketals was prepared as described above and subjected to hydrolysis in 0.1 N HCl at 37° C. at a concentration of 1 mg/ml. Results from the analysis are shown below in Table 4 and FIG. 4.

TABLE 4

| Hours | % Oxycodone | % Ketal A | % Ketal B |
|---|---|---|---|
| 0 | 27.2 | 32.2 | 39 |
| 0.56 | 28.1 | 29.5 | 39.7 |
| 1.25 | 33.8 | 28.5 | 36.3 |
| 2 | 37.4 | 27.6 | 32.7 |
| 4.45 | 56.4 | 20.2 | 23.4 |

Example 7

Hydrocodone 1,3-propanediol ketal was prepared according to the general procedures above and tested for hydrolysis in 0.1 N HCl at 37° C. at a concentration of 1 mg/ml. Results from the analysis are shown below in Table 5 and FIG. 5.

TABLE 5

| Hours | % hydrocodone | % Ketal |
|---|---|---|
| 0 | 6.9 | 93.1 |
| 0.57 | 34.3 | 65.7 |
| 1.25 | 47.7 | 52.3 |
| 2 | 58.2 | 41.8 |
| 3 | 67.8 | 32.8 |
| 4 | 74.4 | 25.6 |

Example 8

Hydrocodone 2S,5S-hexanediol ketal and hydrocodone 2R,5R-hexanediol ketal were individually prepared and separately tested for hydrolysis in 0.1 N HCl at 37° C. at concentrations of 1 mg/ml each. The hydrolysis rates are shown below in Tables 6a and 6b. The hydrolysis of the ketals and corresponding release of hydrocodone are shown in FIG. 6. The dashed lines represent 2S,5S hydrocodone hexanediol ketal and the released hydrocodone. The solid lines represent hydrocodone 2R,5R hexanediol ketal and the hydrolyzed hydrocodone.

TABLE 6a

| Hours | Hydrocodone | 2S,5S ketal |
|---|---|---|
| 0 | 18.02 | 81.98 |
| 0.5 | 47.82 | 52.18 |
| 1.25 | 64.89 | 35.11 |
| 2 | 89.81 | 10.19 |
| 3 | 95.71 | 4.29 |
| 4 | 98 | 2 |

TABLE 6b

| Hours | Hydrocodone | 2R,5R ketal |
|---|---|---|
| 0 | 26.1 | 73.88 |
| 0.5 | 65.4 | 34.6 |
| 1.25 | 88.6 | 11.37 |
| 2 | 97.3 | 2.67 |

TABLE 6b-continued

| Hours | Hydrocodone | 2R,5R ketal |
|---|---|---|
| 3 | 100 | 0 |
| 4 | 100 | 0 |

Example 9

Oxycodone 2,4-pentanediol ketal (1.1 mg, mixture of isomers) was stirred in fresh EDTA stabilized blood plasma for 5 minutes. The mixture was filtered (0.45 micron PTFE) and analyzed by LC/MS. The sample was held at 37° C. for four hours, filtered (0.45 micron PTFE) and analyzed by LC/MS. The results showed that approximately 6% of the ketal hydrolyzed to oxycodone over the four hour period.

Hydrocodone 2,4-pentanediol ketal (1.1 mg, mixture of isomers) was stirred in fresh EDTA stabilized blood plasma for 5 minutes. The mixture was filtered (0.45 micron PTFE) and analyzed by LC/MS. The sample was held at 37° C. for four hours, filtered (0.45 micron PTFE) and analyzed by LCMS. The results showed that approximately 0.2% of the ketal hydrolyzed to hydrocodone over the four hour period.

The results therefore indicate that an abuser will be less likely to abuse the opioid ketal compounds of the invention by parenteral administration (i.e., inhalation or injection) of the drug to achieve rapid euphoria.

Example 10

The following opioid ketals having five membered ketal rings were synthesized and tested for hydrolysis in 0.1 N HCl at 37° C. and/or SGF, respectively.

| Compound | Hydrolysis in 0.1N HCl at 37° C. | Hydrolysis in SGF |
|---|---|---|
| 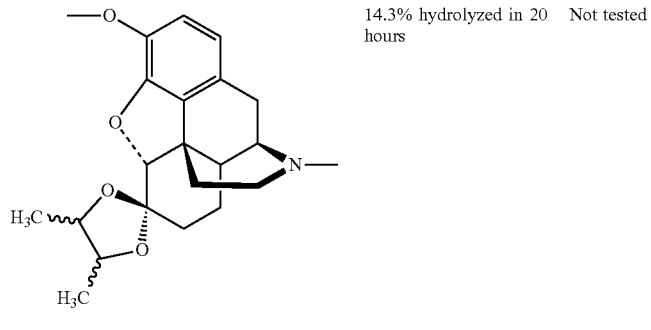<br>Hydrocodone 2,3-butanediol ketal | 14.3% hydrolyzed in 20 hours | Not tested |
| 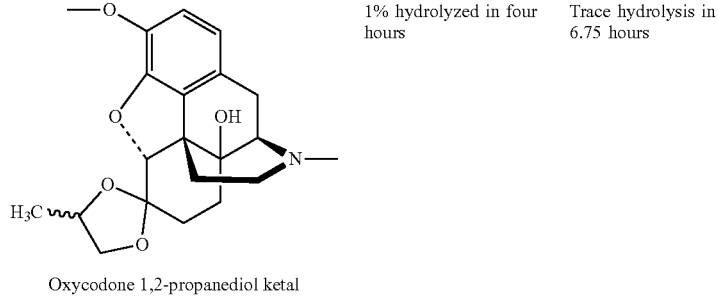<br>Oxycodone 1,2-propanediol ketal | 1% hydrolyzed in four hours | Trace hydrolysis in 6.75 hours |
| 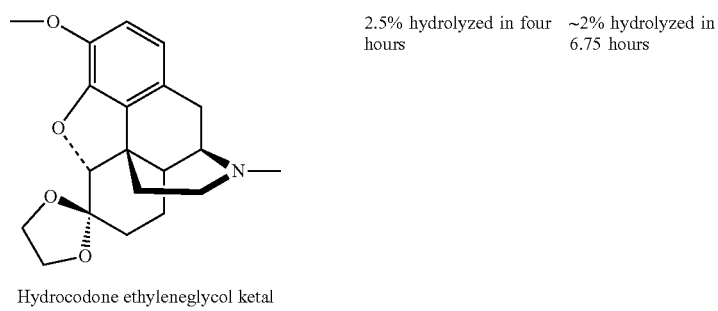<br>Hydrocodone ethyleneglycol ketal | 2.5% hydrolyzed in four hours | ~2% hydrolyzed in 6.75 hours |

| Compound | Hydrolysis in 0.1N HCl at 37° C. | Hydrolysis in SGF |
|---|---|---|
| 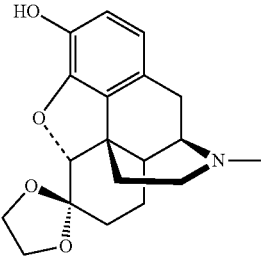 Hydromorphone ethyleneglycol ketal | 6.6% hydrolyzed in 19 hours | Not tested |

Example 11

Improved Synthesis of Compounds of the Invention Using a Small Excess of Dial

An exemplary preparation of a compound of Formula I: A solution of oxycodone (1 equivalent), 2R,4R-pentanediol (1.1 equivalent), p-toluenesulfonic acid monohydrate (1.5 equivalent), and toluene was brought to reflux while under a stream of nitrogen. Water was azeotropically removed into a Dean Stark trap. The solution was refluxed for a total of 22.5 hours with aliquots for LCMS taken at 3.5, 6 and 22.5 hours. Approximately 25% of the starting oxycodone remained unconsumed after 22.5 hours. Minimal impurities were present in the final reaction mixture.

Example 12

Hydrolysis Studies of Formula IV (Oxycodone 2,4-Pentanediol Ketal) in 0.1 N HCl at 37° C.

A mixture of unreacted oxycodone and four isomers of Formula IV (IVA-IVD) was dissolved in 0.1 N HCl at a total concentration of 1 mg/ml and heated to 37° C. The course of the hydrolysis was monitored by LC/MS. Results from the hydrolysis are shown in Table 7 and illustrated in FIG. 9.

TABLE 7

| Hours | % Oxycodone | % IVA | % IVB | % IVC | % IVD |
|---|---|---|---|---|---|
| 0 | 11.4 | 24.7 | 10.7 | 35.8 | 17.3 |
| 0.583 | 25.5 | 25.9 | 10.6 | 29.2 | 8.6 |
| 1.167 | 33 | 25.6 | 10.7 | 26 | 4.8 |
| 1.75 | 44 | 25 | 7.8 | 20.6 | 2.6 |
| 2.33 | 47.6 | 25.9 | 8.3 | 17.7 | 1.5 |
| 2.92 | 50.9 | 24.8 | 8.7 | 15 | 0.7 |
| 4 | 56.8 | 23.7 | 9.2 | 10.3 | 0 |
| 6.5 | 66 | 19.8 | 10 | 4 | 0 |
| 9.75 | 72.6 | 15.6 | 10.2 | 1.5 | 0 |
| 13.75 | 79.7 | 9.9 | 10.4 | 0 | 0 |
| 25 | 86.4 | 4.3 | 9.3 | 0 | 0 |

Isomers IVC and IVD were individually prepared and separately tested for their hydrolysis in 0.1 N HCl at 37° C. at concentrations of 1 mg/ml each. Results from the hydrolysis were normalized, and are presented in Tables 8a and 8b and illustrated in FIG. 10. The dashed lines represent oxycodone 2S,5S pentanediol ketal and the hydrolyzed oxycodone. The solid lines represent oxycodone 21R,51R pentanediol ketal and the hydrolyzed oxycodone.

TABLE 8a

| Hours | % Oxycodone | % IVD (Oxycodone 2R,4R-pentanediol ketal) |
|---|---|---|
| 0 | 0.8 | 99.8 |
| 0.17 | 26.9 | 70 |
| 0.33 | 55.2 | 44.8 |
| 1 | 89.2 | 10.8 |
| 2 | 98 | 2 |

TABLE 8b

| Hours | Oxycodone | % IVC (Oxycodone 2S,4S-pentanediol ketal) |
|---|---|---|
| 0 | 1.3 | 98.7 |
| 0.75 | 28.5 | 71.5 |
| 1.5 | 46 | 54 |
| 3.33 | 81.2 | 18.8 |
| 6 | 95.3 | 4.7 |
| 8 | 97.9 | 2.1 |

A mixture of unreacted oxycodone and four isomers of Formula V (Va-Vd) was dissolved in 0.1 N HC at a concentration of 1 mg/m2 and heated to 37° C. The course of the hydrolysis was monitored by LC/MS. Results from the hydrolysis are shown in Table 9 and illustrated in FIG. 11.

TABLE 9

| Hours | % Oxycodone | % Va* | % Vb* | % Vc* + Vd* |
|---|---|---|---|---|
| 0 | 1 | 26.1 | 25.3 | 40.1 |
| 0.58 | 14.1 | 21.7 | 23.4 | 37.3 |
| 1.17 | 20.8 | 18.7 | 21.8 | 35.5 |
| 2.5 | 32.8 | 13.7 | 20.1 | 29.7 |
| 5 | 49 | 6.6 | 17.7 | 24.9 |
| 10 | 69.3 | 0.2 | 11.3 | 17.3 |
| 25 | 87.7 | 0.7 | 3.2 | 7.8 |

*The stereochemistry of each of the isomers Va-Vd is to be determined.

Example 13

Hydrolysis Study: 5% Acetic Acid at 100° C.

A mixture of unreacted oxycodone and four isomers of Formula IV (IVA-IVD) was dissolved in 5% acetic acid at a concentration of 1 mg/ml and heated to 100° C. The course of the hydrolysis was monitored by LC/MS. Results from the hydrolysis are shown in Table 4 and illustrated in FIG. 12.

TABLE 10

| Hours | % Oxycodone | % IVA | % IVB | % IVC | % IVD |
|---|---|---|---|---|---|
| 0 | 10.3 | 24 | 10.9 | 36.2 | 17.6 |
| 0.5 | 55.8 | 21.1 | 8.7 | 12.8 | 1.5 |
| 1 | 69.6 | 15.8 | 9.7 | 5.9 | 0 |
| 2 | 83.9 | 6 | 9.2 | 0.9 | 0 |
| 4.35 | 87.9 | 3.1 | 9 | 0 | 0 |
| 10 | 95.2 | 0 | 4.8 | 0 | 0 |

A mixture of unreacted oxycodone and four isomers of Formula V was dissolved in 5% acetic acid at a concentration of 1 mg/nil and heated to 100° C. The course of the hydrolysis was monitored by LC/MS. Results from the hydrolysis are shown in Table 11 and illustrated in FIG. 13.

TABLE 11

| Hours | % Oxycodone | % Va* | % Vb* | % Vc* + Vd* |
|---|---|---|---|---|
| 0 | 1 | 26.1 | 25.3 | 40.1 |
| 0.33 | 31.8 | 17.3 | 19 | 27.4 |
| 0.67 | 46.4 | 13 | 15.3 | 21.9 |
| 1 | 56.5 | 7.8 | 11.9 | 19.3 |
| 2 | 72.8 | 3.1 | 4.7 | 11.8 |
| 4 | 85.4 | 2.6 | 1 | 4.1 |

*The stereochemistry of each of the isomers Va-Vd is to be determined.

Example 14

Figure 14:
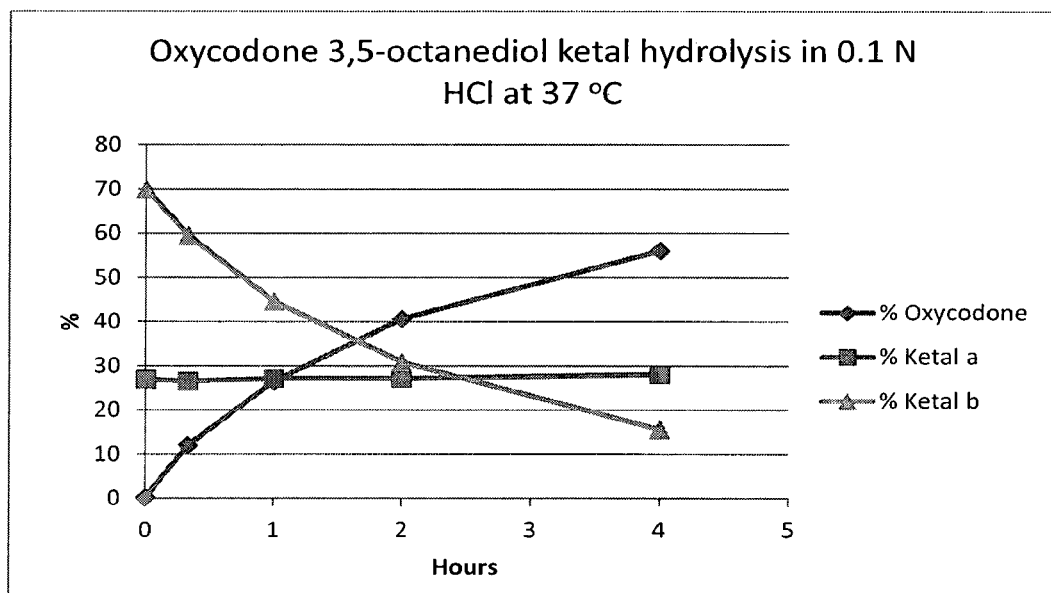
FIG. 14 is a graph of the hydrolysis of a mixture of a number of isomers of oxycodone 3,5-octanediol ketals in 0.1 N HCl at 37° C., and the release of oxycodone. The ketal isomers resolved into two different peaks under the LCMS conditions, and were tracked.

A mixture of oxycodone 3,5-octanediol ketals was prepared as described above and subjected to hydrolysis in 0.1 N HCl at 37° C. at a concentration of 1 mg/ml. Results from the analysis are shown below in Table 12 and FIG. 14. The lines representing the peaks of Ketal a and Ketal b are mixtures of isomers that were unresolved under the LCMS conditions used.

TABLE 12

| Hours | % Oxycodone | % Ketal a | % Ketal b |
|---|---|---|---|
| 0 | 0.3 | 27 | 70 |
| 0.33 | 12.1 | 26.6 | 59.6 |
| 1 | 26.5 | 27.2 | 44.7 |
| 2 | 40.7 | 27.2 | 30.9 |
| 4 | 56.1 | 28.1 | 15.7 |

Example 15

Ketal Hydrolysis at Varying pH

Figure 15:
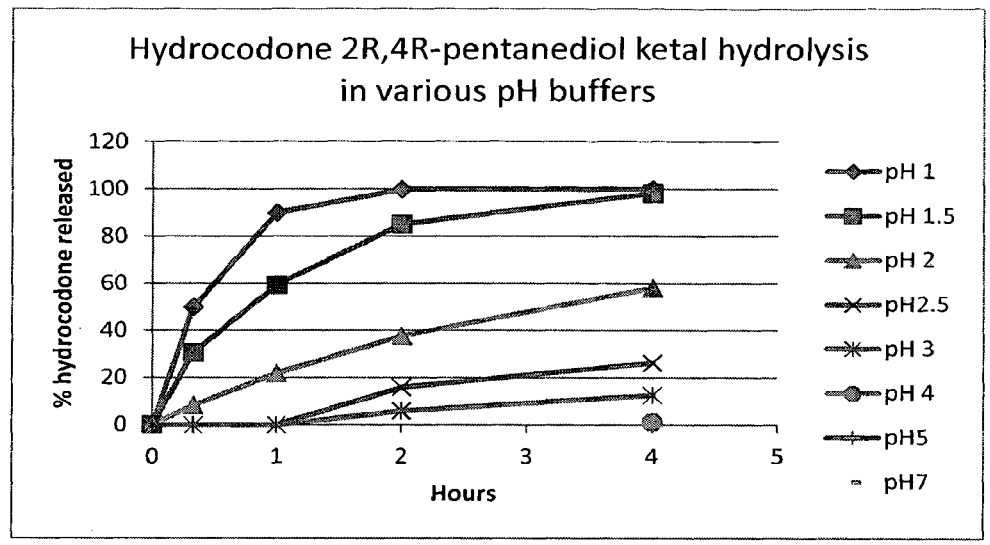
FIG. 15 is a graph of the hydrolysis of hydrocodone 2R,4R-pentanediol ketal in buffers of different pHs at 37° C.

Hydrocodone 2R,4R-pentanediol ketal was hydrolyzed at 37° C. in various pH buffers at a concentration of 1 mg/ml. The data from the hydrolysis is shown in Table 13a below and in FIG. 15. The data show that hydrolysis of the ketal to generate the parent hydrocodone is fastest at pH 1.

TABLE 13a

| Hours | pH 1 | pH 1.5 | pH 2 | pH 2.5 | pH 3 |
|---|---|---|---|---|---|
| 0 | 0 | 0 | 0 | 0 | 0 |
| 0.33 | 50 | 30.6 | 8.3 | 0 | 0 |
| 1 | 90 | 59.4 | 21.9 | 0 | 0 |
| 2 | 99.8 | 85.1 | 37.7 | 15.9 | 5.9 |
| 4 | 100 | 98.2 | 58.2 | 26.4 | 12.7 |

TABLE 13a-continued

| Hours | pH 4 | pH 5 | pH 7 | pH 12 |
|---|---|---|---|---|
| 0 | | | | |
| 0.33 | | | | |
| 1 | | | | |
| 2 | | | | |
| 4 | 1.3* | 0.15* | 0.01* | 0.01* |

*Hydrolysis times estimated from longer hydrolysis times

Figure 16:
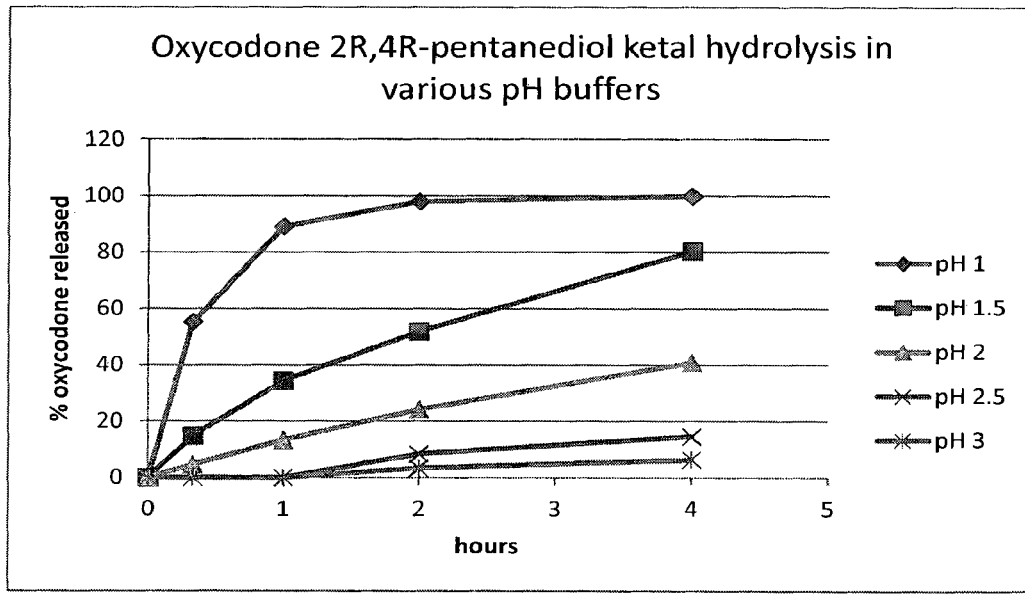
FIG. 16 is a graph of the hydrolysis of hydrocodone 2R,4R-pentanediol ketal in buffers of different pHs at 37° C.

Oxycodone 2R,4R-pentanediol ketal was hydrolyzed at 37° C. in various pH buffers at a concentration of 1 mg/ml. The data from the hydrolysis is shown in Table 13b below and in FIG. 16. The data show that hydrolysis of the ketal to generate the parent hydrocodone is fastest at pH 1.

TABLE 13b

| Hours | pH 1 | pH 1.5 | pH 2 | pH 2.5 | pH 3 |
|---|---|---|---|---|---|
| 0 | 0 | 0 | 0 | 0 | 0 |
| 0.33 | 55.2 | 14.9 | 4.6 | 0 | 0 |
| 1 | 89.2 | 34.4 | 13.3 | 0 | 0 |
| 2 | 98 | 51.9 | 24.2 | 8.4 | 3.4 |
| 4 | 100 | 80.4 | 40.9 | 14.7 | 6.4 |

Example 16

A mixture of four isomers of Formula IV (IVA-IVD) at a concentration of 1 mg/ml was tested for hydrolysis in the soft drink Coca Cola®, or in a pH 4 buffer, or in a pH 7 buffer. As shown in Table 14 below, the mixture showed very low degree of hydrolysis after 3 days under each of the tested conditions.

TABLE 14

| Solvent | Temperature | Hydrolysis to Oxycodone |
|---|---|---|
| Coca Cola® | 23° C. | 5% |
| pH 4 Buffer | 37° C. | 4% |
| pH 7 Buffer | 37° C. | 0% |

Having now fully described this invention, it will be understood by those of ordinary skill in the art that the same can be performed within a wide and equivalent range of conditions, formulations and other parameters without affecting the scope of the invention or any embodiment thereof.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

All patents and publications cited herein are fully incorporated by reference herein in their entirety.

What is claimed is:

1. A method of treating or ameliorating pain in a mammal identified as in need thereof through an oxycodone therapy, comprising orally administering to the mammal an effective amount of one or more compounds of Formula II, III, or V:

II

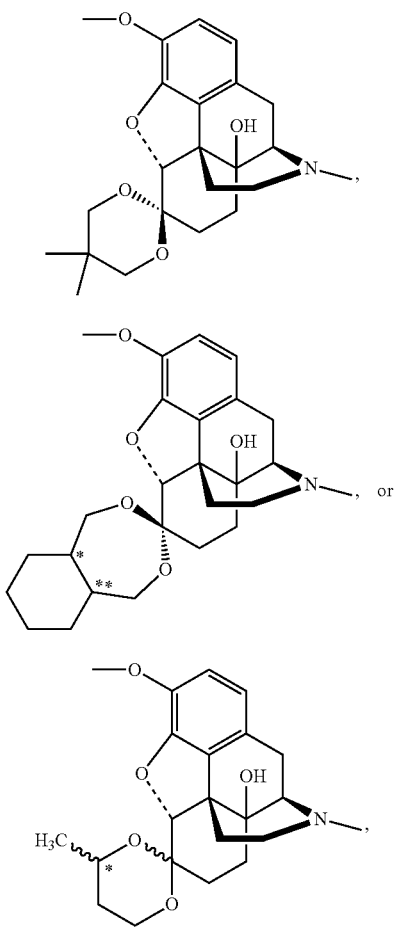

or a pharmaceutically acceptable salt thereof, wherein the carbon atom labeled * or ** is in R or S configuration, and wherein the method provides the mammal an extended release of the oxycodone, as compared to an oral administration of the oxycodone or a pharmaceutically acceptable salt thereof in an immediate release form to the mammal.

2. The method of claim 1, wherein the pain is acute pain or chronic pain.

3. The method of claim 1, wherein the method comprises the administration of an effective amount of a compound of Formula V selected from the group consisting of

VA

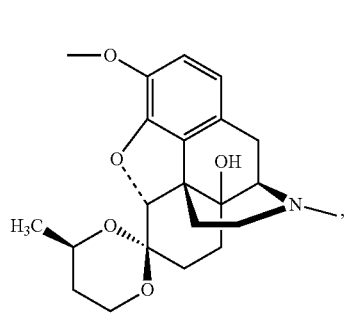

VB

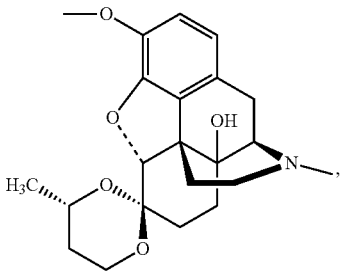

VC

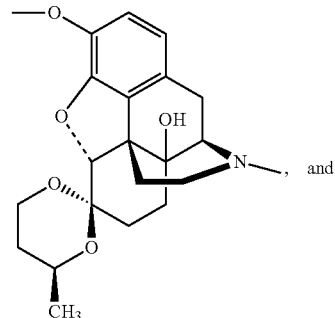

VD

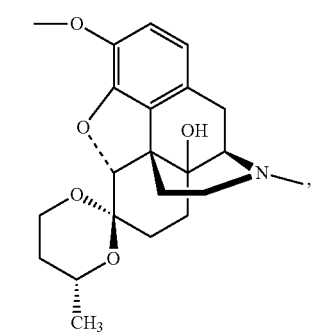

or a pharmaceutically acceptable salt thereof.

4. The method of claim 3, wherein the method comprises administering to the mammal a mixture of two or more compounds of Formula V or pharmaceutically acceptable salts thereof.

5. The method of claim 3, wherein the method comprises administering to the mammal a mixture comprising compounds VA, VB, VC, and VD, or pharmaceutically acceptable salts thereof.

6. The method of claim 1, wherein the method comprises the administration of an effective amount of one or more compounds of Formula II or Formula III:

II

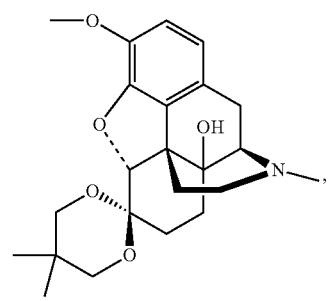

-continued

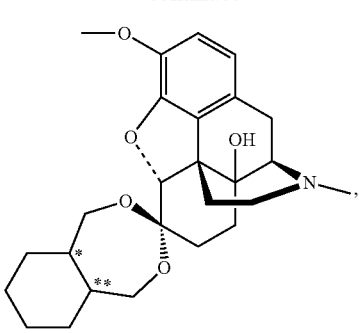

III or a pharmaceutically acceptable salt thereof.

7. The method of claim 6, wherein the method comprises the administration of a mixture comprising two or more stereoisomers of a compound of Formula III, or pharmaceutically acceptable salts thereof.

8. The method of claim 1, wherein the method reduces an abuse or misuse potential of the oxycodone therapy.

9. The method of claim 1, wherein the method reduces euphoric effects of the oxycodone therapy.

10. The method of claim 1, wherein the compound of Formula II, III, or V is administered at a dose of from 0.1 to 5 mg/kg, or a molar equivalent amount of a pharmaceutically acceptable salt thereof, based on the body weight of the mammal.

11. The method of claim 1, wherein the compound of Formula II, III, or V, or a pharmaceutically acceptable salt thereof, is administered as part of a pharmaceutical composition comprising between 5 mg and 320 mg of the compound of Formula II, III, or V or a molar equivalent of the pharmaceutically acceptable salt thereof.

* * * * *